(12) United States Patent
Kakizuka et al.

(10) Patent No.: US 9,206,129 B2
(45) Date of Patent: Dec. 8, 2015

(54) AGENT FOR TREATMENT OF EYE DISEASES

(75) Inventors: Akira Kakizuka, Kyoto (JP); Seiji Hori, Kyoto (JP); Hanako Ikeda, Kyoto (JP); Nagahisa Yoshimura, Kyoto (JP); Noriko Nakano, Kyoto (JP); Toshiyuki Shudo, Osaka (JP); Tomohiro Fuchigami, Osaka (JP)

(73) Assignees: Daito Chemix Corporation, Osaka (JP); Kyoto University, Kyoto (JP)

( * ) Notice: Subject to any disclaimer, the term of this patent is extended or adjusted under 35 U.S.C. 154(b) by 0 days.

(21) Appl. No.: 13/876,596

(22) PCT Filed: Sep. 30, 2011

(86) PCT No.: PCT/JP2011/073160
§ 371 (c)(1),
(2), (4) Date: Jul. 3, 2013

(87) PCT Pub. No.: WO2012/043891
PCT Pub. Date: Apr. 5, 2012

(65) Prior Publication Data
US 2014/0148416 A1    May 29, 2014

(30) Foreign Application Priority Data
Sep. 30, 2010   (JP) .................. 2010-221873

(51) Int. Cl.
*C07D 213/76*    (2006.01)
*A61K 31/4418*   (2006.01)
*C07D 213/77*    (2006.01)

(52) U.S. Cl.
CPC .......... *C07D 213/76* (2013.01); *A61K 31/4418* (2013.01); *C07D 213/77* (2013.01)

(58) Field of Classification Search
CPC ................................................ A61K 31/4418
See application file for complete search history.

(56) References Cited

U.S. PATENT DOCUMENTS

2005/0245509 A1   11/2005   Nakajima et al.
2011/0212993 A1    9/2011   Okamoto et al.

FOREIGN PATENT DOCUMENTS

| JP | 2004-107335 A | 4/2004 |
| JP | 2009-227650 A | 10/2009 |
| JP | 2010-193903 A | 9/2010 |

*Primary Examiner* — Zohreh Fay
(74) *Attorney, Agent, or Firm* — Morgan, Lewis & Bockius LLP

(57) ABSTRACT

The present invention provides agents effective to treat eye diseases, pharmaceutical compositions comprising them, methods for preparing pharmaceuticals for treatment of eye diseases comprising using the agents, use of the agents in manufacture of pharmaceuticals for treatment of eye diseases and methods for treating eye diseases comprising administering the agents or the pharmaceutical compositions. The eye diseases treated by the present invention include particularly glaucoma, especially normal tension glaucoma, or retinitis pigmentosa. The present invention provides the compound of formula (I)

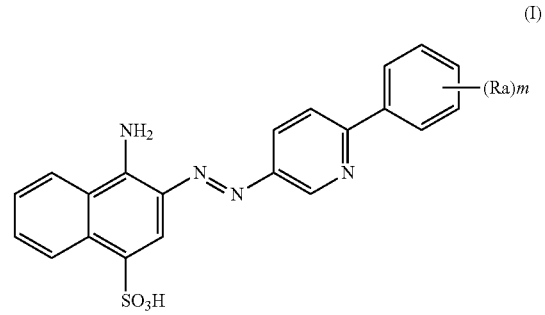

wherein R is as defined in the description.

12 Claims, 18 Drawing Sheets

Number of ganglion neurons
(neuroprotective agent administered subconjunctivally + intravitreally)

Number of ganglion neurons
(GLAST -/- mice)

physiological saline    Compound 32

| layer of photoreceptor cells
~ junction of outer segment and inner segment layer of photoreceptor cells OCT Thickness of entire retina OCT Thickness of entire retina Electroretinogram (ERG) b-wave amplitudes Electroretinogram (ERG) b-wave amplitudes

AGENT FOR TREATMENT OF EYE DISEASES

TECHNICAL FIELD

The present invention provides agents effective to treat eye diseases, pharmaceutical compositions comprising them, methods for preparing pharmaceuticals for treatment of eye diseases comprising using the agents, use of the agents in manufacture of pharmaceuticals for treatment of eye diseases and methods for treating eye diseases comprising administering the agents or the pharmaceutical compositions. The eye diseases treated by the present invention include particularly glaucoma, especially normal tension glaucoma, or retinitis pigmentosa.

BACKGROUND ART

Glaucoma is a disease characterized by visual field loss caused by degeneration or shedding of retinal ganglion neurons, which may lead to blindness if left untreated. Elevated intraocular pressure is one of the pathoetiologies of glaucoma, but, for example in Japan, the number of patients of glaucoma which is not associated with the elevated intraocular pressure, i.e. normal tension glaucoma, is up to 60% of the total number of the patients of glaucoma. The current therapy for glaucoma, whether drug administration or surgery, depends on intraocular pressure reduction. The progression of glaucoma may be arrested or delayed by reducing the intraocular pressure of the patients of normal tension glaucoma, but even if the intraocular pressure is reduced, no or little delay of the progression of glaucoma is achieved in some patients. Furthermore, in the first place, since the intraocular pressure of the patients of normal tension glaucoma is normal, the reduction of the ocular pressure may not be possible or sufficient. Alternatively, even in the case of glaucoma associated with the elevated intraocular pressure, sometimes the progression of glaucoma may not be sufficiently delayed or the reduction of the intraocular pressure may be difficult.

For the treatment of glaucoma, agents such as sympathomimetic agents (nonselective agonists such as epinephrine, $\alpha_2$ agonists such as apraclonidine), sympatholytic agents ($\beta$-blockers such as timolol, befunolol, $\alpha_1$-blocker such as bunazosin hydrochloride), parasympathomimetic agents (such as pilocarpine), carbonic anhydrase inhibitors (such as acetazolamide, brinzolamide), prostaglandins (such as isopropyl unoprostone, latanoprost, travoprost, bimatoprost) are used. These agents reduce the intraocular pressure.

Retinitis pigmentosa is a disease characterized by visual field loss and night blindness caused by degeneration or shedding of photoreceptor cells. The half of the cases of retinitis pigmentosa is hereditary, and the other half is sporadic. The method for treating retinitis pigmentosa is not sufficiently established.

CITATION LIST

Patent Literature

Patent Literature 1: JP-A-2010-193903
Patent Literature 2: JP-A-2009-298808
Patent Literature 3: JP-A-2009-227650

SUMMARY OF INVENTION

Technical Problem to be Solved by the Invention

Therefore, pharmaceutical agents capable of treating glaucoma, especially normal tension glaucoma or glaucoma which does not respond to the therapy reducing the intraocular pressure are required. Pharmaceutical agents capable of treating retinitis pigmentosa are also required.

Solution to Problem

The present invention provides the compounds of formula (I):

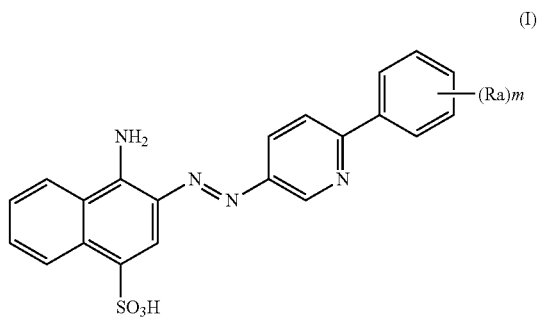

wherein
Ra is independently selected from the group consisting of halo, hydroxy, alkyl, halo-substituted alkyl, aryl, halo- or alkyl-substituted aryl, alkoxy, hydroxy- or carboxy-substituted alkoxy, aryloxy, halo- or alkyl-substituted aryloxy, CHO, C(O)-alkyl, C(O)-aryl, C(O)-alkyl-carboxyl, C(O)-alkylene-carboxy ester and cyano,
m is an integer selected from 0 to 4,
or oxides, esters, prodrugs, pharmaceutically acceptable salts or solvates thereof (the compounds of the present invention).

In a further aspect, the present invention provides pharmaceutical compositions for treating glaucoma or retinitis pigmentosa comprising the compounds of formula (I) above or oxides, esters, prodrugs, pharmaceutically acceptable salts or solvates thereof.

In a further aspect, the present invention provides methods for treating glaucoma or retinitis pigmentosa comprising administering the compounds of formula (I) above or oxides, esters, prodrugs, pharmaceutically acceptable salts or solvates thereof to a subject in need thereof.

In a further aspect, the present invention provides the compounds of formula (I) above or oxides, esters, prodrugs, pharmaceutically acceptable salts or solvates thereof for treating glaucoma or retinitis pigmentosa.

In a preferred embodiment of the present invention, glaucoma is normal tension glaucoma or glaucoma which does not respond to the therapy reducing the intraocular pressure.

Effects of Invention

The compounds of the present invention can inhibit the degeneration or shedding of the retinal ganglion neurons characteristic of glaucoma independently from change of the ocular pressure. The compounds of the present invention can also inhibit the degeneration or shedding of the photoreceptors characteristic of retinitis pigmentosa. The present invention, therefore, can provide the agents for treating glaucoma based on new mechanism which has not been known ever. The present invention can also provide the new agents useful for the treatment of retinitis pigmentosa for which no established therapy is available.

DESCRIPTION OF EMBODIMENTS

Definition

Figure 1:
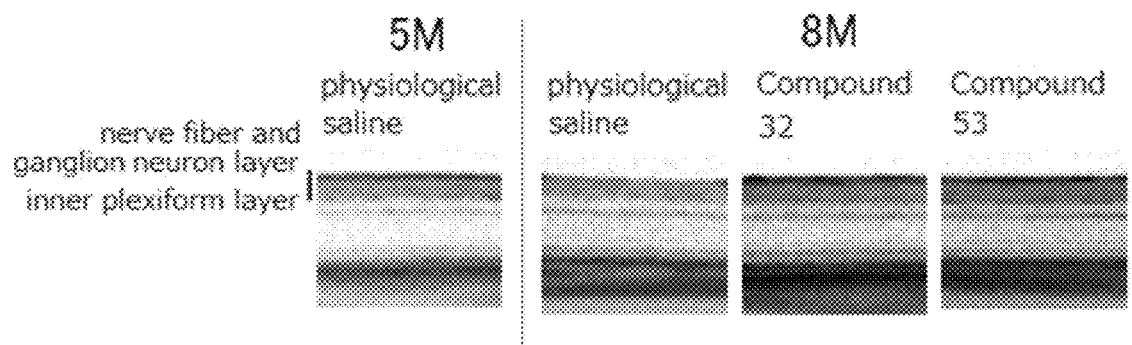
FIG. 1: From the left, the OCT images of the retinae of the 5-month-old (5M) DBA/2J mice administered with the physiological saline and the 8-month-old (8M) DBA/2J mice administered with the physiological saline, Compound 32 and Compound 53.

Unless defined otherwise, the terms used herein have the same meaning as commonly understood to one of ordinary skill in the art in the field of organic chemistry, medicine, pharmacology, molecular biology, microbiology and the like. The definitions of several terms used herein are described below. These definitions herein take precedence over the general understanding.

"Alkyl" refers to monovalent saturated aliphatic hydrocarbyl groups having from 1 to 10 carbon atoms and preferably 1 to 6 carbon atoms. The term "$C_{x-y}$alkyl" refers to alkyl groups having from x to y carbons. Alkyl includes, but not limited to, by way of example, linear and branched hydrocarbyl groups such as methyl($CH_3$—), ethyl($CH_3CH_2$—), n-propyl($CH_3CH_2CH_2$—), isopropyl(($CH_3$)$_2$CH—), n-butyl ($CH_3CH_2CH_2CH_2$—), isobutyl(($CH_3$)$_2$CHCH$_2$—), sec-butyl(($CH_3$)($CH_3CH_2$)CH—), t-butyl(($CH_3$)$_3$C—), n-pentyl ($CH_3CH_2CH_2CH_2CH_2$—), and neopentyl(($CH_3$)$_3$CCH$_2$—).

The prefix "substituted" for a group means that one or more hydrogen atom of the group is replaced by an identical or different indicated substituent.

"Alkylene" refers to divalent saturated aliphatic hydrocarbyl groups having from 1 to 10 carbon atoms and preferably 1 to 6 carbon atoms. "$C_{x-y}$alkylene" refers to alkylene groups having from x to y carbons. The alkylidene and alkylene groups include branched and straight chain hydrocarbyl groups.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy and n-pentoxy.

"Aryl" or "Ar" refers to a monovalent aromatic carbocyclic group of from 6 to 14 carbon atoms having a single ring (e.g., phenyl) or multiple condensed rings (e.g., naphthyl or anthryl). Aryl groups typically include phenyl and naphthyl.

"Aryloxy" refers to the group —O-aryl, where aryl is as defined herein, and includes, by way of example, phenoxy and naphthoxy.

"Cyano" or "carbonitrile" refers to the group —CN.

"Carboxyl" or "carboxy" refers to —COOH or salts thereof.

"Carboxyl ester" or "carboxy ester" refers to the groups —C(O)O-alkyl wherein alkyl is defined herein.

"Halo" or "halogen" refers to fluoro, chloro, bromo or iodo.

"Hydroxy" or "hydroxyl" refers to the group —OH.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that the above definitions are not intended to include impermissible substitution patterns (e.g., methyl substituted with 5 fluoro groups). Such impermissible substitution patterns are well known to the skilled artisan.

"Compound" and "compounds" as used herein refers to a compound encompassed by the generic formula disclosed herein, any subgenus of those generic formulae, and any specific compounds within the generic and subgeneric formulae, including the oxide, ester, prodrug, pharmaceutically acceptable salt, or solvate thereof. The term further includes the stereoisomers and tautomers of the compound or compounds.

"Solvate" or "solvates" of a compound refer to those compounds, where the compound is as defined above, that are bound to a stoichiometric or non-stoichiometric amount of a solvent. Solvates includes solvates of the oxide, ester, prodrug, or pharmaceutically acceptable salt of the disclosed generic and subgeneric formulae. Preferred solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Prodrug" refers to any derivative of a compound of the embodiments that is capable of directly or indirectly providing a compound of the embodiments or an active metabolite or residue thereof when administered to a subject. Particularly favored derivatives and prodrugs are those that increase the bioavailability of the compounds of the embodiments when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester forms of the compounds of the invention. Examples of ester prodrugs include formate, acetate, propionate, butyrate, acrylate, and ethylsuccinate derivatives. A general overview of prodrugs is provided in T. Higuchi and V. Stella, Pro drugs as Novel Delivery Systems, Vol. 14 of the A.C.S. Symposium Series and Edward B. Roche, ed., Bioreversible Carriers in Drug Design, American Pharmaceutical Association and Pergamon Press, 1987, both of which are incorporated herein by reference.

"Pharmaceutically acceptable salt" refers to pharmaceutically acceptable salts derived from a variety of organic and inorganic counter ions well known in the art and include, by way of example, salts of sodium, potassium, calcium, magnesium, ammonium, and tetraalkylammonium, and salts of organic or inorganic acids, such as hydrochloride, hydrobromide, tartrate, mesylate, acetate, maleate, and oxalate. Pharmaceutically acceptable salt of a compound refers to pharmaceutically acceptable salts including salts of the oxide, ester, or prodrug of the disclosed generic and subgeneric formulae.

"Subject" refers to mammals and includes humans and non-human mammals.

"Treating" or "treatment" of a disease in a subject refers to 1) preventing the disease from occurring in a subject that is predisposed or does not yet display symptoms of the disease; 2) inhibiting the disease or arresting its development; or 3) ameliorating or causing regression of the disease. Especially, the treatment of the present invention is intended to be 1) or 2) above.

In one embodiment, the compounds of the present invention are those selected from Compounds 1 to 53 listed in Table 1 below, or oxides, esters, prodrugs, pharmaceutically acceptable salts or solvates thereof.

TABLE 1

| No. | Structure | Compound Name |
|---|---|---|
| 1 | 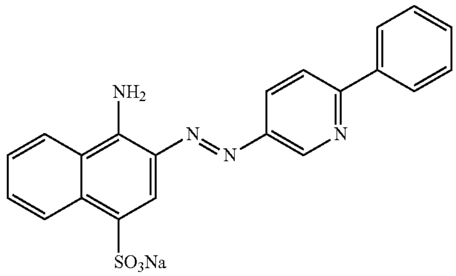 | 4-amino-3-(6-phenylpyridine-3-ylazo)naphthalene-1-sulfonic acid sodium salt |
| 2 | 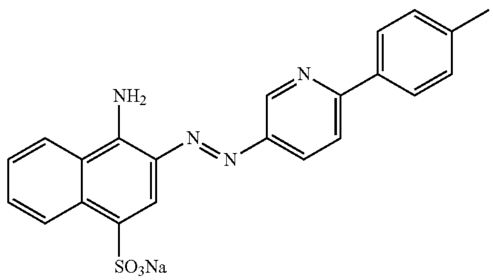 | 4-amino-3-(6-p-tolylpyridine-3-ylazo)naphthalene-1-sulfonic acid sodium salt |
| 3 | 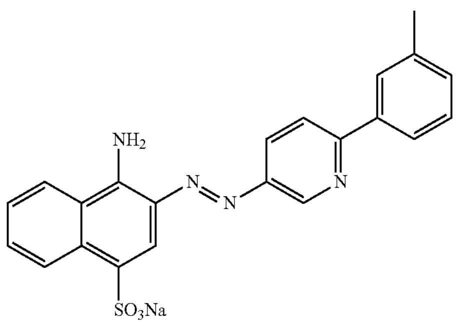 | 4-amino-3-(6-m-tolylpyridine-3-ylazo)naphthalene-1-sulfonic acid sodium salt |
| 4 | 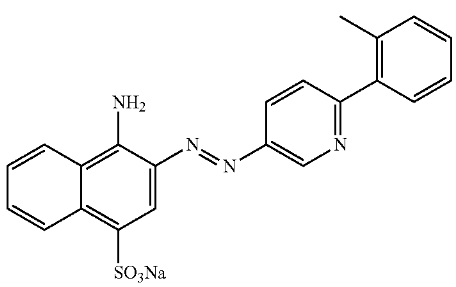 | 4-amino-3-(6-c-tolylpyridine-3-ylazo)naphthalene-1-sulfonic acid sodium salt |
| 5 | 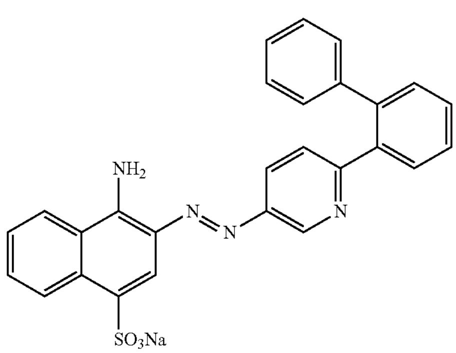 | 4-amino-3-(6-biphenyl-2-ylpyridine-3-ylazo)naphthalene-1-sulfonic acid sodium salt |

TABLE 1-continued

| No. | Structure | Compound Name |
|---|---|---|
| 6 | 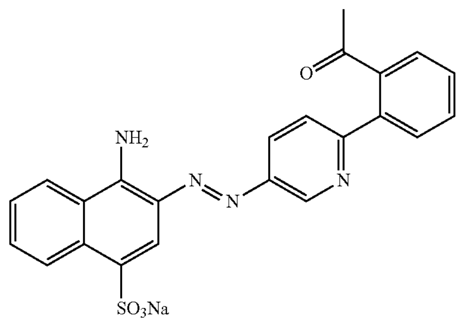 | 3-[6-(2-acetylphenyl)pyridine-3-ylazo]-4-aminonaphthalene-1-sulfonic acid sodium salt |
| 7 | 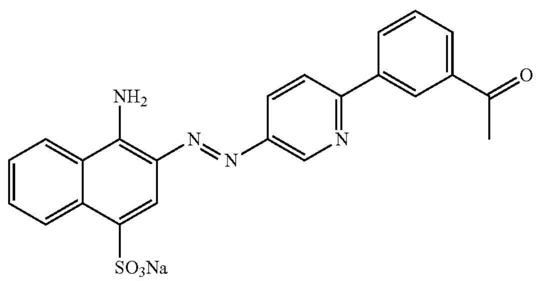 | 3-[6-(3-acetylphenyl)pyridine-3-ylazo]-4-aminonaphthalene-1-sulfonic acid sodium salt |
| 8 | 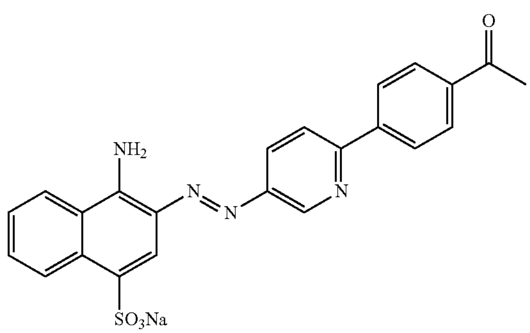 | 3-[6-(4-acetylphenyl)pyridine-3-ylazo]-4-aminonaphthalenesulfonic acid sodium salt |
| 9 | 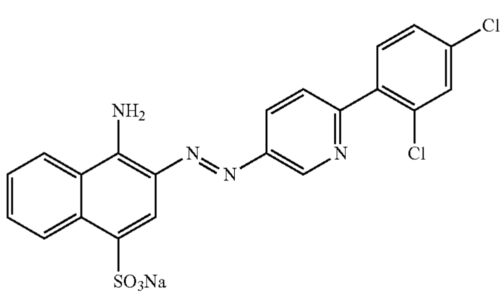 | 4-amino-3-[6-(2,4-dichlorophenyl)pyridine-3-ylazo]naphthalene-1-sulfonic acid sodium salt |
| 10 | 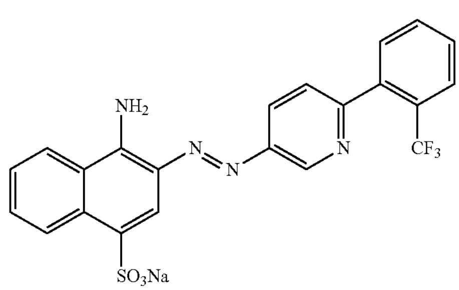 | 4-amino-3-[6-(2-trifluoromethylphenyl)pyridine-3-ylazo]naphthalene-1-sulfonic acid sodium salt |

TABLE 1-continued

| No. | Structure | Compound Name |
|---|---|---|
| 11 | 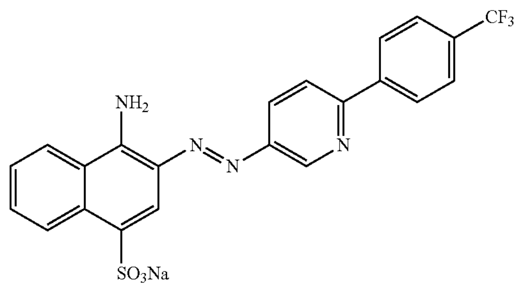 | 4-amino-3-[6-(4-trifluoromethylphenyl)pyridine-3-ylazo]naphthalene-1-sulfonic acid sodium salt |
| 12 | 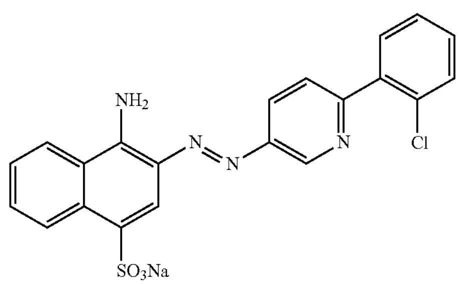 | 4-amino-3-[6-(2-chlorophenyl)pyridine-3-ylazo]naphthalene-1-sulfonic acid sodium salt |
| 13 | 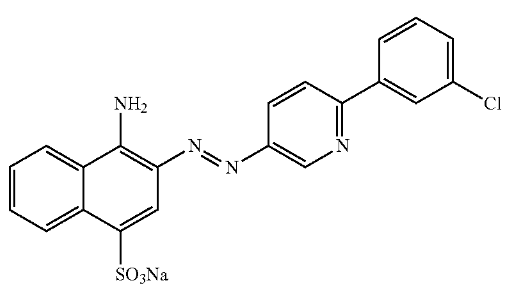 | 4-amino-3-[6-(3-chlorophenyl)pyridine-3-ylazo]naphthalene-1-sulfonic acid sodium salt |
| 14 | 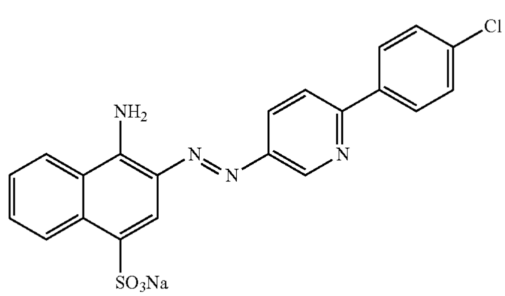 | 4-amino-3-[6-(4-chlorophenyl)pyridine-3-ylazo]naphthalene-1-sulfonic acid sodium salt |
| 15 | 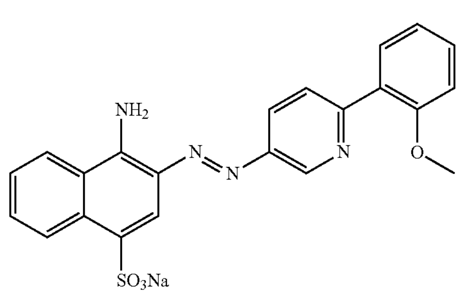 | 4-amino-3-[6-(2-methoxyphenyl)pyridine-3-ylazo]naphthalene-1-sulfonic acid sodium salt |

TABLE 1-continued

| No. | Structure | Compound Name |
|---|---|---|
| 16 | 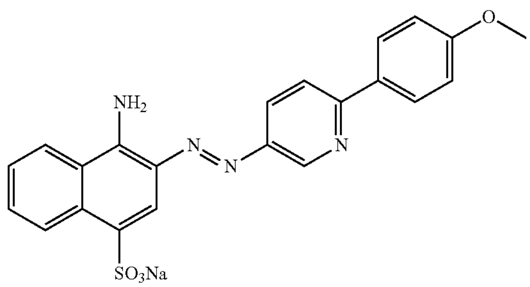 | 4-amino-3-[6-(4-methoxyphenyl)pyridine-3-ylazo]naphthalene-1-sulfonic acid sodium salt |
| 17 | 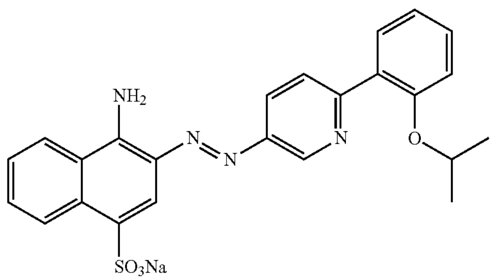 | 4-amino-3-[6-(2-isopropoxyphenyl)pyridine-3-ylazo]naphthalene-1-sulfonic acid sodium salt |
| 18 | 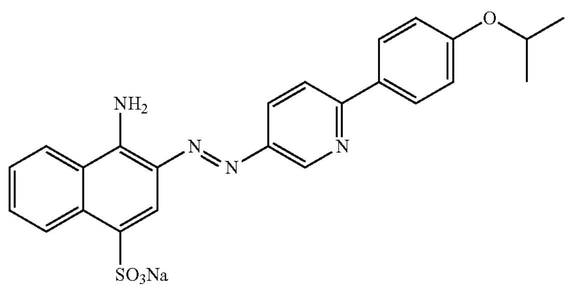 | 4-amino-3-[6-(4-isopropoxyphenyl)pyridine-3-ylazo]naphthalene-1-sulfonic acid sodium salt |
| 19 | 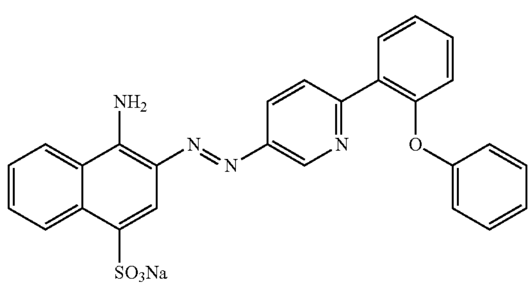 | 4-amino-3-[6-(2-phenoxyphenyl)pyridine-3-ylazo]naphthalene-1-sulfonic acid sodium salt |
| 20 | 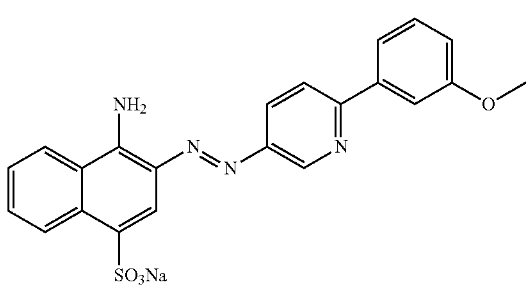 | 4-amino-3-[6-(3-methoxyphenyl)pyridine-3-ylazo]naphthalene-1-sulfonic acid sodium salt |

TABLE 1-continued

| No. | Structure | Compound Name |
|---|---|---|
| 21 | 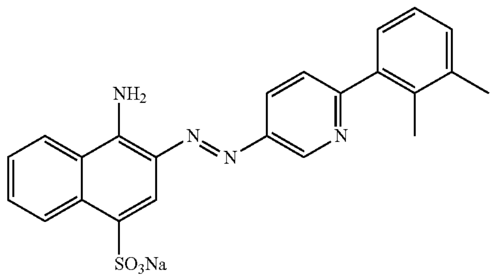 | 4-amino-3-[6-(2,3-dimethylphenyl)pyridine-3-ylazo]naphthalene-1-sulfonic acid sodium salt |
| 22 | 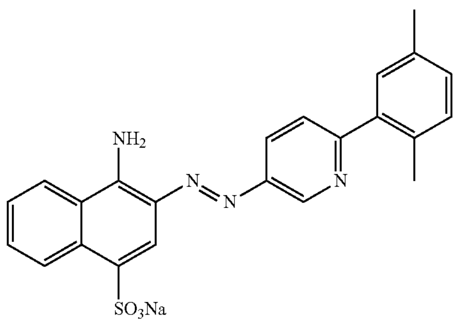 | 4-amino-3-[6-(2,5-dimethylphenyl)pyridine-3-ylazo]naphthalene-1-sulfonic acid sodium salt |
| 23 | 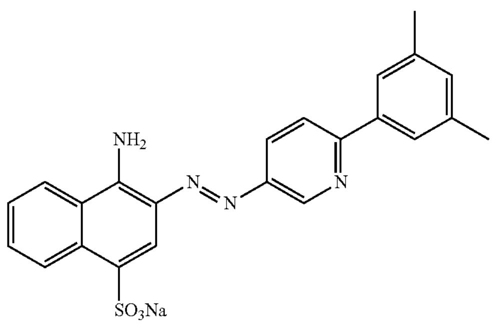 | 4-amino-3-[6-(3,5-dimethylphenyl)pyridine-3-ylazo]naphthalene-1-sulfonic acid sodium salt |
| 24 | 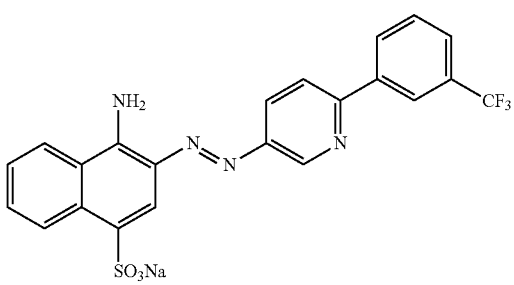 | 4-amino-3-[6-(3-trifluoromethylphenyl)pyridine-3-ylazo]naphthalene-1-sulfonic acid sodium salt |
| 25 | 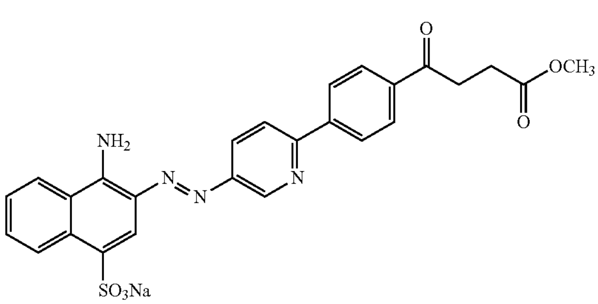 | methyl 4-{4-[5-(1-amino-sulfonaphthalene-2-ylazo)pyridine-2-yl]phenyl}-4-cxobutyrate sodium salt |

TABLE 1-continued

| No. | Structure | Compound Name |
|---|---|---|
| 26 | 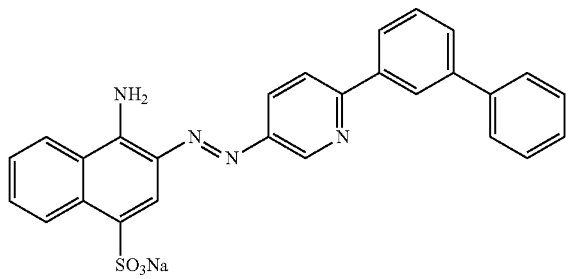 | 4-amino-3-(6-biphenyl-3-ylpyridine-3-ylazo)naphthalene-1-sulfonic acid sodium salt |
| 27 | 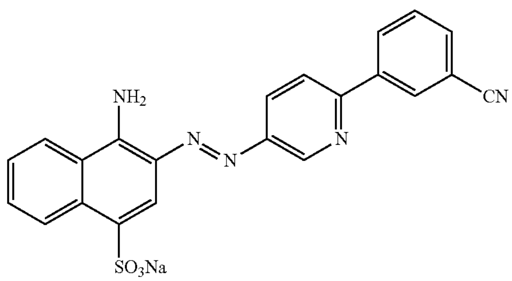 | 4-amino-3-[6-(3-cyanophenyl)pyridine-3-ylazo]naphthalene-1-sulfonic acid sodium salt |
| 28 | 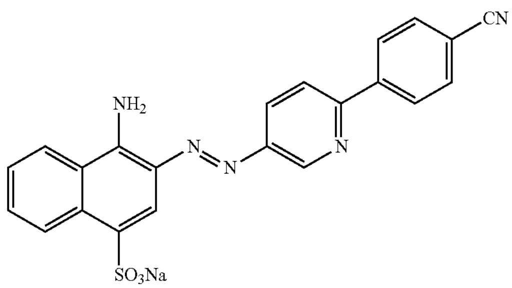 | 4-amino-3-[6-(4-cyanophenyl)pyridine-3-ylazo]naphthalene-1-sulfonic acid sodium salt |
| 29 | 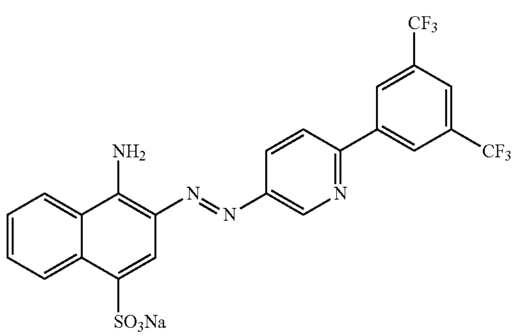 | 4-amino-3-[6-(3,5-bistrifluoromethylphenyl)pyridine-3-ylazo]naphthalenesulfonic acid sodium salt |
| 30 | 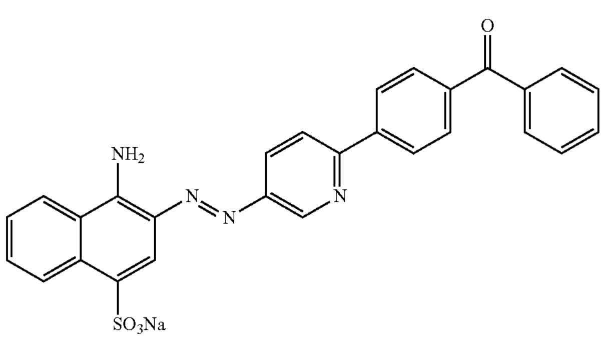 | 4-amino-3-[6-(4-benzoylphenyl)pyridine-3-ylazo]naphthalene-1-sulfonic acid sodium salt |

TABLE 1-continued

| No. | Structure | Compound Name |
|---|---|---|
| 31 | 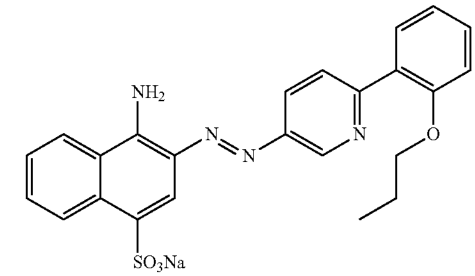 | 4-amino-3-[6-(2-propoxyphenyl)pyridine-3-ylazo]naphthalene-1-sulfonic acid sodium salt |
| 32 | 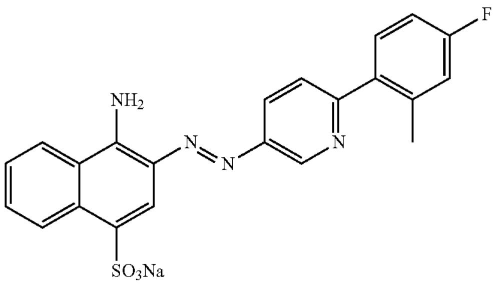 | 4-amino-3-[6-(4-fluoro-2-methylphenyl)pyridine-3-ylazo]naphthalene-1-sulfonic acid sodium salt |
| 33 | 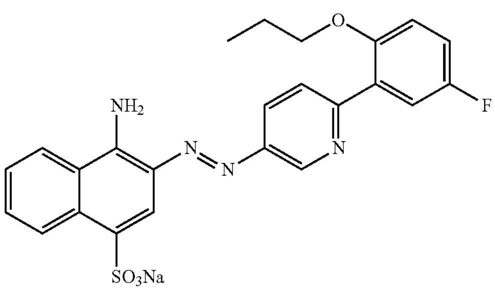 | 4-amino-3-[6-(5-fluoro-2-propoxyphenyl)pyridine-3-ylazo]naphthalene-1-sulfonic acid sodium salt |
| 34 | 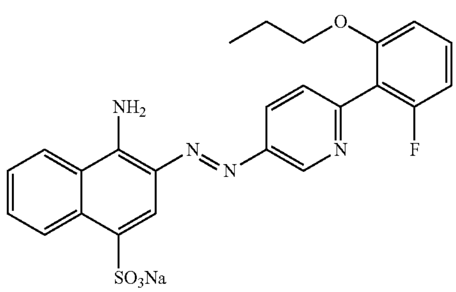 | 4-amino-3-[6-(2-fluoro-6-propoxyphenyl)pyridine-3-ylazo]naphthalene-1-sulfonic acid sodium salt |
| 35 | 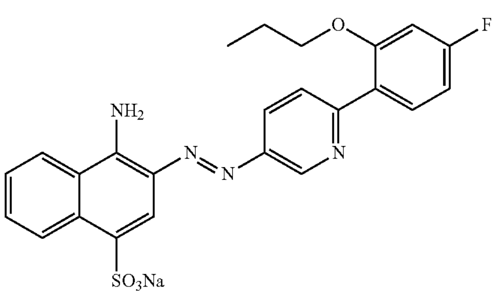 | 4-amino-3-[6-(4-fluoro-2-propoxyphenyl)pyridine-3-ylazo]naphthalene-1-sulfonic acid sodium salt |

TABLE 1-continued

| No. | Structure | Compound Name |
|---|---|---|
| 36 | 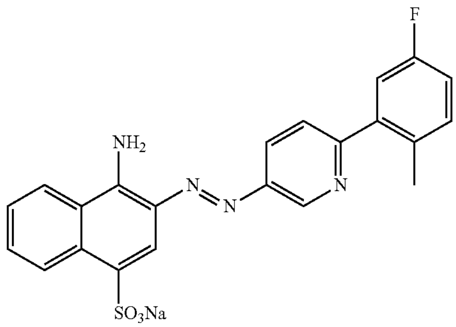 | 4-amino-3-[6-(5-fluoro-2-methylphenyl)pyridine-3-ylazo]naphthalene-1-sulfonic acid sodium salt |
| 37 | 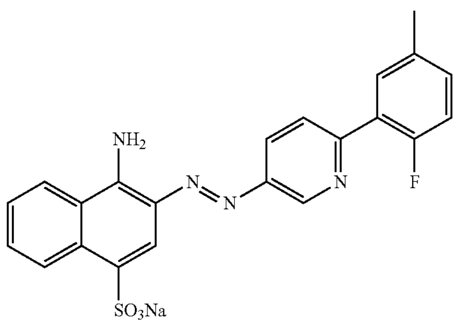 | 4-amino-3-[6-(2-fluoro-5-methylphenyl)pyridine-3-ylazo]naphthalene-1-sulfonic acid sodium salt |
| 38 | 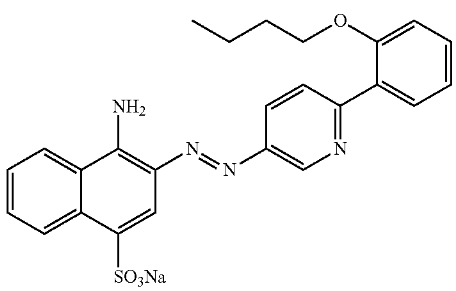 | 4-amino-3-[6-(2-butoxyphenyl)pyridine-3-ylazo]naphthalene-1-sulfonic acid sodium salt |
| 39 | 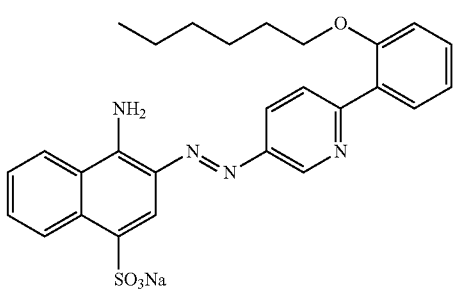 | 4-amino-3-[6-(2-hexyloxyphenyl)pyridine-3-ylazo]naphthalene-1-sulfonic acid sodium salt |
| 40 | 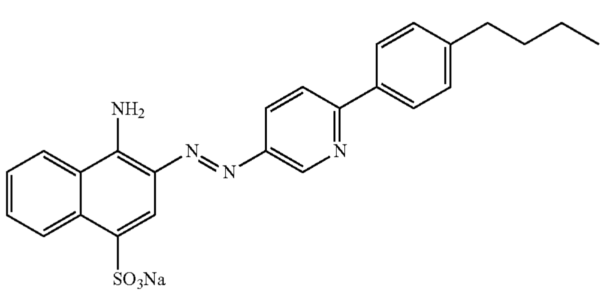 | 4-amino-3-[6-(4-butylphenyl)pyridine-3-ylazo]naphthalene-1-sulfonic acid sodium salt |

TABLE 1-continued

| No. | Structure | Compound Name |
|---|---|---|
| 41 | 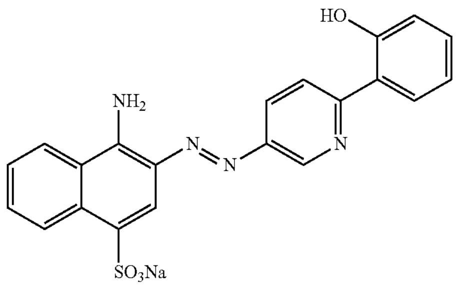 | 4-amino-3-[6-(2-hydroxyphenyl)pyridine-3-ylazo]naphthalene-1-sulfonic acid sodium salt |
| 42 | 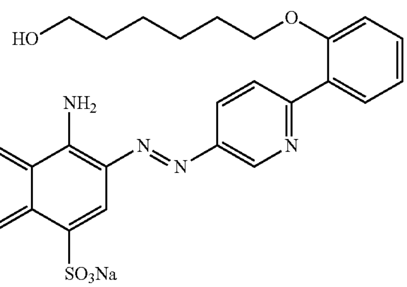 | 4-amino-3-{6-[2-(6-hydroxyhexyloxy)phenyl]pyridine-3-ylazo} naphthalene-1-sulfonic acid sodium salt |
| 43 | 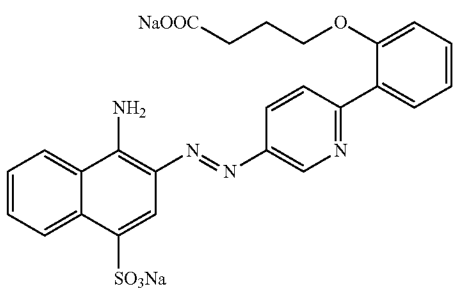 | 4-{2-[5-(1-amino-4-sulfonaphthalene-2-ylazo)pyridine-2-yl]phenoxy} butyric acid disodium salt |
| 44 | 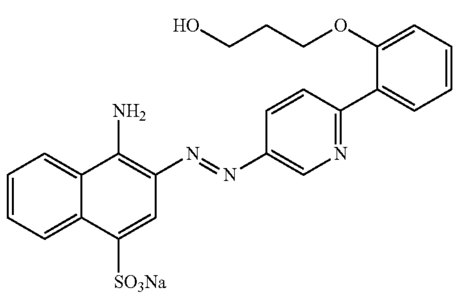 | 4-amino-3-{6-[2-(3-hydroxypropoxy)phenyl]pyridine-3-ylazo} naphthalene-1-sulfonic acid sodium salt |
| 45 | 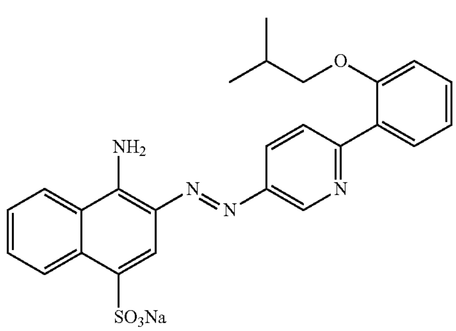 | 4-amino-3-[6-(2-isobutoxyphenyl)pyridine-3-ylazo]naphthalene-1-sulfonic acid sodium salt |

TABLE 1-continued

| No. | Structure | Compound Name |
|---|---|---|
| 46 | 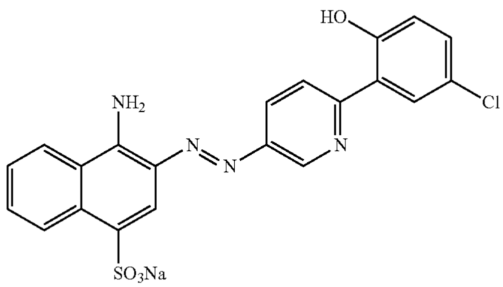 | 4-amino-3-[6-(5-chloro-2-hydroxyphenyl)pyridine-3-ylazo]naphthalene-1-sulfonic acid sodium salt |
| 47 | 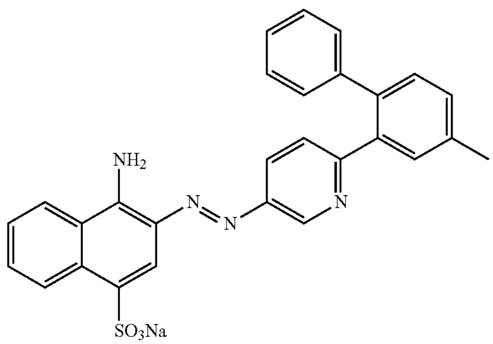 | 4-amino-3-[6-(4-methylbiphenyl-2-yl)pyridine-3-ylazo]naphthalene-1-sulfonic acid sodium salt |
| 48 | 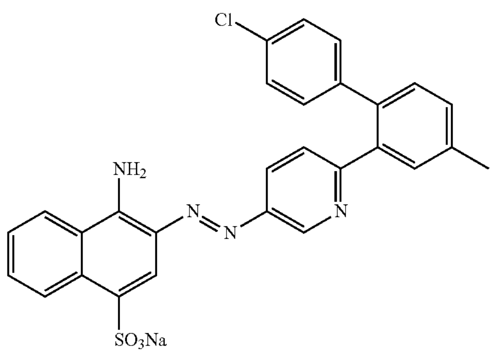 | 4-amino-3-[6-(4'-chloro-4-methylbiphenyl-2-yl)pyridine-3-ylazo]naphthalene-1-sulfonic acid sodium salt |
| 49 | 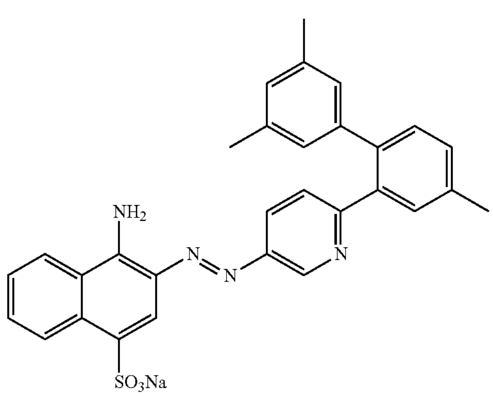 | 4-amino-3-[6-(4,3',5'-trimethylbiphenyl-2-yl)pyridine-3-ylazo]naphthalene-1-sulfonic acid sodium salt |

TABLE 1-continued

| No. | Structure | Compound Name |
|---|---|---|
| 50 | 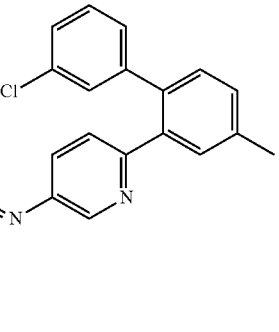 | 4-amino-3-[6-(3'-chloro-4-methylbiphenyl-2-yl)pyridine-3-ylazo]naphthalene-1-sulfonic acid sodium salt |
| 51 | 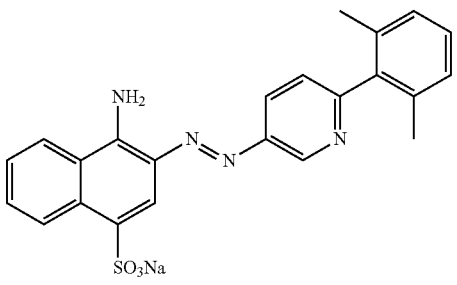 | 4-amino-3-[6-(2,6-dimethylphenyl)pyridine-3-ylazo]naphthalene-1-sulfonic acid sodium salt |
| 52 | 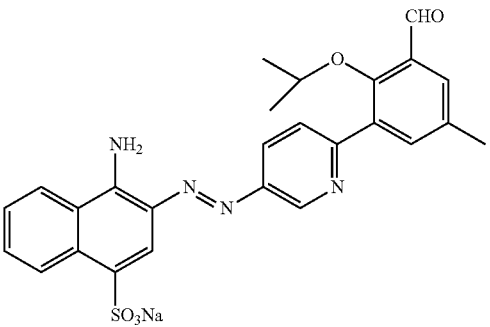 | 4-amino-3-[6-(3-formyl-2-isopropoxy-5-methylphenyl)pyridine-3-ylazo]naphthalene-1-sulfonic acid sodium salt |
| 53 | 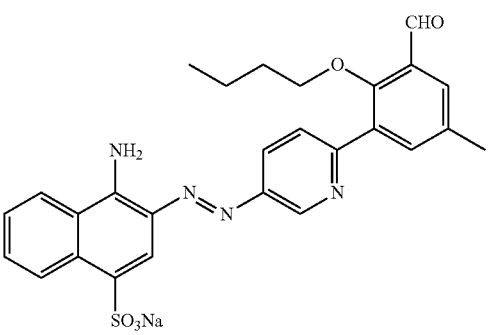 | 4-amino-3-[6-(3-formyl-2-butoxy-5-methylphenyl)pyridine-3-ylazo]naphthalene-1-sulfonic acid sodium salt |

In a particularly preferred embodiment, the compounds of the present invention are the compounds of formulae

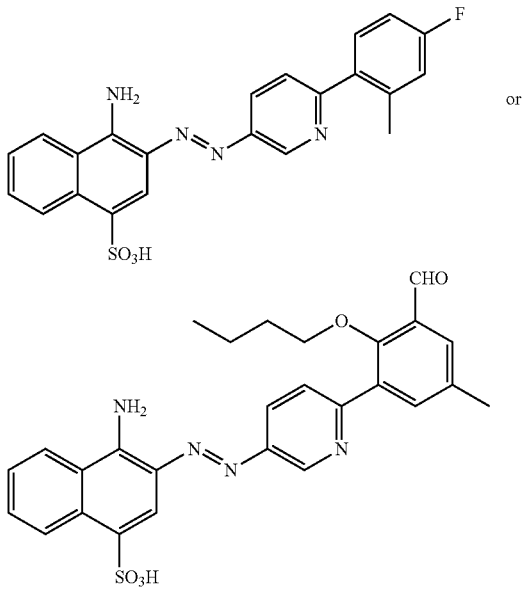

(Compound 32 or 53 listed in Table 1 above) or oxides, esters, prodrugs, pharmaceutically acceptable salts or solvates thereof, especially sodium salts thereof.

It will also be apparent to those skilled in the art that the compounds of the invention, including the compounds of formula (I), or the pharmaceutically acceptable salts, esters, oxides, and prodrugs of any of them, may be subject to tautomerization and may therefore exist in various tautomeric forms.

The compounds of formula (I) as well as the pharmaceutically acceptable salts, esters, oxides, and prodrugs of any of them may comprise asymmetrically substituted carbon atoms. Such asymmetrically substituted carbon atoms can result in the compounds existing in enantiomers, diastereomers, and other stereoisomeric forms that may be defined, in terms of absolute stereochemistry, such as in (R)- or (S)- forms. As a result, all such possible isomers, individual stereoisomers in their optically pure forms, mixtures thereof, racemic mixtures (or "racemates"), mixtures of diastereomers, as well as single diastereomers of the compounds are contemplated. The terms "S" and "R" configuration, as used herein, are as defined by the IUPAC 1974 RECOMMENDATIONS FOR SECTION E, FUNDAMENTAL STEREOCHEMISTRY, Pure Appl. Chem. 45:13-30 (1976).

Glaucoma

The normal intraocular presser is 10~21 mmHg. It is believed that the retinal ganglion neurons are degenerated or shed due to the intraocular pressure elevated over this range (typically 25 mmHg or higher) for some reason, resulting in glaucoma. In recent years, however, it is observed that many patients having the normal intraocular pressure (10~21 mmHg) develop glaucoma. For such patients, the reduction of the intraocular pressure may not be applicable, effective, or sufficient. Even for the patients of glaucoma with the elevated intraocular pressure, the reduction of the intraocular pressure may not be effective or sufficient (these patients of glaucoma are sometimes called the patients who do not respond to the therapy reducing the intraocular pressure). Thus, the compounds of the present invention which can inhibit degeneration or shedding of the retinal ganglion neurons independently from change of the ocular pressure may be useful for the treatment of normal tension glaucoma and glaucoma which does not respond to the therapy reducing the intraocular pressure. The term "independently from change of the intraocular pressure" used herein means that the intraocular pressure of a subject is not remarkably changed by administering the compound of the present invention, whether the intraocular pressure is elevated or normal before administering the compound. For example, it means that the ocular pressures before and after the treatment of the present invention are within the range of ±5 mmHg, preferably the range of ±10%. The intraocular pressure may be measured by any method which is available to those skilled in the art, in particular preference by using a commercially available machine for measuring the ocular pressure, for example contact type Goldmann tonometer.

The compounds of the present invention can treat glaucoma independently from the intraocular pressure. This does not mean to exclude the combination of the present invention and the therapy reducing the intraocular pressure. The therapy reducing the intraocular pressure which can be combined with the present invention includes, but not limited to, administration of agents for treating glaucoma or ocular hypertension (for example, pilocarpine, distigmine, carteolol, timolol, betaxolol, nipradilol, levobunolol, bunazosin, dipivefrin, isopropyl unoprostone, latanoprost, travoprost, tafluprost, dorzolamide, brinzolamide and the like), laser surgery or surgical procedure.

Without being bound by theory, it is thought that the compounds of the present invention can regulate ATPase activity of valosin-containing protein (VCP) which is believed to be involved in death of neurons and thus have an effect to protect neurons. Valosin-containing protein (VCP) belongs to a sub-family of ATPase, AAA (ATPases Associated with diverse cellular Activities), and is highly conserved among species. ATPases belonging to AAA are characterized in that they possess SRH (Second region of homology) region consisting of a similar amino acid sequence as a common structure in their C-terminal, in addition to Walker A motif (WA) which binds to ATP and Walker B motif (WB) which is involved in hydrolysis by the ATPase. The coordinated activity of WA, WB and SRH regions is thought to hydrolyze ATPS. VCP is mainly consisted of four regions, N-terminal region, D1 ATPase (D1) region, D2 ATPase (D2) region and C-terminal region, and possesses two ATPase regions characteristic of AAA family. Among them, D2 ATPase region is considered to be mainly responsible for the ATPase activity. In the two ATPase regions ATPase domain is followed by α-helix-enriched region, each of them is called D1α and D2α domain, respectively. The N-terminal region is known to have a function binding to and recognizing ubiquitin or degenerated proteins, and to be a binding region with cofactors such as Npl4, Ufd1 and p47 (Non-patent Literature 1).

Retinitis Pigmentosa

Retinitis pigmentosa is a disease caused by death of photoreceptor cells, a type of neuron, especially rod photoreceptor cells. Without being bound by theory, the compounds of the present invention is believed to have an effect to protect the neurons and thus to be able to treat retinitis pigmentosa.

The ability of the compounds of the present invention for regulating ATPase activity is determined, for example by the following exemplary assay. Mouse VCP cDNA (the amino acid sequence is completely identical among mouse, rat and human) is added with a DNA sequence corresponding to a histidine tag at the amino-terminal, subcloned into a baculovirus vector pVL1392 (BD Bioscience), and expressed in Sf-9 insect cells. The protein is purified with a nickel column. After the purification the concentration of the protein is adjusted to 0.25-0.5 μg/ml and the protein is stored in a solution containing 50 mM TrisCl pH 8.0, 5 mM EDTA, 10% glycerol, and 15 mM DTT at 4° C. 500 ng of the purified VCP is mixed with 100 μM [γ-$^{32}$P]ATP (18.5 GBq/mmol) and the test substance in 20 μL of ATPase buffer (20 mM HEPES (pH7.4), 50 mM KCl, 5 mM MgCl$_2$, 15 mM DTT), and incubated at 37° C. for 10 minutes. The enzyme reaction is stopped with addition of 200 μL of an ice-cold solution containing 7% TCA and 1 mM K$_2$HPO$_4$. 50μ of a solution containing 3.75% ammonium molybdate and 0.02M tungstate silicic/3 NH$_2$SO$_4$ is added, followed by 300 μL of n-butylacetic acid, and then the liberated phosphate is extracted into the organic layer. The reaction tube is centrifuged for 5 minutes at 20,000 g to separate the aqueous layer and the organic layer, 200 μL of the organic layer is taken, and the beta ray radiated from the liberated phosphate is quantified with liquid scintillation counter. By measuring the ATPase activity in the presence of the test substance at various concentrations, ATPase inhibitory activity of the test substance is measured.

Synthetic Methods

In other aspects, provided are the methods of the manufacture of the compounds of formula (I) as described herein.

The compounds disclosed herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the compounds disclosed herein may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of the embodiments, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry (John Wiley and Sons, 4$^{th}$ Edition) and Larock's Comprehensive Organic Transformations (VCH Publishers Inc., 1989), or obvious modifications thereof, for instance, the disclosure of Examples herein.

The various starting materials, intermediates, and compounds of the embodiments may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Compounds of the embodiments may generally be prepared using a number of methods familiar to one of skill in the art, and may generally be made in accordance with the following reaction Scheme 1, which is described in detail in the Examples below.

General Schemes:

Scheme 1 illustrates a general method for the preparation of intermediates and compounds of the invention. These compounds are prepared from starting materials that are known in the art or are commercially available, or starting materials which can be easily prepared from such starting materials by those skilled in the art.

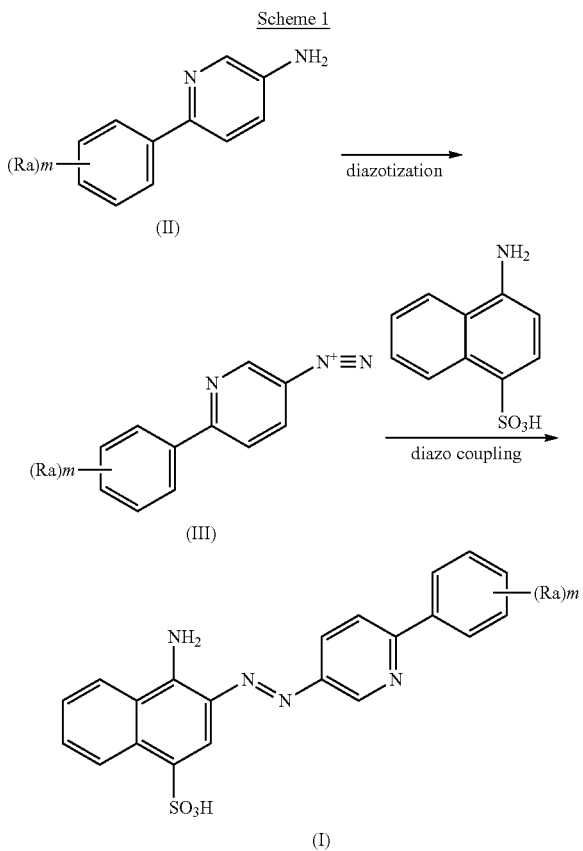

wherein Ra and m in formulae (II), (III) and (I) are as defined above in formula (I). The details and reaction conditions of diazotization of primary amine and diazo coupling of diazotized compound are well known to those skilled in the art, and they can conveniently select a suitable reaction condition from such well-known reaction conditions.

In scheme 1, typically the compound of formula (II) is suspended in a suitable solvent, for example, water, acetic acid or tetrahydrofuran or the mixture thereof, and reacted with nitrous acid or a salt or ester thereof, for example, nitrites such as potassium nitrite, calcium nitrite, silver nitrite, sodium nitrite or barium nitrite, or nitrite esters such as ethyl nitrite, isopentyl nitrite (also called as isoamyl nitrite), isobutyl nitrite, isopropyl nitrite or isopentyl nitrite with cooling, for example, below 10° C., preferably below 5° C. to achieve diazotization, resulting in the compound of formula (III).

In scheme 1, typically 4-amino-naphthalene-1-sulfonic acid can be suspended in a suitable solvent, for example water, and then subjected to diazo-coupling with the compound of formula (III) obtained above under a basic condition (for example, by addition of aqueous sodium hydroxide), for example, at pH 7 to 11, preferably at pH 8 to 10, with cooling, for example, at 0 to 15° C., preferably at 0 to 10° C. to give the compound of formula (I).

The following applies in general to all processes mentioned hereinbefore and hereinafter, while reaction conditions specifically mentioned above or below are preferred.

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible also in cases where reactions without specific mentioning of protection and/or deprotection are described in this specification.

Within the scope of this disclosure only a readily removable group that is not a constituent of the particular desired end product of formula I is designated a "protecting group", unless the context indicates otherwise. The protection of functional groups by such protecting groups, the protecting groups themselves, and the reactions appropriate for their introduction and removal are described for example in standard reference works, such as J. F. W. McOmie, "Protective Groups in Organic Chemistry", Plenum Press, London and New York 1973, T. W. Greene and P. G. M. Wuts, "Protective Groups in Organic Synthesis", Third edition, Wiley, New York 1999, "The Peptides"; Volume 3 (editors: E. Gross and J. Meienhofer), Academic Press, London and New York 1981, "Methoden der organischen Chemie" (Methods of Organic Chemistry), Houben Weyl, 4th edition, Volume 15/I, Georg Thieme Verlag, Stuttgart 1974, H.-D. Jakubke and H. Jeschkeit, "Aminosaeuren, Peptide, Proteine" (Amino acids, Peptides, Proteins), Verlag Chemie, Weinheim, Deerfield Beach, and Basel 1982, and Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as N,N-dimethylformamide or N,N-dimethylacetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula I described as being preferred. Special preference is given to reaction conditions that are identical or analogous to those mentioned in Examples.

In one aspect, the present invention provides the process for preparing the compounds of formula (I), comprising
(1) reacting the compound of formula (II)

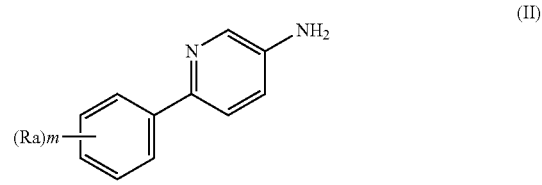

in which Ra and m are as defined above,
with nitrous acid or a salt or ester thereof with cooling to give the compound of formula (III)

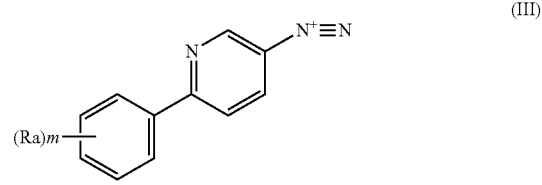

in which Ra and m are as defined above, (2) reacting the resulting compound of formula (III) with 4-amino-naphthalene-1-sulfonic acid under a basic condition to give the compound of formula (I), (3) isolating the resulting compound of formula (I) from the reaction mixture, and optionally, converting the compound of formula (I) into another compound of formula (I), converting the resulting salt of the compound of formula (I) into a free compound or another salt, converting the resulting free compound of formula (I) into a salt and/or ester thereof, and/or separating the resulting isomeric mixture of the compound of formula (I) into respective isomers.

Administration and Pharmaceutical Compositions

In other aspects, pharmaceutical compositions comprising at least one compound of formula (I) together with a pharmaceutically acceptable carrier suitable for administration to a human or animal subject, either alone or together with other agents are provided.

In another aspect, the compounds of formula (I) for treating glaucoma or retinitis pigmentosa and the use of the compounds of formula (I) in the preparation of a pharmaceutical for treating glaucoma or retinitis pigmentosa are provided.

In general, the compounds of the embodiments will be administered in a therapeutically effective amount by any of the accepted modes of administration for agents that serve similar utilities. The actual amount of the compound, i.e., the active ingredient, will depend upon numerous factors such as the severity of the disease to be treated, the age and relative health of the subject, the potency of the compound used, the route and form of administration, and other factors. The drug can be administered more than once a day, preferably three or four times a day. All of these factors are within the skill of the attending clinician.

The amount of active ingredient that may be combined with the carrier materials to produce a single dosage form will vary depending upon the host treated and the particular mode of administration. It will be understood, however, that the specific dose level for any particular subject will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

A therapeutically effective dose generally can be a total daily dose administered to a host in single or divided doses which may be in amounts, for example, of from about 0.001 to about 1000 mg/kg body weight daily and from about 1.0 to about 30 mg/kg body weight daily. Dosage unit compositions may contain such amounts of submultiples thereof to make up the daily dose.

The choice of formulation depends on various factors such as the mode of drug administration and bioavailability of the drug substance. The drug can be administered as pharmaceutical compositions by any one of the following routes or combination of two or more of them: oral, systemic (e.g., transdermal, intranasal or by suppository), topical (ophthalmic, intravitreal, subconjunctival, Tenon capsule or transdermal administration) or parenteral (e.g., intramuscular, intravenous or subcutaneous) administration, preferably oral, ophthalmic, intravitreal, subconjunctival or Tenon capsule administration. One manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another manner for administration is inhalation such as for delivering a therapeutic agent directly to the respiratory tract (see U.S. Pat. No. 5,607,915).

Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. In some embodiments liquid carriers, particularly for injectable solutions, include water, saline, aqueous dextrose, and glycols. Other suitable pharmaceutically acceptable excipients are described in "Remington's Pharmaceutical Sciences," Mack Pub. Co., New Jersey (1991).

As used herein, the term "pharmaceutically acceptable salts" refers to the nontoxic acid or alkaline earth metal salts of the compounds of formula (I). These salts can be prepared in situ during the final isolation and purification of the compounds of formula (I), or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with agents such as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl chlorides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the embodiments. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

It will be apparent to those skilled in the art that the compounds of formula (I) or the pharmaceutically acceptable salts, esters, oxides, and prodrugs of any of them, may be processed in vivo through metabolism in a human or animal body or cell to produce metabolites. The term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. The metabolites of a compound of the embodiments may be identified using routine techniques known in the art. See, e.g., Bertolini, G. et al., J. Med. Chem. 40:2011-2016 (1997); Shan, D. et al., J. Pharm. Sci. 86(7):765-767; Bagshawe K., Drug Dev. Res. 34:220-230 (1995); Bodor, N., Advances in Drug Res. 13:224-331 (1984); Bundgaard, H., Design of Prodrugs (Elsevier Press 1985); and Larsen, I. K., Design and Application of Prodrugs, Drug Design and Development (Krogsgaard-Larsen et al., eds., Harwood Academic Publishers, 1991). It should be understood that individual chemical compounds that are metabolites of the compounds of formula (I) or the pharmaceutically acceptable salts, esters, oxides and prodrugs of any of them, are included within the embodiments provided herein.

The compounds of the preferred embodiments may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices, or ocular administration including ophthalmic, intravitreal, subconjunctival or Tenon capsule administration. The term parenteral as used herein includes subcutaneous injections, intravenous, intrathecal, intramuscular, intrasternal injection, or infusion techniques.

Injectable preparations, for example, sterile injectable aqueous or oleaginous suspensions may be formulated according to the known art using suitable dispersing or wetting agents or suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the embodiments can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like. Examples of lipids are the phospholipids and phosphatidylcholines (lecithins), both natural and synthetic. Methods to form liposomes are known in the art. See, for example, Prescott, Ed., Methods in Cell Biology, Volume XIV, Academic Press, New York, N. W., p. 33 et seq. (1976).

Compressed gases may be used to disperse a compound of the embodiments in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

For delivery via inhalation the compound can be formulated as liquid solution, suspensions, aerosol propellants or dry powder and loaded into a suitable dispenser for administration. There are several types of pharmaceutical inhalation devices, nebulizer, inhalers, metered dose inhalers (MDI) and dry powder inhalers (DPI). Nebulizer devices produce a stream of high velocity air that causes the therapeutic agents (which are formulated in a liquid form) to spray as a mist that is carried into the subject's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the subject's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

The following Examples illustrate the present invention, but not limit the scope thereof.

EXAMPLES

Examples of Synthesis

Example 1

Synthesis of 4-amino-3-(6-phenylpyridine-3-ylazo)naphthalene-1-sulfonic acid sodium salt

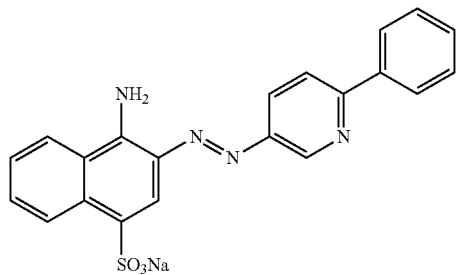

(i) 2-Phenyl-5-nitropyridine

2-Chloro-5-nitropyridine (3.0 g, 18.9 mmol), phenylboronic acid (2.5 g, 20.8 mmol), and tetrakis(triphenylphosphine)palladium (0.2 g, 0.2 mmol) were added to 1,2-dimethoxyethan (30 ml), then degassed and purged with nitrogen three times under reduced pressure. Under nitrogen atmosphere the mixture was stirred at room temperature for 20 minutes, then 1M aqueous sodium carbonate (40 ml) was poured in, and the temperature was raised to 80° C. After the reaction at 80° C. for 6 hours, the mixture was cooled to room temperature and crystallized with addition of water. The precipitated crystals were filtered to give the title compound (3.7 g, 96.8%).

(ii) 2-Phenyl-5-aminopyridine

Ethanol (20 ml) and water (5 ml) was mixed, added with iron powder, and heated to 70-80° C. Ammonium chloride (0.1 g, 2.1 mmol) was added, followed by 2-phenyl-5-nitropyridine (2.0 g, 10.0 mmol) obtained in (i). The reaction was carried out at 70-80° C. for 1 hour. After the completion of the reaction, the iron powder was filtered while hot through Celite, and the filtrate was concentrated under reduced pressure. The residue was dissolved in isopropyl alcohol, crystallized and filtered with addition of water to give the title compound (1.4 g, 81.9%).

(iii) 4-Amino-3-(6-phenylpyridine-3-ylazo)naphthalene-1-sulfonic acid sodium salt 2-Phenyl-5-aminopyridine (1.0 g, 5.9 mmol) obtained in (ii) was suspended in water, and added with 35% hydrochloric acid (2 ml) to form hydrochloride. With cooling on ice, an aqueous solution of sodium nitrite (0.4 g, 6.2 mmol) was added dropwise at 0 to 5° C., and the reaction was carried out for about 5 minutes. Amide sulfuric acid was added and the reaction was carried out for additional 5 minutes, resulting in diazo solution.

4-Amino-1-naphthalenesulfonic acid (1.3 g, 5.6 mmol) was suspended in water, and the pH of the suspension was adjusted to pH 8 to 9 with 10% aqueous sodium hydroxide. The mixture was cooled to 5-10° C., the obtained diazo solution was added dropwise at 5-10° C., during which 10% aqueous sodium hydroxide was added dropwise to keep the pH at 7 to 9. After the completion of the addition, the reaction was carried out at 5-10° C. for 1 hour, then the temperature was raised to room temperature. Saturated sodium chloride solution was added, and the precipitated crystals were filtered with suction. The products were purified by column chromatography to give the title compound (1.2 g, 48.3%).

$^1$H-NMR (DMSO-d6) δ[ppm]=9.21 (1H, d, J=2.7), 8.75 (1H, dd, J=8.6, 0.9), 8.55 (1H, dd, J=8.7, 2.7), 8.46 (1H, d, J=7.8), 8.31 (1H, s), 8.20 (2H, d, J=8.0), 8.12 (1H, d, J=8.7), 7.79 (2H, bs), 7.63-7.46 (5H, m)

$^{13}$C-NMR (DMSO-d6) δ[ppm]=155.9, 147.4, 147.2, 146.3, 138.1, 132.5, 132.1, 129.4, 129.3, 128.9, 128.5, 128.4, 127.6, 126.7, 125.1, 124.2, 124.0, 120.7, 116.3

Example 2

Synthesis of 4-amino-3-(6-p-tolylpyridine-3-ylazo)naphthalene-1-sulfonic acid sodium salt

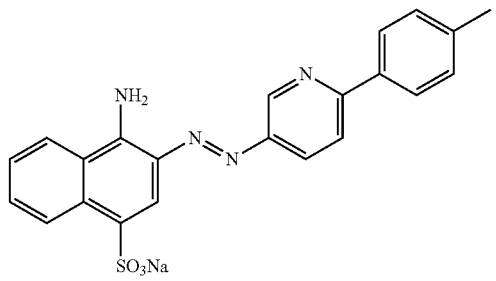

(i) 5-Nitro-2-p-tolylpyridine

2-Chloro-5-nitropyridine (5.0 g, 31.5 mmol) and tetrakis(triphenylphosphine)palladium (0.35 g, 0.3 mmol) were added to 1,2-dimethoxyethan (50 ml), then degassed and purged with nitrogen three times under reduced pressure. Under nitrogen atmosphere the mixture was stirred at room temperature for 20 minutes, 4-methylphenylboronic acid (4.29 g, 31.5 mmol) and 2M aqueous sodium carbonate (31.5 ml) were poured in, and the temperature was raised to 80° C. After the reaction at 80° C. for 3 hours, the mixture was cooled to room temperature and extracted with addition of ethyl acetate and water. The organic layer was dried with anhydrous sodium sulfate, and concentrated under reduced pressure. The products were purified by column chromatography to give the title compound (5.4 g, 80.0% yield).

(ii) 6-p-Tolylpyridine-3-ylamine

The title compound was synthesized in a manner analogous to Example 1 (ii), except for replacing 2-phenyl-5-nitropyridine with 5-nitro-2-p-tolylpyridine obtained in (i).

(iii) 4-Amino-3-(6-p-tolylpyridine-3-ylazo)naphthalene-1-sulfonic acid sodium salt The title compound was synthesized in a manner analogous to Example 1 (iii), except for replacing 2-phenyl-5-aminopyridine with 6-p-tolylpyridine-3-ylamine obtained in (ii).

$^1$H-NMR (DMSO-d6) δ[ppm]=9.20 (1H, d, J=2.4 Hz), 8.75 (1H, d, J=8.4 Hz), 8.45 (1H, d, J=8.7 Hz), 8.44 (1H, d, J=8.7 Hz), 8.29 (1H, s), 8.10 (2H, d, J=7.5 Hz), 8.07 (1H, d, J=7.8 Hz), 7.74 (2H, bs), 7.59 (1H, dd, J=7.5, 7.2 Hz), 7.47 (1H, dd, J=7.2 Hz), 7.33 (2H, d, J=8.1 Hz), 2.38 (3H, s)

$^{13}$C-NMR (DMSO-d6) δ[ppm]=155.9, 147.2, 146.9, 146.3, 139.0, 135.4, 132.6, 132.1, 129.5, 129.3, 128.4, 127.5, 126.6, 125.0, 124.2, 123.8, 120.2, 116.4, 20.9

Example 3

Synthesis of 4-amino-3-(6-m-tolylpyridine-3-ylazo)naphthalene-1-sulfonic acid sodium salt

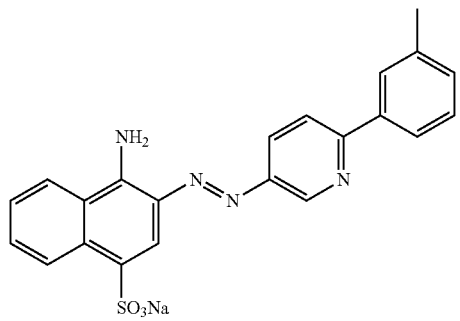

(i) 5-Nitro-2-m-tolylpyridine

The title compound was synthesized in a manner analogous to Example 1 (i), except for replacing phenylboronic acid with 3-methylphenylboronic acid.

(ii) 6-m-Tolylpyridine-3-ylamine

The title compound was synthesized in a manner analogous to Example 1 (ii), except for replacing 2-phenyl-5-nitropyridine with 5-nitro-2-m-tolylpyridine obtained in (i).

(iii) 4-Amino-3-(6-m-tolylpyridine-3-ylazo)naphthalene-1-sulfonic acid sodium salt The title compound was synthesized in a manner analogous to Example 1 (iii), except for replacing 2-phenyl-5-aminopyridine with 6-m-tolylpyridine-3-ylamine obtained in (ii).

$^1$H-NMR (DMSO-d6) δ[ppm]=9.22 (1H, dd, J=2.4, 0.6), 8.76 (1H, dd, J=8.4, 1.2), 8.46 (1H, d, J=8.7), 8.45 (1H, d, J=8.7), 8.31 (1H, s), 8.09 (1H, d, J=8.7), 8.03 (1H, s), 7.97 (1H, d, J=7.8), 7.77 (2H, bs), 7.56 (1H, m), 7.49 (1H, m), 7.40 (1H, dd, J=7.8, 7.5), 7.27 (1H, d, J=7.5), 2.42 (3H, s)

$^{13}$C-NMR (DMSO-d6) δ[ppm]=156.0, 147.3, 146.9, 146.2, 138.0, 132.6, 132.5, 132.1, 130.0, 129.3, 128.7, 128.4, 128.3, 127.4, 127.3, 125.0, 124.2, 123.9, 120.6, 116.5, 21.1

Example 4

Synthesis of 4-amino-3-(6-o-tolylpyridine-3-ylazo)naphthalene-1-sulfonic acid sodium salt

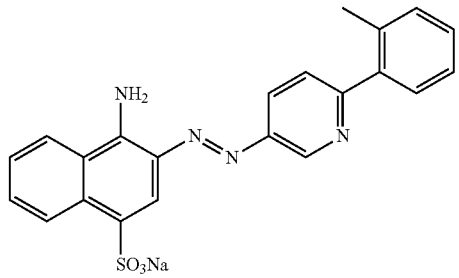

(i) 5-Nitro-2-o-tolylpyridine

The title compound was synthesized in a manner analogous to Example 2 (i), except for replacing 4-methylphenylboronic acid with 2-methylphenylboronic acid.

(ii) 6-o-Tolylpyridine-3-ylamine

The title compound was synthesized in a manner analogous to Example 1 (ii), except for replacing 2-phenyl-5-nitropyridine with 5-nitro-2-o-tolylpyridine obtained in (i).

(iii) 4-Amino-3-(6-o-tolylpyridine-3-ylazo)naphthalene-1-sulfonic acid sodium salt The title compound was synthesized in a manner analogous to Example 1 (iii), except for replacing 2-phenyl-5-aminopyridine with 6-o-tolylpyridine-3-ylamine obtained in (ii).

$^1$H-NMR (DMSO-d6) δ[ppm]=9.23 (1H, d, J=2.1 Hz), 8.76 (1H, d, J=8.1 Hz), 8.46 (1H, d, J=8.1 Hz), 8.45 (1H, dd, J=8.1, 2.1 Hz), 8.32 (1H, s), 7.78 (2H, bs), 7.66 (1H, d, J=8.1), 7.60 (1H, dd, J=7.8, 7.2), 7.52-7.48 (2H, m), 7.33-7.30 (3H, m), 2.41 (3H, s)

$^{13}$C-NMR (DMSO-d6) δ[ppm]=159.2, 147.0, 146.7, 145.3, 139.6, 135.6, 132.5, 132.1, 130.8, 129.7, 129.2, 128.5, 128.4, 128.3, 127.2, 125.9, 125.0, 124.5, 124.2, 123.9, 116.5, 20.4

Example 5

Synthesis of 4-amino-3-(6-biphenyl-2-ylpyridine-3-ylazo)naphthalene-1-sulfonic acid sodium salt

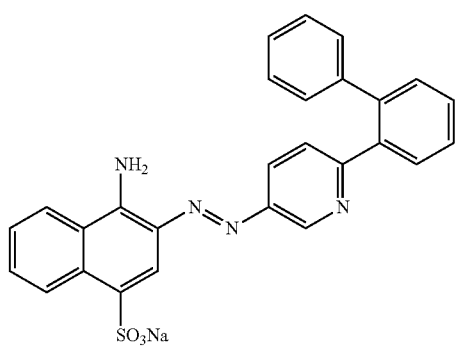

(i) 2-Biphenyl-2-yl-5-nitropyridine

The title compound was synthesized in a manner analogous to Example 1 (i), except for replacing phenylboronic acid with biphenyl-2-ylboronic acid.

(ii) 6-Biphenyl-2-ylpyridine-3-ylamine

To methanol (250 ml), 2-biphenyl-2-yl-5-nitropyridine (16.3 g, 58.9 mmol) obtained in (i) and 10% palladium carbon (1.2 g) were added, reduced at 45° C. under hydrogen pressure of 0.7 MPa. The palladium catalyst was filtered through Celite, and the filtrate was concentrated to dryness under reduced pressure to give title compound (16.6 g, 114.4% yield).

(iii) 4-Amino-3-(6-biphenyl-2-ylpyridine-3-ylazo) naphthalene-1-sulfonic acid sodium salt 6-Biphenyl-2-ylpyridine-3-ylamine (16.6 g, 58.9 mmol) obtained in (ii) was dissolved in 99% acetic acid (50 ml), and added with 35% hydrochloric acid (25 g) to form hydrochloride. With cooling on ice a 36% aqueous solution of sodium nitrite (12 g, 62.5 mmol) was added dropwise at 0-5° C., and the reaction was carried out for about 15 minutes. Amide sulfuric acid was added and the reaction was carried out for additional 5 minutes, resulting in diazo solution. 4-Amino-1-naphthalenesulfonic acid (13.0 g, 58.4 mmol) was suspended in water (130 ml), and the pH of the suspension was adjusted to pH 8 to 9 with 10% aqueous sodium hydroxide. The mixture was cooled to 5-10° C., and added dropwise with the obtained diazo solution at 5-10° C., during which 10% aqueous sodium hydroxide was added dropwise to keep the pH at 7 to 9. After the completion of the addition, the reaction was carried out at 5-10° C. for 1 hour, then the temperature was raised to room temperature. Salting-out was performed with saturated aqueous sodium chloride, and the precipitated crystals were filtered with suction. Purification by column chromatography gave the title compound (19.4 g, 66.1% yield).

$^1$H-NMR (DMSO-d6) δ[ppm]=9.14 (1H, d, J=2.4), 8.74 (1H, d, J=8.4), 8.45 (1H, d, J=7.8), 8.29 (1H, s), 8.17 (1H, dd, J=8.4, 2.4), 7.75-7.72 (3H, m), 7.62-7.44 (6H, m), 7.32-7.25 (1H, m), 7.29 (2H, d, J=7.2), 7.16 (2H, d, J=7.2), 7.03 (1H, d, J=8.4)

$^{13}$C-NMR (DMSO-d6) δ[ppm]=158.7, 147.2, 146.5, 146.3, 140.9, 140.3, 138.7, 132.3, 132.1, 130.5, 129.4, 129.2, 128.9, 128.5, 128.4, 128.3, 127.6, 127.0, 125.8, 125.4, 125.1, 124.2, 124.0, 116.2

Example 6

Synthesis of 3-[6-(2-acetylphenyl)pyridine-3-ylazo]-4-aminonaphthalene-1-sulfonic acid sodium salt

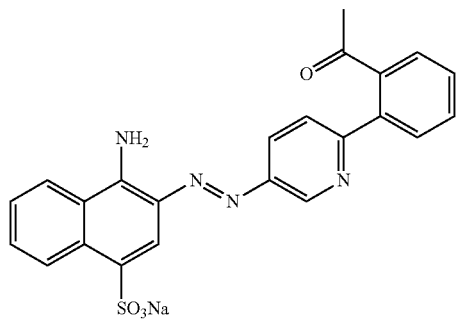

(i) (2-Acetylphenyl)-2-yl-5-nitropyridine

The title compound was synthesized in a manner analogous to Example 2 (i), except for replacing 4-methylphenylboronic acid with 2-acetylphenylboronic acid.

(ii) 6-(2-Acetylphenyl)pyridine-3-ylamine

The title compound was synthesized in a manner analogous to Example 1 (ii), except for replacing 2-phenyl-5-nitropyridine with (2-acetylphenyl)-2-yl-5-nitropyridine obtained in (i).

(iii) 3-[6-(2-Acetylphenyl)pyridine-3-ylazo]-4-aminonaphthalene-1-sulfonic acid sodium salt The title compound was synthesized in a manner analogous to Example 1 (iii), except for replacing 2-phenyl-5-aminopyridine with 6-(2-acetylphenyl)pyridine-3-ylamine obtained in (ii).

$^1$H-NMR (DMSO-d6) δ[ppm]=9.16 (1H, d, J=2.1 Hz), 8.75 (1H, d, J=7.8 Hz), 8.49 (1H, dd, J=8.7, 2.1 Hz), 8.46 (1H, m), 8.30 (1H, s), 7.94 (1H, d, J=8.7 Hz), 7.83 (1H, d, J=7.2 Hz), 7.82 (2H, bs), 7.64-7.50 (5H, m), 2.25 (3H, s)

$^{13}$C-NMR (DMSO-d6) δ[ppm]=203.1, 156.5, 147.2, 147.1, 144.8, 141.7, 137.6, 132.6, 132.2, 130.3, 129.3, 129.2, 128.9, 128.6, 128.4, 128.4, 127.4, 125.1, 124.2, 124.0, 123.0, 116.5, 30.5

Example 7

Synthesis of 3-[6-(3-acetylphenyl)pyridine-3-ylazo]-4-aminonaphthalene-1-sulfonic acid sodium salt

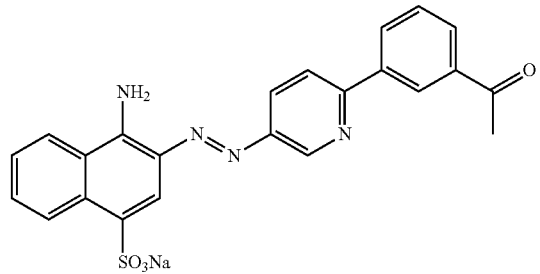

(i) (3-Acetylphenyl)-2-yl-5-nitropyridine

The title compound was synthesized in a manner analogous to Example 2 (i), except for replacing 4-methylphenylboronic acid with 3-acetylphenylboronic acid.

(ii) 6-(3-Acetylphenyl)pyridine-3-ylamine

The title compound was synthesized in a manner analogous to Example 1 (ii), except for replacing 2-phenyl-5-nitropyridine with (3-acetylphenyl)-2-yl-5-nitropyridine obtained in (i).

(iii) 3-[6-(3-Acetylphenyl)pyridine-3-ylazo]-4-aminonaphthalene-1-sulfonic acid sodium salt The title compound was synthesized in a manner analogous to Example 1 (iii), except for replacing 2-phenyl-5-aminopyridine with 6-(3-acetylphenyl)pyridine-3-ylamine obtained in (ii).

$^1$H-NMR (DMSO-d6) δ[ppm]=9.32 (1H, d, J=2.1 Hz), 8.82-8.78 (2H, m), 8.55 (1H, dd, J=8.7, 2.1 Hz), 8.54-8.50 (1H, m), 8.47 (1H, d, J=8.1 Hz), 8.38 (1H, s), 8.27 (1H, d, J=8.7 Hz), 8.08 (1H, d, J=8.1 Hz), 7.89 (2H, bs), 7.74-7.63 (2H, m), 7.58-7.53 (1H, m), 2.73 (3H, s)

$^{13}$C-NMR (DMSO-d6) δ[ppm]=198.0, 154.9, 147.6, 147.2, 146.4, 138.5, 137.5, 132.5, 132.2, 131.2, 129.4, 129.4, 128.9, 128.7, 128.3, 127.8, 126.3, 125.2, 124.2, 124.0, 121.1, 116.6, 27.0

Example 8

Synthesis of 3-[6-(4-acetylphenyl)pyridine-3-ylazo]-4-aminonaphthalenesulfonic acid sodium salt

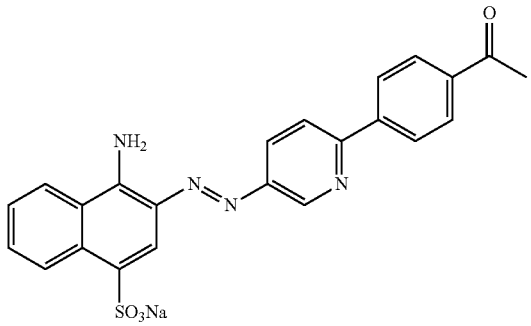

(i) (4-Acetylphenyl)-2-yl-5-nitropyridine

The title compound was synthesized in a manner analogous to Example 2 (i), except for replacing 4-methylphenylboronic acid with 4-acetylphenylboronic acid.

(ii) 6-(4-Acetylphenyl)pyridine-3-ylamine

The title compound was synthesized in a manner analogous to Example 1 (ii), except for replacing 2-phenyl-5-nitropyridine with (4-acetylphenyl)-2-yl-5-nitropyridine obtained in (i).

(iii) 3-[6-(4-Acetylphenyl)pyridine-3-ylazo]-4-aminonaphthalenesulfonic acid sodium salt The title compound was synthesized in a manner analogous to Example 1 (iii), except for replacing 2-phenyl-5-aminopyridine with 6-(4-acetylphenyl)pyridine-3-ylamine obtained in (ii).

$^1$H-NMR (DMSO-d6) δ[ppm]=9.27 (1H, d, J=2.1 Hz), 8.77 (1H, d, J=8.4 Hz), 8.51-8.46 (2H, m), 8.34-8.31 (3H, m), 8.20 (1H, d, J=8.7 Hz), 8.07 (2H, d, J=8.1 Hz), 7.87 (2H, bs), 7.50 (1H, dd, J=7.8, 7.2 Hz), 7.61 (1H, dd, J=7.8, 7.2 Hz), 2.62 (3H, s)

$^{13}$C-NMR (DMSO-d6) δ[ppm]=197.7, 154.5, 147.7, 147.3, 146.4, 142.1, 136.9, 132.4, 132.2, 129.4, 128.8, 128.3, 127.7, 126.8, 125.2, 124.2, 124.0, 121.5, 116.6, 26.9

Example 9

Synthesis of 4-amino-3-[6-(2,4-dichlorophenyl)pyridine-3-ylazo]naphthalene-1-sulfonic acid sodium salt

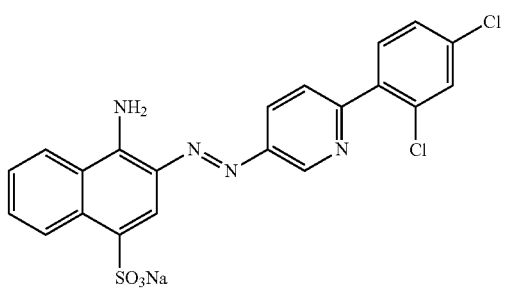

(i) 2-(2,4-Dichlorophenyl)-5-nitropyridine

The title compound was synthesized in a manner analogous to Example 1 (i), except for replacing phenylboronic acid with 2,4-dichlorophenylboronic acid.

(ii) 6-(2,4-Dichlorophenyl)pyridine-3-ylamine

The title compound was synthesized in a manner analogous to Example 1 (ii), except for replacing 2-phenyl-5-nitropyridine with 2-(2,4-dichlorophenyl)-5-nitropyridine obtained in (i).

(iii) 4-Amino-3-[6-(2,4-dichlorophenyl)pyridine-3-ylazo]naphthalene-1-sulfonic acid sodium salt The title compound was synthesized in a manner analogous to Example 1 (iii), except for replacing 2-phenyl-5-aminopyridine with 6-(2,4-dichlorophenyl)pyridine-3-ylamine obtained in (ii).

$^1$H-NMR (DMSO-d6) δ[ppm]=9.25 (1H, dd, J=2.4, 0.6 Hz), 8.75 (1H, dd, J=8.4, 0.9 Hz), 8.48 (1H, dd, J=8.4, 2.4 Hz), 8.46 (1H, d, J=8.1 Hz), 8.31 (1H, s), 7.85 (2H, bs), 7.82 (1H, dd, J=8.4, 0.6 Hz), 7.76 (1H, d, J=2.4 Hz), 7.72 (1H, d, J=8.1 Hz), 7.57 (1H, dd, J=8.1, 2.4 Hz), 7.63-7.59 (1H, m), 7.53-7.50 (1H, m)

$^{13}$C-NMR (DMSO-d6) δ[ppm]=154.8, 147.4, 145.8, 137.4, 134.0, 133.1, 132.5, 132.3, 132.2, 129.5, 129.3, 128.7, 128.3, 127.7, 127.1, 125.2, 124.2, 124.0, 116.6

Example 10

Synthesis of 4-amino-3-[6-(2-trifluoromethylphenyl)pyridine-3-ylazo]naphthalene-1-sulfonic acid sodium salt

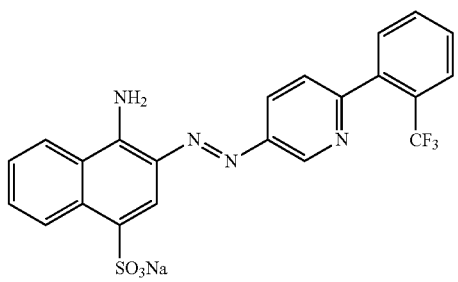

(i) 5-Nitro-2-(2-trifluoromethylphenyl)pyridine

The title compound was synthesized in a manner analogous to Example 2 (i), except for replacing 4-methylphenylboronic acid with 2-trifluoromethylphenylboronic acid.

(ii) 6-(2-Trifluoromethylphenyl)pyridine-3-ylamine

The title compound was synthesized in a manner analogous to Example 1 (ii), except for replacing 2-phenyl-5-nitropyridine with 5-nitro-2-(2-trifluoromethylphenyl)pyridine obtained in (i).

(iii) 4-Amino-3-[6-(2-trifluoromethylphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2-trifluoromethylphenyl)pyridine-3-ylamine obtained in (ii).

$^1$H-NMR (DMSO-d6) δ[ppm]=9.23 (1H, d, J=1.8 Hz), 8.77 (1H, d, J=8.1 Hz), 8.49 (1H, d, J=8.4 Hz), 8.48 (1H, d, J=8.1 Hz), 8.34 (1H, s), 7.89-7.48 (9H, m)

$^{13}$C-NMR (DMSO-d6) δ[ppm]=157.2, 147.3, 145.1, 139.4, 132.4, 132.3, 132.2, 131.7, 129.3, 129.0, 128.6, 128.3, 127.3, 127.1, 126.7, 126.5, 126.4, 126.0, 125.1, 124.3, 124.2, 124.0, 122.4, 116.5

Example 11

Synthesis of 4-amino-3-[6-(4-trifluoromethylphenyl)pyridine-3-ylazo]naphthalene-1-sulfonic acid sodium salt

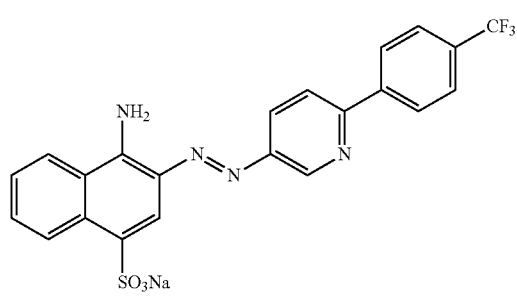

(i) 5-Nitro-2-(4-trifluoromethylphenyl)pyridine

The title compound was synthesized in a manner analogous to Example 2 (i), except for replacing 4-methylphenylboronic acid with 4-trifluoromethylphenylboronic acid.

(ii) 6-(4-Trifluoromethylphenyl)pyridine-3-ylamine

The title compound was synthesized in a manner analogous to Example 1 (ii), except for replacing 2-phenyl-5-nitropyridine with 5-nitro-2-(4-trifluoromethylphenyl)pyridine obtained in (i).

(iii) 4-Amino-3-[6-(4-trifluoromethylphenyl)pyridine-3-ylazo]naphthalene-1-sulfonic acid sodium salt The title compound was synthesized in a manner analogous to Example 1 (iii), except for replacing 2-phenyl-5-aminopyridine with 6-(4-trifluoromethylphenyl)pyridine-3-ylamine obtained in (ii).

$^1$H-NMR (DMSO-d6) δ[ppm]=9.27 (1H, d, J=2.4 Hz), 8.77 (1H, dd, J=8.4, 1.2 Hz), 8.51 (1H, dd, J=8.4, 2.4 Hz), 8.46 (1H, d, J=8.1 Hz), 8.40 (2H, d, J=8.1 Hz), 8.33 (1H, s), 8.21 (1H, d, J=8.4 Hz), 7.86 (2H, d, J=8.1 Hz), 7.85 (2H, bs), 7.63-7.58 (1H, m), 7.53-7.47 (1H, m)

$^{13}$C-NMR (DMSO-d6) δ[ppm]=154.0, 147.8, 147.2, 146.2, 141.9, 132.6, 132.2, 129.4, 129.0, 128.6, 128.3, 127.8, 127.3, 125.7, 125.6, 125.0, 124.2, 123.9, 121.4, 116.6

Example 12

Synthesis of 4-amino-3-[6-(2-chlorophenyl)pyridine-3-ylazo]naphthalene-1-sulfonic acid sodium salt

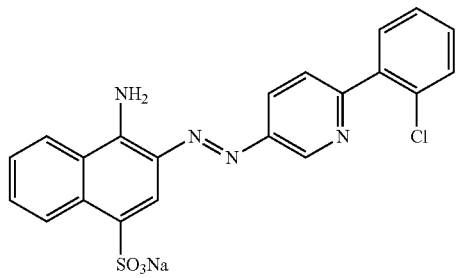

(i) 2-(2-Chlorophenyl)-5-nitropyridine

The title compound was synthesized in a manner analogous to Example 1 (i), except for replacing phenylboronic acid with 2-chlorophenylboronic acid.

(ii) 6-(2-Chlorophenyl)pyridine-3-ylamine

The title compound was synthesized in a manner analogous to Example 1 (ii), except for replacing 2-phenyl-5-nitropyridine with 2-(2-chlorophenyl)-5-nitropyridine obtained in (i).

(iii) 4-Amino-3-[6-(2-chlorophenyl)pyridine-3-ylazo]naphthalene-1-sulfonic acid sodium salt The title compound was synthesized in a manner analogous to Example 1 (iii), except for replacing 2-phenyl-5-aminopyridine with 6-(2-chlorophenyl)pyridine-3-ylamine obtained in (ii).

$^1$H-NMR (DMSO-d6) δ[ppm]=8.76 (1H, d, J=2.4 Hz), 8.27 (1H, d, J=8.4 Hz), 7.99 (1H, dd, J=8.4, 2.4 Hz), 7.96 (1H, d, J=8.4 Hz), 7.83 (1H, s), 7.33 (2H, bs), 7.32 (1H, d, J=8.4 Hz), 7.20-7.18 (1H, m), 7.14-7.09 (2H, m), 7.03-6.97 (3H, m)

$^{13}$C-NMR (DMSO-d6) δ[ppm]=155.8, 147.3, 147.2, 145.7, 138.4, 132.4, 132.2, 131.7, 131.2, 130.2, 130.1, 129.3, 128.6, 128.3, 127.4, 126.7, 125.1, 124.2, 124.0, 116.5

Example 13

Synthesis of 4-amino-3-[6-(3-chlorophenyl)pyridine-3-ylazo]naphthalene-1-sulfonic acid sodium salt

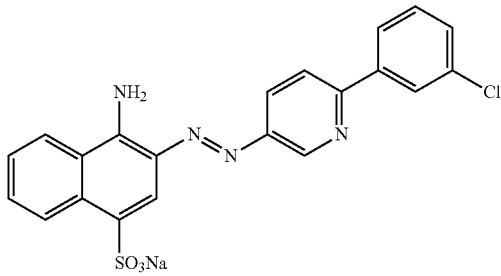

(i) 2-(3-Chlorophenyl)-5-nitropyridine

The title compound was synthesized in a manner analogous to Example 1 (i), except for replacing phenylboronic acid with 3-chlorophenylboronic acid.

(ii) 6-(3-Chlorophenyl)pyridine-3-ylamine

The title compound was synthesized in a manner analogous to Example 1 (ii), except for replacing 2-phenyl-5-nitropyridine with 2-(3-chlorophenyl)-5-nitropyridine obtained in (i).

(iii) 4-Amino-3-[6-(3-chlorophenyl)pyridine-3-ylazo]naphthalene-1-sulfonic acid sodium salt The title compound was synthesized in a manner analogous to Example 1 (iii), except for replacing 2-phenyl-5-aminopyridine with 6-(3-chlorophenyl)pyridine-3-ylamine obtained in (ii).

$^1$H-NMR (DMSO-d6) δ[ppm]=9.24 (1H, d, J=2.4 Hz), 8.76 (1H, d, J=8.4 Hz), 8.49 (1H, dd, J=8.4, 2.4 Hz), 8.47 (1H, d, J=6.9 Hz), 8.33 (1H, s), 8.24 (1H, d, J=2.1 Hz), 8.17 (1H, d, J=8.4 Hz), 8.17-8.14 (1H, m), 7.84 (2H, bs), 7.63-7.57 (1H, m), 7.55-7.47 (3H, m)

$^{13}$C-NMR (DMSO-d6) δ[ppm]=154.1, 147.7, 147.2, 146.3, 140.1, 133.8, 132.5, 132.1, 130.7, 129.4, 129.0, 128.6, 128.3, 127.7, 126.3, 125.2, 125.1, 124.2, 124.0, 121.1, 116.5

Example 14

Synthesis of 4-amino-3-[6-(4-chlorophenyl)pyridine-3-ylazo]naphthalene-1-sulfonic acid sodium salt

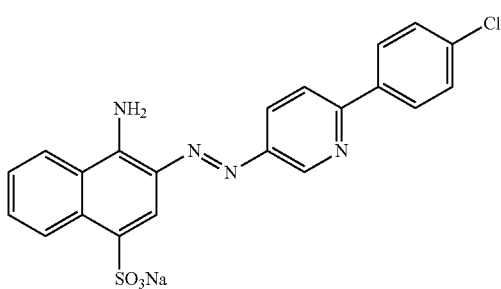

(i) 2-(4-Chlorophenyl)-5-nitropyridine

The title compound was synthesized in a manner analogous to Example 1 (i), except for replacing phenylboronic acid with 4-chlorophenylboronic acid.

(ii) 6-(4-Chlorophenyl)pyridine-3-ylamine

The title compound was synthesized in a manner analogous to Example 1 (ii), except for replacing 2-phenyl-5-nitropyridine with 2-(4-chlorophenyl)-5-nitropyridine obtained in (i).

(iii) 4-Amino-3-[6-(4-chlorophenyl)pyridine-3-ylazo]naphthalene-1-sulfonic acid sodium salt The title compound was synthesized in a manner analogous to Example 1 (iii), except for replacing 2-phenyl-5-aminopyridine with 6-(4-chlorophenyl)pyridine-3-ylamine obtained in (ii).

$^1$H-NMR (DMSO-d6) δ[ppm]=9.18 (1H, d, J=1.8 Hz), 8.70 (1H, d, J=8.1 Hz), 8.06 (1H, d, J=8.4 Hz), 8.45-8.40 (2H, m), 8.28 (1H, s), 8.16 (2H, d, J=8.4 Hz), 7.78 (2H, bs), 7.58-7.42 (4H, m)

$^{13}$C-NMR (DMSO-d6) δ[ppm]=154.6, 147.5, 147.4, 146.5, 136.9, 134.2, 132.4, 132.2, 129.3, 128.9, 128.7, 128.5, 128.3, 127.7, 125.2, 124.2, 124.1, 120.8, 116.4

Example 15

Synthesis of 4-amino-3-[6-(2-methoxyphenyl)pyridine-3-ylazo]naphthalene-1-sulfonic acid sodium salt

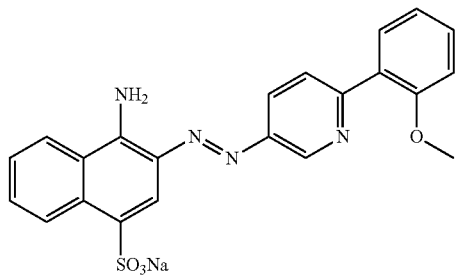

(i) 2-(2-Methoxyphenyl)-5-nitropyridine

The title compound was synthesized in a manner analogous to Example 1 (i), except for replacing phenylboronic acid with 2-methoxyphenylboronic acid.

(ii) 6-(2-Methoxyphenyl)pyridine-3-ylamine

The title compound was synthesized in a manner analogous to Example 1 (ii), except for replacing 2-phenyl-5-nitropyridine with 2-(2-methoxyphenyl)-5-nitropyridine obtained in (i).

(iii) 4-Amino-3-[6-(2-methoxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2-methoxyphenyl)pyridine-3-ylamine obtained in (ii).

¹H-NMR (DMSO-d6) δ[ppm]=9.23 (1H, d, J=2.1 Hz), 8.76 (1H, dd, J=8.4, 2.1 Hz), 8.46 (1H, d, J=8.4 Hz), 8.40 (1H, dd, J=8.4, 1.8 Hz), 8.33 (1H, s), 8.03 (1H, d, J=8.4 Hz), 7.88 (1H, dd, J=7.8, 1.8 Hz), 7.76 (2H, bs), 7.63-7.58 (1H, m), 7.52-7.47 (1H, m), 7.46-7.40 (1H, m), 7.18 (1H, d, J=8.1 Hz), 7.12-7.07 (1H, m), 3.87 (3H, s)

¹³C-NMR (DMSO-d6) δ[ppm]=157.0, 155.2, 146.9, 146.7, 145.8, 132.4, 132.0, 130.7, 130.5, 129.2, 128.4, 128.3, 127.7, 126.4, 125.1, 124.2, 123.9, 120.7, 116.5, 112.1, 55.7

Example 16

Synthesis of 4-amino-3-[6-(4-methoxyphenyl)pyridine-3-ylazo]naphthalene-1-sulfonic acid sodium salt

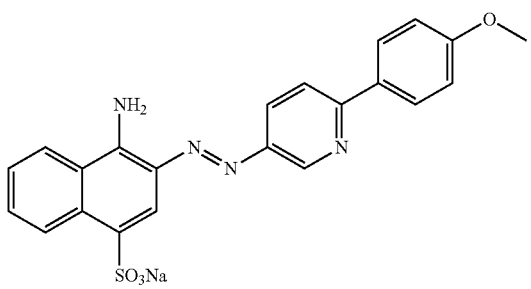

(i) 2-(4-Methoxyphenyl)-5-nitropyridine

The title compound was synthesized in a manner analogous to Example 1 (i), except for replacing phenylboronic acid with 4-methoxyphenylboronic acid.

(ii) 6-(4-Methoxyphenyl)pyridine-3-ylamine

The title compound was synthesized in a manner analogous to Example 1 (ii), except for replacing 2-phenyl-5-nitropyridine with 2-(4-methoxyphenyl)-5-nitropyridine obtained in (i).

(iii) 4-Amino-3-[6-(4-methoxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(4-methoxyphenyl)pyridine-3-ylamine obtained in (ii).

¹H-NMR (DMSO-d6) δ[ppm]=9.19 (1H, d, J=2.1 Hz), 8.75 (1H, dd, J=8.1, 0.9 Hz), 8.47-8.42 (2H, m), 8.32 (1H, s), 8.16 (2H, d, J=9.0 Hz), 8.04 (1H, d, J=8.7 Hz), 7.75 (2H, bs), 7.63-7.57 (1H, m), 7.52-7.47 (1H, m), 7.06 (2H, d, J=9.0 Hz), 3.82 (3H, s)

¹³C-NMR (DMSO-d6) δ[ppm]=160.5, 155.8, 146.9, 146.8, 146.5, 132.4, 132.0, 130.6, 129.3, 128.4, 128.3, 128.2, 127.4, 125.1, 124.2, 123.9, 119.8, 116.3, 114.3, 55.3

Example 17

Synthesis of 4-amino-3-[6-(2-isopropoxyphenyl)pyridine-3-ylazo]naphthalene-1-sulfonic acid sodium salt

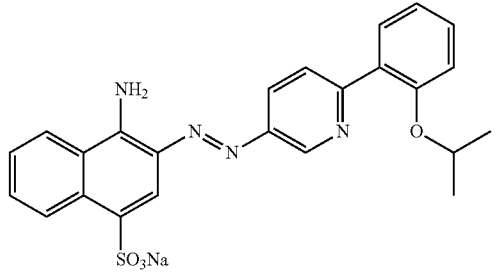

(i) 2-(2-Isopropoxyphenyl)-5-nitropyridine

The title compound was synthesized in a manner analogous to Example 1 (i), except for replacing phenylboronic acid with 2-isopropoxyphenylboronic acid.

(ii) 6-(2-Isopropoxyphenyl)pyridine-3-ylamine

The title compound was synthesized in a manner analogous to Example 1 (ii), except for replacing 2-phenyl-5-nitropyridine with 2-(2-isopropoxyphenyl)-5-nitropyridine obtained in (i).

(iii) 4-Amino-3-[6-(2-isopropoxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2-isopropoxyphenyl)pyridine-3-ylamine obtained in (ii).

¹H-NMR (DMSO-d6) δ[ppm]=9.23 (1H, d, J=2.1 Hz), 8.77 (1H, d, J=8.4 Hz), 8.52-8.45 (2H, m), 8.36 (1H, s), 8.10 (1H, d, J=8.7 Hz), 7.90 (1H, dd, J=7.5, 1.2 Hz), 7.82 (2H, bs), 7.64-7.58 (1H, m), 7.52-7.48 (1H, m), 7.41-7.35 (1H, m), 7.14 (1H, d, J=8.4 Hz), 7.08-7.03 (1H, m), 4.72-4.65 (1H, m), 1.28 (6H, d, J=6.0 Hz)

¹³C-NMR (DMSO-d6) δ[ppm]=155.4, 155.2, 147.2, 146.7, 146.5, 132.4, 132.1, 131.1, 130.4, 129.2, 128.5, 128.4, 128.3, 125.7, 125.2, 125.1, 124.2, 123.9, 120.6, 116.2, 114.5, 70.1, 21.9

Example 18

Synthesis of 4-amino-3-[6-(4-isopropoxyphenyl)pyridine-3-ylazo]naphthalene-1-sulfonic acid sodium salt

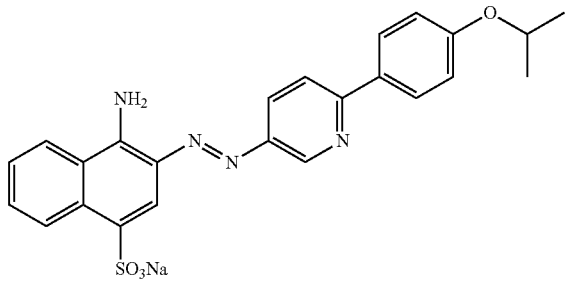

(i) 2-(4-Isopropoxyphenyl)-5-nitropyridine

The title compound was synthesized in a manner analogous to Example 1 (i), except for replacing phenylboronic acid with 4-isopropoxyphenylboronic acid.

(ii) 6-(4-Isopropoxyphenyl)pyridine-3-ylamine

The title compound was synthesized in a manner analogous to Example 1 (ii), except for replacing 2-phenyl-5-nitropyridine with 2-(4-isopropoxyphenyl)-5-nitropyridine obtained in (i).

(iii) 4-Amino-3-[6-(4-isopropoxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(4-isopropoxyphenyl)pyridine-3-ylamine obtained in (ii).

$^1$H-NMR (DMSO-d6) δ[ppm]=9.17 (1H, dd, J=2.4, 0.6 Hz), 8.77 (1H, dd, J=8.4, 1.2 Hz), 8.45 (1H, d, J=8.4 Hz), 8.41 (1H, dd, J=8.7, 2.4 Hz), 8.33 (1H, s), 8.12 (2H, d, J=9.0 Hz), 8.01 (1H, d, J=8.7 Hz), 7.74 (2H, bs), 7.62-7.57 (1H, m), 7.52-7.47 (1H, m), 7.02 (2H, d, J=9.0 Hz), 4.73-4.65 (1H, m), 1.29 (6H, d, J=5.7 Hz)

$^{13}$C-NMR (DMSO-d6) δ[ppm]=158.7, 155.8, 146.7, 146.6, 146.2, 132.5, 132.0, 130.2, 129.2, 128.3, 128.2, 127.4, 124.9, 124.2, 123.8, 119.6, 116.6, 115.7, 69.3, 21.8

Example 19

Synthesis of 4-amino-3-[6-(2-phenoxyphenyl)pyridine-3-ylazo]naphthalene-1-sulfonic acid sodium salt

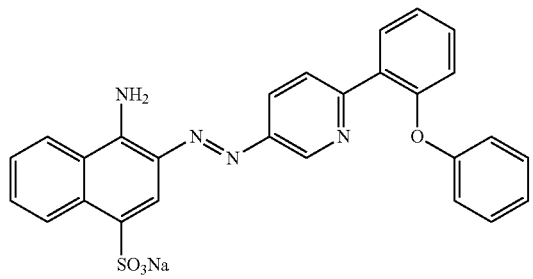

(i) 5-Nitro-2-(2-phenoxyphenyl)pyridine

The title compound was synthesized in a manner analogous to Example 2 (i), except for replacing 4-methylphenylboronic acid with 2-phenoxyphenylboronic acid.

(ii) 6-(2-Phenoxyphenyl)pyridine-3-ylamine

The title compound was synthesized in a manner analogous to Example 1 (ii), except for replacing 2-phenyl-5-nitropyridine with 5-nitro-2-(2-phenoxyphenyl)pyridine obtained in (i).

(iii) 4-Amino-3-[6-(2-phenoxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2-phenoxyphenyl)pyridine-3-ylamine obtained in (ii).

$^1$H-NMR (DMSO-d6) δ[ppm]=9.23 (1H, d, J=2.1 Hz), 8.74 (1H, d, J=8.4 Hz), 8.45 (1H, d, J=8.4 Hz), 8.40 (1H, dd, J=8.7, 2.1 Hz), 8.30 (1H, s), 8.03 (1H, dd, J=7.5, 1.5 Hz), 7.97 (1H, d, J=8.7), 7.75 (2H, bs), 7.62-7.57 (1H, m), 7.51-7.44 (2H, m), 7.38-7.33 (3H, m), 7.10-6.98 (4H, m)

$^{13}$C-NMR (DMSO-d6) δ[ppm]=157.0, 154.3, 153.7, 147.5, 147.1, 146.5, 132.4, 132.2, 131.4, 131.1, 130.8, 130.2, 129.2, 128.6, 128.4, 126.6, 125.2, 124.7, 124.5, 124.2, 124.0, 123.2, 120.3, 117.9, 116.0

Example 20

Synthesis of 4-amino-3-[6-(3-methoxyphenyl)pyridine-3-ylazo]naphthalene-1-sulfonic acid sodium salt

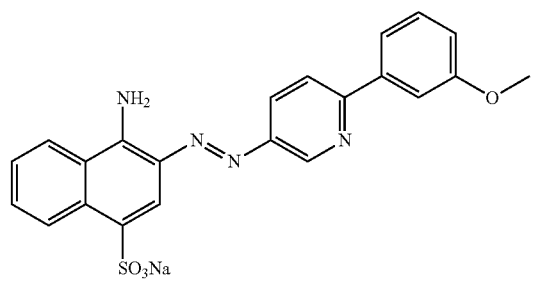

(i) 2-(3-Methoxyphenyl)-5-nitropyridine

The title compound was synthesized in a manner analogous to Example 2 (i), except for replacing 4-methylphenylboronic acid with 3-methoxyphenylboronic acid.

(ii) 6-(3-Methoxyphenyl)pyridine-3-ylamine

The title compound was synthesized in a manner analogous to Example 1 (ii), except for replacing 2-phenyl-5-nitropyridine with 2-(3-methoxyphenyl)-5-nitropyridine obtained in (i).

(iii) 4-Amino-3-[6-(3-methoxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(3-methoxyphenyl)pyridine-3-ylamine obtained in (ii).

$^1$H-NMR (DMSO-d6) δ[ppm]=9.23 (1H, d, J=2.4 Hz), 8.78 (1H, dd, J=8.4, 1.2 Hz), 8.47 (1H, d, J=8.1 Hz), 8.45 (1H, dd, J=8.7, 2.4 Hz), 8.35 (1H, s), 8.11 (1H, d, J=8.7 Hz), 7.76-7.74 (4H, m), 7.63-7.58 (1H, m), 7.53-7.47 (1H, m), 7.24 (1H, dd, J=8.1 Hz), 7.05-7.01 (1H, m), 3.86 (3H, s)

$^{13}$C-NMR (DMSO-d6) δ[ppm]=159.7, 155.6, 147.4, 146.9, 146.0, 139.5, 132.5, 132.1, 129.9, 129.3, 128.5, 128.3, 127.6, 125.0, 124.2, 123.9, 120.8, 119.0, 116.6, 115.2, 111.7, 55.2

Example 21

Synthesis of 4-amino-3-[6-(2,3-dimethylphenyl)pyridine-3-ylazo]naphthalene-1-sulfonic acid sodium salt

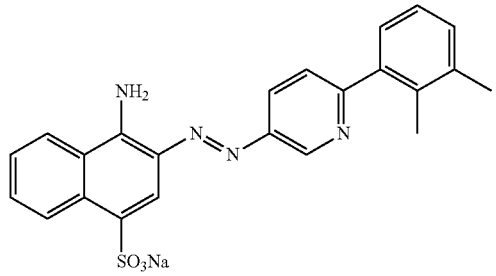

(i) 2-(2,3-Dimethylphenyl)-5-nitropyridine

The title compound was synthesized in a manner analogous to Example 2 (i), except for replacing 4-methylphenylboronic acid with 2,3-dimethylphenylboronic acid.

(ii) 6-(2,3-Dimethylphenyl)pyridine-3-ylamine

The title compound was synthesized in a manner analogous to Example 1 (ii), except for replacing 2-phenyl-5-nitropyridine with 2-(2,3-dimethylphenyl)-5-nitropyridine obtained in (i).

(iii) 4-Amino-3-[6-(2,3-dimethylphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2,3-dimethylphenyl)pyridine-3-ylamine obtained in (ii).

$^1$H-NMR (DMSO-d6) δ[ppm]=9.23 (1H, d, J=2.1 Hz), 8.77 (1H, d, J=8.1 Hz), 8.48-8.43 (2H, m), 8.35 (1H, s), 7.79 (2H, bs), 7.63-7.57 (2H, m), 7.53-7.48 (1H, m), 7.28-7.16 (3H, m), 2.32 (3H, s), 2.23 (3H, s)

$^{13}$C-NMR (DMSO-d6) δ[ppm]=160.0, 147.0, 146.7, 145.3, 140.2, 137.1, 134.1, 132.4, 132.1, 129.8, 129.2, 128.5, 128.3, 127.5, 127.0, 125.3, 125.1, 124.8, 124.2, 123.9, 116.6, 20.2, 16.6

Example 22

Synthesis of 4-amino-3-[6-(2,5-dimethylphenyl)pyridine-3-ylazo]naphthalene-1-sulfonic acid sodium salt

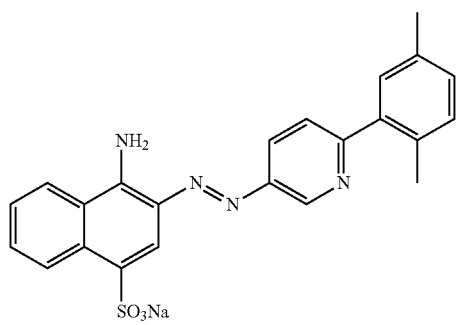

(i) 2-(2,5-Dimethylphenyl)-5-nitropyridine

The title compound was synthesized in a manner analogous to Example 2 (i), except for replacing 4-methylphenylboronic acid with 2,5-dimethylphenylboronic acid.

(ii) 6-(2,5-Dimethylphenyl)pyridine-3-ylamine

The title compound was synthesized in a manner analogous to Example 1 (ii), except for replacing 2-phenyl-5-nitropyridine with 2-(2,5-dimethylphenyl)-5-nitropyridine obtained in (i).

(iii) 4-Amino-3-[6-(2,5-dimethylphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2,5-dimethylphenyl)pyridine-3-ylamine obtained in (ii).

$^1$H-NMR (DMSO-d6) δ[ppm]=9.22 (1H, d, J=2.1 Hz), 8.75 (1H, dd, J=8.4, 1.2 Hz), 8.46 (1H, d, J=8.4 Hz), 8.45 (1H, d, J=8.4 Hz), 8.32 (1H, s), 7.78 (2H, bs), 7.65 (1H, d, J=8.4 Hz), 7.63-7.58 (1H, m), 7.52-7.47 (1H, m), 7.31 (1H, s), 7.21 (1H, d, J=7.8 Hz), 7.14 (1H, dd, J=7.8, 1.2 Hz), 2.35 (3H, s), 2.33 (3H, s)

$^{13}$C-NMR (DMSO-d6) δ[ppm]=159.4, 147.1, 146.7, 145.5, 139.4, 134.9, 132.4, 132.4, 132.1, 130.8, 130.3, 129.2, 129.1, 128.5, 128.3, 127.1, 125.1, 124.5, 124.2, 123.9, 116.4, 20.6, 20.0

Example 23

Synthesis of 4-amino-3-[6-(3,5-dimethylphenyl)pyridine-3-ylazo]naphthalene-1-sulfonic acid sodium salt

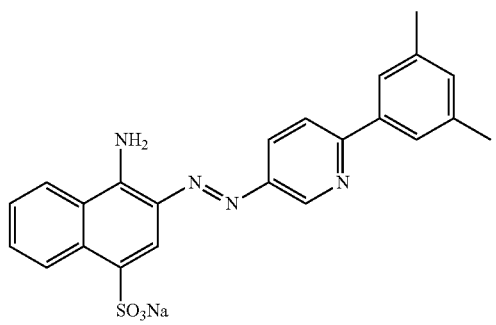

(i) 2-(3,5-Dimethylphenyl)-5-nitropyridine

The title compound was synthesized in a manner analogous to Example 1 (i), except for replacing phenylboronic acid with 3,5-dimethylphenylboronic acid.

(ii) 6-(3,5-Dimethylphenyl)pyridine-3-ylamine

The title compound was synthesized in a manner analogous to Example 1 (ii), except for replacing 2-phenyl-5-nitropyridine with 2-(3,5-dimethylphenyl)-5-nitropyridine obtained in (i).

(iii) 4-Amino-3-[6-(3,5-dimethylphenyl)pyridine-3-ylazo]naphthalene-1-sulfonic acid sodium salt The title compound was synthesized in a manner analogous to Example 1 (iii), except for replacing 2-phenyl-5-aminopyridine with 6-(3,5-dimethylphenyl)pyridine-3-ylamine obtained in (ii).

$^1$H-NMR (DMSO-d6) δ[ppm]=9.21 (1H, d, J=2.4 Hz), 8.76 (1H, d, J=7.8 Hz), 8.47-8.44 (2H, m), 8.33 (1H, s), 8.07 (1H, d, J=8.7), 7.81 (4H, s), 7.63-7.58 (1H, m), 7.53-7.48 (1H, m), 7.09 (1H, s), 2.37 (6H, s)

$^{13}$C-NMR (DMSO-d6) δ[ppm]=156.1, 147.3, 146.9, 146.4, 138.0, 137.9, 132.5, 132.1, 130.8, 129.3, 128.5, 128.3, 127.2, 125.1, 124.5, 124.2, 123.9, 120.6, 116.6, 21.1

Example 24

Synthesis of 4-amino-3-[6-(3-trifluoromethylphenyl)pyridine-3-ylazo]naphthalene-1-sulfonic acid sodium salt

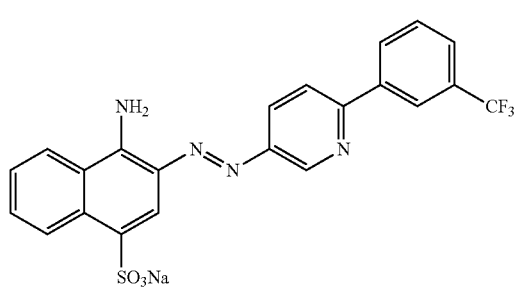

(i) 5-Nitro-2-(3-trifluoromethylphenyl)pyridine

The title compound was synthesized in a manner analogous to Example 2 (i), except for replacing 4-methylphenylboronic acid with 3-trifluoromethylphenylboronic acid.

(ii) 6-(3-Trifluoromethylphenyl)pyridine-3-ylamine

The title compound was synthesized in a manner analogous to Example 1 (ii), except for replacing 2-phenyl-5-nitropyridine with 5-nitro-2-(3-trifluoromethylphenyl)pyridine obtained in (i).

(iii) 4-Amino-3-[6-(3-trifluoromethylphenyl)pyridine-3-ylazo]naphthalene-1-sulfonic acid sodium salt The title compound was synthesized in a manner analogous to Example 1 (iii), except for replacing 2-phenyl-5-aminopyridine with 6-(3-trifluoromethylphenyl)pyridine-3-ylamine obtained in (ii).

$^1$H-NMR (DMSO-d6) δ[ppm]=9.27 (1H, d, J=2.4 Hz), 8.77 (1H, d, J=7.2 Hz), 8.53-8.47 (4H, m), 8.35 (1H, s), 7.87 (2H, bs), 7.81 (1H, d, J=7.8 Hz), 7.75 (1H, dd, J=7.8 Hz), 7.64-7.58 (1H, m), 7.53-7.48 (1H, m)

$^{13}$C-NMR (DMSO-d6) δ[ppm]=153.9, 147.8, 147.3, 146.4, 139.0, 132.5, 132.2, 130.5, 130.1, 130.0, 129.6, 129.4, 128.6, 128.3, 127.8, 126.1, 125.7, 125.1, 124.2, 124.0, 123.0, 122.9, 122.5, 121.2, 116.6, 62.0

Example 25

Synthesis of methyl 4-{4-[5-(1-amino-4-sulfonaphthalene-2-ylazo)pyridine-2-yl]phenyl}-4-oxobutyrate sodium salt

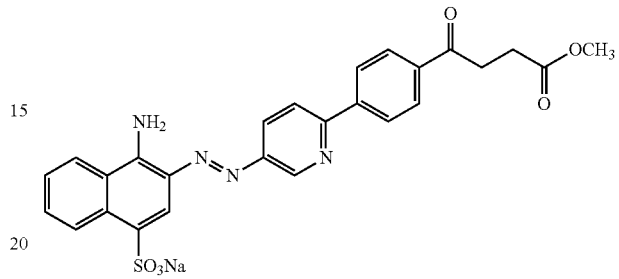

(i) Methyl 4-(4-bromophenyl)-4-oxobutyrate

To a solution of 4-(4-bromophenyl)-4-oxobutylic acid (5.0 g, 19.4 mmol) in methanol (40 ml) trimethyl orthoformate (4 ml) and 98% sulfuric acid (0.5 g) was added and refluxed with heating. After the completion of the reaction and the concentration under reduced pressure, the products were crystallized with addition of water. The resulting crystals were filtered with suction to give the title compound (4.13 g, 97.9%).

(ii) Methyl 4-oxo-4-[4-(4,4,5,5-tetramethyl-[1,3,2]dioxaborolane-2-yl)phenyl]butyrate To a solution of methyl 4-(4-bromophenyl)-4-oxobutyrate (0.54 g, 2.0 mmol) obtained in (i) and [1,1'-bis(diphenylphosphino)ferrocene]palladium(II) dichloride (0.05 g, 0.06 mmol) in dimethylsulfoxide, bis(pinacolato)diborane (0.51 g, 2.0 mmol) and potassium acetate (0.6 g, 6.0 mmol) were added, and reacted under nitrogen at 80° C. for 1 hour. After cooling, water was added and the mixture was extracted with ethyl acetate. The organic layer was washed with aqueous sodium chloride, concentrated under reduced pressure, and purified by column chromatography to give the title compound (0.67 g, 105.3%).

(iii) Methyl 4-[4-(5-nitropyridine-2-yl)phenyl]-4-oxobutyrate

To a solution of 2-chloro-5-nitropyridine (0.30 g, 1.9 mmol) and methyl 4-oxo-4-[4-(4,4,5,5-tetramethyl-[1,3,2]dioxaborolane-2-yl)phenyl]butyrate (0.60 g, 1.9 mmol) obtained in (ii) in 1,2-dimethoxyethan (5 ml), [1,1'-bis(diphenylphosphino)ferrocene]palladium(II) dichloride (0.02 g, 0.02 mmol) and potassium carbonate (0.52 g, 3.8 mmol) were added. The reaction was carried out under nitrogen atmosphere at 80° C. for 4 hours. After cooling, the mixture was extracted with ethyl acetate, the organic layer was concentrated and purified by column chromatography to give the title compound (0.58 g, 97.1%).

(iv) Methyl 4-[4-(5-aminopyridine-2-yl)phenyl]-4-oxobutyrate

The title compound was synthesized in a manner analogous to Example 1 (ii), except for replacing 2-phenyl-5-nitropyridine with methyl 4-[4-(5-nitropyridine-2-yl)phenyl]-4-oxobutyrate obtained in (iii).

(v) Methyl 4-{4-[5-(1-amino-4-sulfonaphthalene-2-ylazo)pyridine-2-yl]phenyl}-4-oxobutyrate sodium salt The title compound was synthesized in a manner analogous to Example 1 (iii), except for replacing 2-phenyl-5-aminopyridine with methyl 4-[4-(5-aminopyridine-2-yl)phenyl]-4-oxobutyrate obtained in (iv).

$^1$H-NMR (DMSO-d6) δ[ppm]=9.27 (1H, d, J=2.1 Hz), 8.77 (1H, d, J=8.1 Hz), 8.52-8.46 (2H, m), 8.34 (1H, s), 8.33 (2H, d, J=8.1 Hz), 8.20 (1H, d, J=8.7 Hz), 8.09 (2H, d, J=8.1 Hz), 7.87 (2H, bs), 7.64-7.59 (1H, m), 7.53-7.48 (1H, m), 3.60 (3H, s), 3.34 (2H, t, J=6.3 Hz), 2.67 (2H, t, J=6.3 Hz)

$^{13}$C-NMR (DMSO-d6) δ[ppm]=198.0, 172.9, 154.4, 147.8, 147.3, 146.4, 142.2, 136.4, 132.5, 132.2, 129.4, 128.7, 128.5, 128.3, 127.7, 126.9, 125.2, 124.2, 124.0, 121.5, 116.6, 51.4, 33.2, 27.6

Example 26

Synthesis of 4-amino-3-(6-biphenyl-3-ylpyridine-3-ylazo)naphthalene-1-sulfonic acid sodium salt

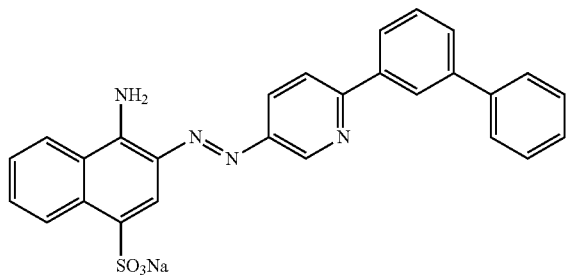

(i) 2-Biphenyl-3-yl-5-nitropyridine

The title compound was synthesized in a manner analogous to Example 2 (i), except for replacing 4-methylphenylboronic acid with 3-biphenylboronic acid.

(ii) 6-Biphenyl-3-ylpyridine-3-ylamine

The title compound was synthesized in a manner analogous to Example 1 (ii), except for replacing 2-phenyl-5-nitropyridine with 2-biphenyl-3-yl-5-nitropyridine obtained in (i).

(iii) 4-Amino-3-(6-biphenyl-3-ylpyridine-3-ylazo)naphthalene-1-sulfonic acid sodium salt The title compound was synthesized in a manner analogous to Example 5 (iii), except for replacing 6-biphenyl-2-ylpyridine-3-ylamine with 6-biphenyl-3-ylpyridine-3-ylamine obtained in (ii).

$^1$H-NMR (DMSO-d6) δ[ppm]=9.28 (1H, d, J=2.1 Hz), 8.78 (1H, d, J=8.4 Hz), 8.52-8.46 (3H, m), 8.37 (1H, s), 8.25 (1H, d, J=8.7 Hz), 8.19 (1H, d, J=7.5 Hz), 7.84 (2H, bs), 7.79-7.74 (3H, m), 7.64-7.59 (2H, m), 7.53-7.48 (3H, m), 7.42-7.38 (1H, m)

$^{13}$C-NMR (DMSO-d6) δ[ppm]=155.8, 147.5, 147.1, 146.3, 140.8, 140.0, 138.8, 132.4, 132.1, 129.6, 129.3, 129.0, 128.6, 128.3, 127.7, 127.6, 126.9, 125.8, 125.1, 125.0, 124.2, 124.0, 121.0, 116.6

Example 27

Synthesis of 4-amino-3-[6-(3-cyanophenyl)pyridine-3-ylazo]naphthalene-1-sulfonic acid sodium salt

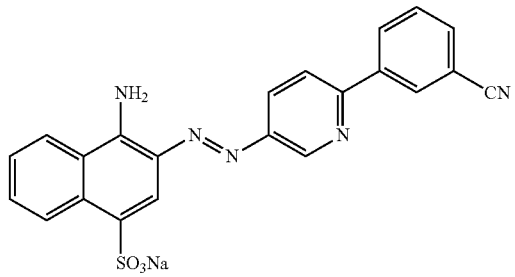

(i) 3-(5-Nitropyridine-2-yl)benzonitrile

The title compound was synthesized in a manner analogous to Example 2 (i), except for replacing 4-methylphenylboronic acid with 3-cyanophenylboronic acid.

(ii) 3-(5-Aminopyridine-2-yl)benzonitrile

The title compound was synthesized in a manner analogous to Example 1 (ii), except for replacing 2-phenyl-5-nitropyridine with 3-(5-nitropyridine-2-yl)benzonitrile obtained in (i).

(iii) 4-Amino-3-[6-(3-cyanophenyl)pyridine-3-ylazo]naphthalene-1-sulfonic acid sodium salt The title compound was synthesized in a manner analogous to Example 1 (iii), except for replacing 2-phenyl-5-aminopyridine with 3-(5-aminopyridine-2-yl)benzonitrile obtained in (ii).

$^1$H-NMR (DMSO-d6) δ[ppm]=9.26 (1H, d, J=2.1 Hz), 8.76 (1H, dd, J=7.5, 0.9 Hz), 8.61 (1H, m), 8.53-8.46 (3H, m), 8.34 (1H, s), 8.23 (1H, d, J=8.7 Hz), 7.92-7.87 (3H, m), 7.72 (1H, m), 7.61 (1H, m), 7.50 (1H, m)

$^{13}$C-NMR (DMSO-d6) δ[ppm]=153.5, 147.9, 147.4, 146.4, 139.2, 132.7, 132.5, 132.2, 131.3, 130.2, 130.1, 129.4, 128.7, 128.3, 127.8, 125.2, 124.2, 124.0, 121.3, 118.8, 116.5, 112.1

Example 28

Synthesis of 4-amino-3-[6-(4-cyanophenyl)pyridine-3-ylazo]naphthalene-1-sulfonic acid sodium salt

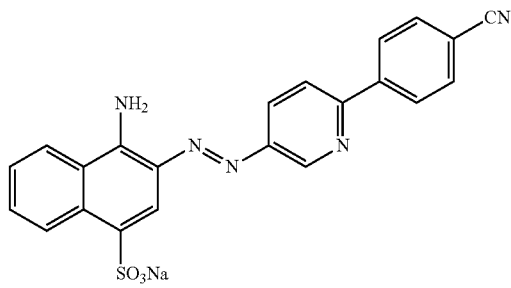

(i) 4-(5-Nitropyridine-2-yl)benzonitrile

The title compound was synthesized in a manner analogous to Example 2 (i), except for replacing 4-methylphenylboronic acid with 4-cyanophenylboronic acid.

(ii) 4-(5-Aminopyridine-2-yl)benzonitrile

The title compound was synthesized in a manner analogous to Example 1 (ii), except for replacing 2-phenyl-5-nitropyridine with 4-(5-nitropyridine-2-yl)benzonitrile obtained in (i).

(iii) 4-Amino-3-[6-(4-cyanophenyl)pyridine-3-ylazo]naphthalene-1-sulfonic acid sodium salt The title compound was synthesized in a manner analogous to Example 1 (iii), except for replacing 2-phenyl-5-aminopyridine with 4-(5-aminopyridine-2-yl)benzonitrile obtained in (ii).

$^1$H-NMR (DMSO-d6) δ[ppm]=9.27 (1H, dd, J=7.5, 0.9 Hz), 8.76 (1H, dd, J=7.5, 0.9 Hz), 8.52-8.46 (2H, m), 8.38-8.33 (3H, m), 8.21 (1H, d, J=8.4 Hz), 7.95 (2H, d, J=8.7 Hz), 7.89 (2H, bs), 7.64-7.59 (1H, m), 7.52-7.47 (1H, m)

$^{13}$C-NMR (DMSO-d6) δ[ppm]=153.6, 147.9, 147.5, 146.4, 142.2, 132.8, 132.5, 132.2, 129.4, 128.7, 128.3, 127.9, 127.3, 125.2, 124.2, 124.0, 121.7, 118.9, 116.5, 111.5

Example 29

Synthesis of 4-amino-3-[6-(3,5-bistrifluoromethylphenyl)pyridine-3-ylazo]naphthalenesulfonic acid sodium salt

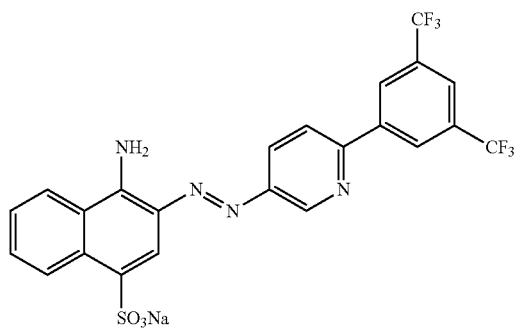

(i) 2-(3,5-Bistrifluoromethylphenyl)-5-nitropyridine

The title compound was synthesized in a manner analogous to Example 2 (i), except for replacing 4-methylphenylboronic acid with 3,5-bistrifluoromethylphenylboronic acid.

(ii) 6-(3,5-Bistrifluoromethylphenyl)pyridine-3-ylamine

The title compound was synthesized in a manner analogous to Example 1 (ii), except for replacing 2-phenyl-5-nitropyridine with 2-(3,5-bistrifluoromethylphenyl)-5-nitropyridine obtained in (i).

(iii) 4-Amino-3-[6-(3,5-bistrifluoromethylphenyl)pyridine-3-ylazo]naphthalenesulfonic acid sodium salt The title compound was synthesized in a manner analogous to Example 1 (iii), except for replacing 2-phenyl-5-aminopyridine with 6-(3,5-bistrifluoromethylphenyl)pyridine-3-ylamine obtained in (ii).

$^1$H-NMR (DMSO-d6) δ[ppm]=9.29 (1H, d, J=1.5 Hz), 8.83 (2H, bs), 8.76 (1H, d, J=7.8 Hz), 8.55-8.33 (4H, m), 8.16 (1H, bs), 7.92 (2H, bs), 7.66-7.48 (2H, m)

$^{13}$C-NMR (DMSO-d6) δ[ppm]=152.0, 148.2, 147.5, 146.5, 140.5, 132.6, 132.3, 131.6, 131.2, 130.8, 130.3, 129.5, 128.8, 128.4, 127.9, 127.0, 125.2, 124.2, 124.1, 121.9, 121.6, 116.6, 115.4

Example 30

Synthesis of 4-amino-3-[6-(4-benzoylphenyl)pyridine-3-ylazo]naphthalene-1-sulfonic acid sodium salt

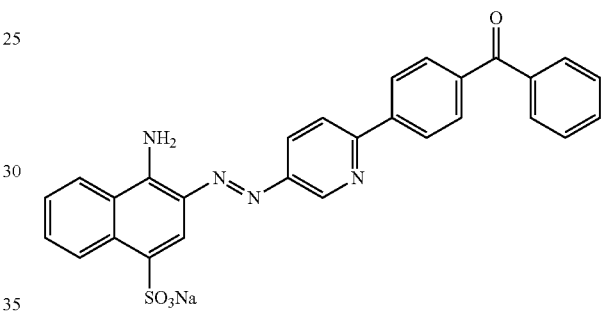

(i) [4-(5-Nitropyridine-2-yl)phenyl]phenylmethanone

The title compound was synthesized in a manner analogous to Example 1 (i), except for replacing phenylboronic acid with 4-benzoylphenylboronic acid.

(ii) [4-(5-Aminopyridine-2-yl)phenyl]phenylmethanone

The title compound was synthesized in a manner analogous to Example 1 (ii), except for replacing 2-phenyl-5-nitropyridine with [4-(5-nitropyridine-2-yl)phenyl]phenylmethanone obtained in (i).

(iii) 4-Amino-3-[6-(4-benzoylphenyl)pyridine-3-ylazo]naphthalene-1-sulfonic acid sodium salt The title compound was synthesized in a manner analogous to Example 1 (iii), except for replacing 2-phenyl-5-aminopyridine with [4-(5-aminopyridine-2-yl)phenyl]phenylmethanone obtained in (ii).

$^1$H-NMR (DMSO-d6) δ[ppm]=9.28 (1H, d, J=1.2 Hz), 8.76 (1H, dd, J=8.3, 1.2 Hz), 8.52 (1H, dd, J=8.7, 2.4 Hz), 8.47 (1H, d, J=8.1 Hz), 8.39-8.33 (3H, m), 8.23 (1H, d, J=8.3 Hz), 7.89-7.77 (6H, m), 7.70-7.50 (5H, m)

$^{13}$C-NMR (DMSO-d6) δ[ppm]=195.4, 154.5, 147.8, 147.3, 146.4, 141.8, 137.2, 137.1, 132.8, 132.6, 132.2, 130.3, 129.6, 129.4, 128.7, 128.4, 128.4, 127.8, 126.8, 125.1, 124.2, 124.0, 121.5, 116.5

Example 31

Synthesis of 4-amino-3-[6-(2-propoxyphenyl)pyridine-3-ylazo]naphthalene-1-sulfonic acid sodium salt

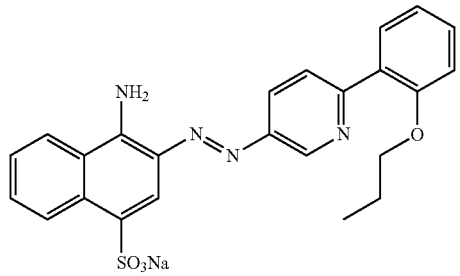

(i) 5-Nitro-2-(2-propoxyphenyl)pyridine

The title compound was synthesized in a manner analogous to Example 1 (i), except for replacing phenylboronic acid with 2-propoxyphenylboronic acid.

(ii) 6-(2-Propoxyphenyl)pyridine-3-ylamine

The title compound was synthesized in a manner analogous to Example 1 (ii), except for replacing 2-phenyl-5-nitropyridine with 5-nitro-2-(2-propoxyphenyl)pyridine obtained in (i).

(iii) 4-Amino-3-[6-(2-propoxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2-propoxyphenyl)pyridine-3-ylamine obtained in (ii).

$^1$H-NMR δ[ppm]=9.23 (1H, dd, J=2.4, 0.6 Hz), 8.76 (1H, dd, J=8.4, 0.9 Hz), 8.43-8.48 (2H, m), 8.34 (1H, s), 8.13 (1H, d, J=8.7 Hz), 7.92 (1H, dd, J=7.5, 1.5 Hz), 7.76 (2H, bs), 7.368-7.631 (3H, m), 7.04-7.16 (2H, m), 4.04 (2H, t, J=6.3 Hz), 1.73-1.797 (2H, m), 1.04 (3H, t, J=6.6 Hz)

$^{13}$C-NMR δ[ppm]=147.0, 146.7, 146.4, 132.4, 132.1, 130.8, 130.5, 129.3, 128.4, 128.3, 127.7, 125.8, 125.1, 124.2, 123.9, 120.6, 116.3, 112.9, 69.6, 22.1, 10.8

Example 32

Synthesis of 4-amino-3-[6-(4-fluoro-2-methylphenyl)pyridine-3-ylazo]naphthalene-1-sulfonic acid sodium salt

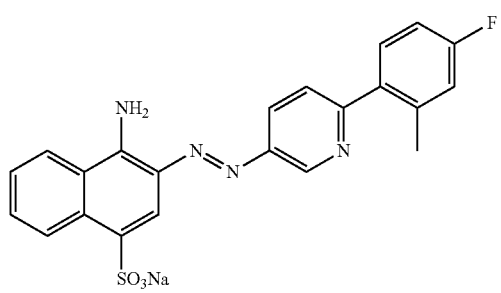

(i) 2-(4-Fluoro-2-methylphenyl)-5-nitropyridine

The title compound was synthesized in a manner analogous to Example 2 (i), except for replacing 4-methylphenylboronic acid with 4-fluoro-2-methylphenylboronic acid.

(ii) 6-(4-Fluoro-2-methylphenyl)pyridine-3-ylamine

The title compound was synthesized in a manner analogous to Example 1 (ii), except for replacing 2-phenyl-5-nitropyridine with 2-(4-fluoro-2-methylphenyl)-5-nitropyridine obtained in (i).

(iii) 4-Amino-3-[6-(4-fluoro-2-methylphenyl)pyridine-3-ylazo]naphthalene-1-sulfonic acid sodium salt The title compound was synthesized in a manner analogous to Example 5 (iii), except for replacing 6-biphenyl-2-ylpyridine-3-ylamine with 6-(4-fluoro-2-methylphenyl)pyridine-3-ylamine obtained in (ii).

$^1$H-NMR δ[ppm]=9.22 (1H, d, J=2.4 Hz), 8.76 (1H, d, J=8.1), 8.49-8.44 (2H, m), 8.34 (1H, s), 7.82 (2H, bs), 7.67-7.47 (4H, m), 7.21-7.11 (2H, m), 2.41 (3H, s)

$^{13}$C-NMR (DMSO-d6) δ[ppm]=163.5, 160.3, 158.2, 147.1, 146.7, 145.4, 138.8, 138.7, 136.1, 136.1, 132.4, 132.1, 131.8, 131.7, 129.2, 128.6, 128.3, 127.2, 125.1, 124.6, 124.2, 124.0, 117.3, 117.1, 116.6, 112.9, 112.6, 20.4. 20.4

Example 33

Synthesis of 4-amino-3-[6-(5-fluoro-2-propoxyphenyl)pyridine-3-ylazo]naphthalene-1-sulfonic acid sodium salt

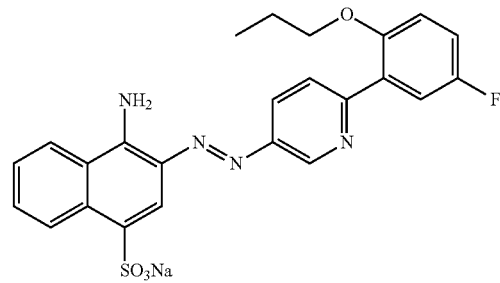

(i) 2-(5-Fluoro-2-propoxyphenyl)-5-nitropyridine

The title compound was synthesized in a manner analogous to Example 1 (i), except for replacing phenylboronic acid with 5-fluoro-2-propoxyphenylboronic acid.

(ii) 6-(5-Fluoro-2-propoxyphenyl)pyridine-3-ylamine

The title compound was synthesized in a manner analogous to Example 1 (ii), except for replacing 2-phenyl-5-nitropyridine with 2-(5-fluoro-2-propoxyphenyl)-5-nitropyridine obtained in (i).

(iii) 4-Amino-3-[6-(5-fluoro-2-propoxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(5-fluoro-2-propoxyphenyl)pyridine-3-ylamine obtained in (ii).

$^1$H-NMR δ[ppm]=9.23 (1H, d, J=2.4), 8.75 (1H, dd, J=8.4, 0.9), 8.48-8.45 (2H, m), 8.32 (1H, s), 8.17 (1H, d, J=8.4), 7.78 (2H, bs), 7.73 (1H, dd, J=9.9, 3.0), 7.63-7.48 (2H, m), 7.27-7.15 (2H, m), 4.03 (2H, t, J=6.3), 1.82-1.73 (2H, m), 0.99 (3H, t, J=7.2)

$^{13}$C-NMR (DMSO-d6) δ[ppm]=158.0, 154.8, 153.6, 153.6, 153.0, 152.9, 147.2, 147.0, 146.3, 132.5, 132.1, 129.3, 128.9, 128.8, 128.5, 128.3, 126.1, 125.0, 124.1, 123.9, 116.7, 116.3, 114.7, 114.6, 70.4, 22.1, 10.7

Example 34

Synthesis of 4-amino-3-[6-(2-fluoro-6-propoxyphenyl)pyridine-3-ylazo]naphthalene-1-sulfonic acid sodium salt

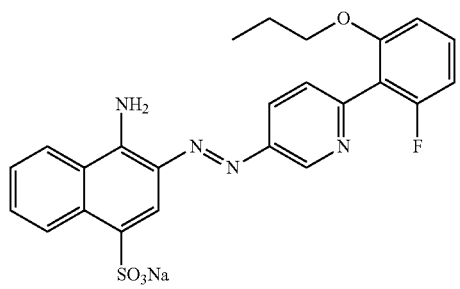

(i) 2-(2-Fluoro-6-propoxyphenyl)-5-nitropyridine

The title compound was synthesized in a manner analogous to Example 2 (i), except for replacing 4-methylphenylboronic acid with 2-fluoro-6-propoxyphenylboronic acid.

(ii) 6-(2-Fluoro-6-propoxyphenyl)pyridine-3-ylamine

The title compound was synthesized in a manner analogous to Example 1 (ii), except for replacing 2-phenyl-5-nitropyridine with 2-(2-fluoro-6-propoxyphenyl)-5-nitropyridine obtained in (i).

(iii) 4-Amino-3-[6-(2-fluoro-6-propoxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2-fluoro-6-propoxyphenyl)pyridine-3-ylamine obtained in (ii).

$^1$H-NMR (DMSO-d6) δ[ppm]=9.20 (1H, dd, J=2.4, 0.6), 8.75 (1H, dd, J=8.4, 1.2), 8.48 (1H, d, J=8.1), 8.44 (1H, dd, J=8.4, 2.4), 8.32 (1H, s), 7.83 (2H, bs), 7.64-7.38 (4H, m), 6.99-6.88 (2H, m), 3.96 (2H, t, J=6.3), 1.62-1.55 (2H, m), 0.83 (3H, t, J=7.2)

$^{13}$C-NMR (DMSO-d6) δ[ppm]=161.7, 158.5, 157.4, 157.3, 151.5, 147.0, 147.0, 145.6, 132.4, 132.1, 130.6, 130.4, 129.2, 128.5, 128.3, 126.5, 126.3, 125.0, 124.2, 124.0, 118.0, 117.7, 116.6, 108.6, 108.0, 107.7, 70.0, 21.9, 10.4

Example 35

Synthesis of 4-amino-3-[6-(4-fluoro-2-propoxyphenyl)pyridine-3-ylazo]naphthalene-1-sulfonic acid sodium salt

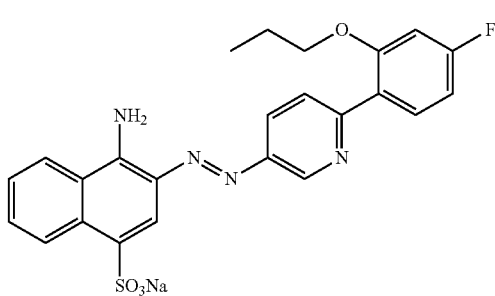

(i) 2-(4-Fluoro-2-propoxyphenyl)-5-nitropyridine

The title compound was synthesized in a manner analogous to Example 2 (i), except for replacing 4-methylphenylboronic acid with 4-fluoro-2-propoxyphenylboronic acid.

(ii) 6-(4-Fluoro-2-propoxyphenyl)pyridine-3-ylamine

The title compound was synthesized in a manner analogous to Example 1 (ii), except for replacing 2-phenyl-5-nitropyridine with 2-(4-fluoro-2-propoxyphenyl)-5-nitropyridine obtained in (i).

(iii) 4-Amino-3-[6-(4-fluoro-2-propoxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(4-fluoro-2-propoxyphenyl)pyridine-3-ylamine obtained in (ii).

$^1$H-NMR (DMSO-d6) δ[ppm]=9.21 (1H, d, J=2.1 Hz), 8.75 (1H, d, J=7.8 Hz), 8.49-8.42 (2H, m), 8.32 (1H, s), 8.06 (1H, d, J=8.7 Hz), 7.97 (1H, dd, J=8.7, 7.2 Hz), 7.74 (2H, bs), 7.62-7.47 (2H, m), 7.09-6.88 (2H, m), 4.07 (2H, t, J=6.3 Hz), 1.83-1.72 (2H, m), 1.00 (3H, t, J=7.2 Hz)

$^{13}$C-NMR (DMSO-d6) δ[ppm]=165.0, 161.8, 157.9, 157.7, 154.3, 146.9, 146.7, 146.3, 132.5, 132.3, 132.1, 132.1, 129.3, 128.4, 128.3, 125.9, 125.0, 124.7, 124.2, 124.1, 124.1, 123.9, 107.3, 107.4, 100.9, 100.6, 70.2, 21.9, 10.7

Example 36

Synthesis of 4-amino-3-[6-(5-fluoro-2-methylphenyl)pyridine-3-ylazo]naphthalene-1-sulfonic acid sodium salt

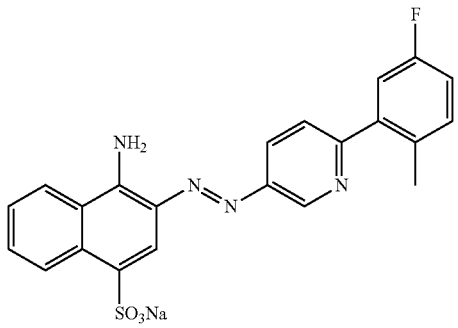

(i) 2-(5-Fluoro-2-methylphenyl)-5-nitropyridine

The title compound was synthesized in a manner analogous to Example 2 (i), except for replacing 4-methylphenylboronic acid with 5-fluoro-2-methylphenylboronic acid.

(ii) 6-(5-Fluoro-2-methylphenyl)pyridine-3-ylamine

The title compound was synthesized in a manner analogous to Example 1 (ii), except for replacing 2-phenyl-5-nitropyridine with 2-(5-fluoro-2-methylphenyl)-5-nitropyridine obtained in (i).

(iii) 4-Amino-3-[6-(5-fluoro-2-methylphenyl)pyridine-3-ylazo]naphthalene-1-sulfonic acid sodium salt The title compound was synthesized in a manner analogous to Example 1 (iii), except for replacing 2-phenyl-5-aminopyridine with 6-(5-fluoro-2-methylphenyl)pyridine-3-ylamine obtained in (ii).

$^1$H-NMR (DMSO-d6) δ[ppm]=9.24 (1H, d, J=2.4 Hz), 8.75 (1H, dd, J=8.4, 0.9 Hz), 8.49-8.44 (2H, m), 8.32 (1H, s), 7.80 (2H, bs), 7.71 (1H, d, J=8.4 Hz), 7.70-7.15 (5H, m), 2.37 (3H, s)

$^{13}$C-NMR (DMSO-d6) δ[ppm]=147.1, 146.9, 145.4, 141.3, 141.2, 132.6, 132.5, 132.1, 131.7, 131.7, 129.3, 128.5, 128.3, 127.3, 125.1, 124.6, 124.2, 123.9, 116.4, 116.2, 115.9, 115.2, 114.9, 19.6

Example 37

Synthesis of 4-amino-3-[6-(2-fluoro-5-methylphenyl)pyridine-3-ylazo]naphthalene-1-sulfonic acid sodium salt

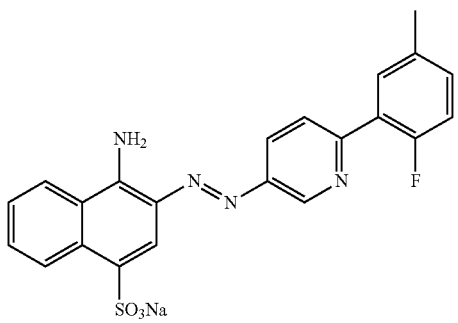

(i) 2-(2-Fluoro-5-methylphenyl)-5-nitropyridine

The title compound was synthesized in a manner analogous to Example 1 (i), except for replacing phenylboronic acid with 2-fluoro-5-methylphenylboronic acid.

(ii) 6-(2-Fluoro-5-methylphenyl)pyridine-3-ylamine

The title compound was synthesized in a manner analogous to Example 1 (ii), except for replacing 2-phenyl-5-nitropyridine with 2-(2-fluoro-5-methylphenyl)-5-nitropyridine obtained in (i).

(iii) 4-Amino-3-[6-(2-fluoro-5-methylphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2-fluoro-5-methylphenyl)pyridine-3-ylamine obtained in (ii).

$^1$H-NMR (DMSO-d6) δ[ppm]=9.26 (1H, d, J=2.7 Hz), 8.78 (1H, dd, J=8.4, 0.9 Hz), 8.48-8.45 (2H, m), 8.35 (1H, s), 7.93-7.84 (4H, m), 7.64-7.48 (2H, m), 7.30-7.19 (2H, m), 2.37 (3H, s)

$^{13}$C-NMR (DMSO-d6) δ[ppm]=159.9, 156.6, 152.4, 147.2, 147.1, 133.9, 132.5, 132.1, 130.9, 129.3, 128.6, 128.3, 127.2, 126.0, 125.8, 125.1, 124.5, 124.4, 124.2, 123.9, 116.7, 116.3, 116.0, 20.2

Example 38

Synthesis of 4-amino-3-[6-(2-butoxyphenyl)pyridine-3-ylazo]naphthalene-1-sulfonic acid sodium salt

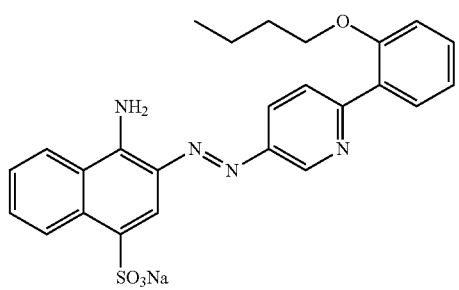

(i) 2-(2-Butoxyphenyl)-5-nitropyridine

The title compound was synthesized in a manner analogous to Example 1 (i), except for replacing phenylboronic acid with 2-butoxyphenylboronic acid.

(ii) 6-(2-Butoxyphenyl)pyridine-3-ylamine

The title compound was synthesized in a manner analogous to Example 1 (ii), except for replacing 2-phenyl-5-nitropyridine with 2-(2-butoxyphenyl)-5-nitropyridine obtained in (i).

(iii) 4-Amino-3-[6-(2-butoxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2-butoxyphenyl)pyridine-3-ylamine obtained in (ii).

$^1$H-NMR (DMSO-d6) δ[ppm]=9.22 (1H, d, J=2.4 Hz), 8.77 (1H, d, J=8.4 Hz), 8.46 (1H, d, J=7.5 Hz), 8.43 (1H, dd, J=8.7, 2.4 Hz), 8.34 (1H, s), 8.08 (1H, d, J=8.7 Hz), 7.91 (1H, dd, J=7.8, 1.8 Hz), 7.76 (2H, bs), 7.63-7.37 (3H, m), 7.15 (1H, d, J=8.1 Hz), 7.08 (1H, dd, J=7.8, 7.8 Hz), 4.08 (2H, t, J=6.6 Hz), 1.74 (2H, tt, J=6.6, 6.6 Hz), 1.44 (2H, tt, J=7.2, 6.6 Hz), 0.92 (3H, t, J=7.2 Hz)

$^{13}$C-NMR (DMSO-d6) δ[ppm]=156.4, 155.2, 146.9, 146.7, 146.3, 132.4, 132.0, 130.8, 130.4, 129.3, 128.4, 128.3, 127.7, 125.8, 125.0, 125.0, 124.2, 123.9, 120.6, 116.4, 112.9, 67.8, 30.8, 18.9, 13.7

Example 39

Synthesis of 4-amino-3-[6-(2-hexyloxyphenyl)pyridine-3-ylazo]naphthalene-1-sulfonic acid sodium salt

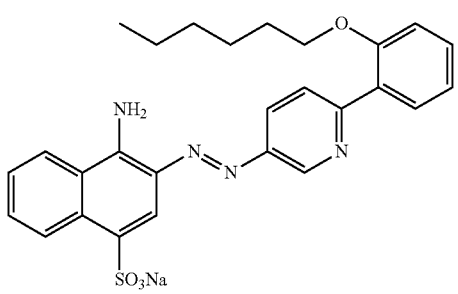

(i) 2-(2-Hexyloxyphenyl)-5-nitropyridine

The title compound was synthesized in a manner analogous to Example 1 (i), except for replacing phenylboronic acid with 2-hexyloxyphenylboronic acid.

(ii) 6-(2-Hexyloxyphenyl)pyridine-3-ylamine

The title compound was synthesized in a manner analogous to Example 1 (ii), except for replacing 2-phenyl-5-nitropyridine with 2-(2-hexyloxyphenyl)-5-nitropyridine obtained in (i).

(iii) 4-Amino-3-[6-(2-hexyloxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2-hexyloxyphenyl)pyridine-3-ylamine obtained in (ii).

$^1$H-NMR (DMSO-d6) δ[ppm]=9.16 (1H, d, J=2.4 Hz), 8.69 (1H, dd, J=8.4, 0.9 Hz), 8.42 (1H, d, J=6.0 Hz), 8.36 (1H, dd, J=8.7, 2.4 Hz), 8.27 (1H, s), 8.01 (1H, d, J=8.7 Hz), 7.84 (1H, dd, J=7.5, 1.8 Hz), 7.20 (2H, bs), 7.58-7.30 (3H, m), 7.07 (1H, d, J=8.1 Hz), 7.01 (1H, dd, J=8.1, 8.1 Hz), 3.99 (2H, t, J=6.6 Hz), 1.69-1.64 (2H, m), 1.35-1.18 (6H, m), 0.76 (3H, t, J=6.9 Hz)

$^{13}$C-NMR (DMSO-d6) δ[ppm]=156.5, 155.1, 147.0, 146.7, 146.1, 132.2, 132.1, 130.8, 130.5, 129.3, 128.5, 128.3, 127.6, 126.1, 125.1, 125.1, 124.2, 123.9, 120.6, 116.5, 113.0, 68.2, 30.9, 28.6, 25.3, 22.0, 13.9

Example 40

Synthesis of 4-amino-3-[6-(4-butylphenyl)pyridine-3-ylazo]naphthalene-1-sulfonic acid sodium salt

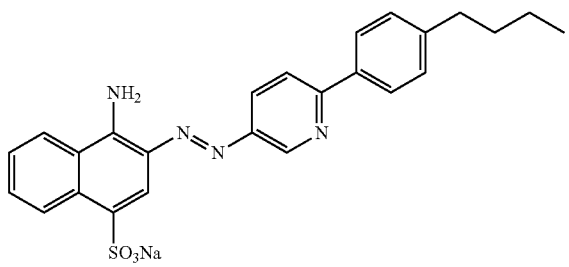

(i) 2-(4-Butylphenyl)-5-nitropyridine

The title compound was synthesized in a manner analogous to Example 1 (i), except for replacing phenylboronic acid with 4-butylphenylboronic acid.

(ii) 6-(4-Butylphenyl)pyridine-3-ylamine

The title compound was synthesized in a manner analogous to Example 1 (ii), except for replacing 2-phenyl-5-nitropyridine with 2-(4-butylphenyl)-5-nitropyridine obtained in (i).

(iii) 4-Amino-3-[6-(4-butylphenyl)pyridine-3-ylazo]naphthalene-1-sulfonic acid sodium salt The title compound was synthesized in a manner analogous to Example 1 (iii), except for replacing 2-phenyl-5-aminopyridine with 6-(4-butylphenyl)pyridine-3-ylamine obtained in (ii).

$^1$H-NMR (DMSO-d6) δ[ppm]=9.21 (1H, d, J=2.4 Hz), 8.77 (1H, d, J=8.4 Hz), 8.48-8.43 (2H, m), 8.33 (1H, s), 8.11-8.05 (3H, m), 7.78 (2H, bs), 7.63-7.48 (2H, m), 7.31 (2H, d, J=8.1 Hz), 2.63 (2H, t, J=7.5 Hz), 1.61-1.56 (2H, m), 1.35-1.28 (2H, m), 0.90 (3H, t, J=7.2 Hz)

$^{13}$C-NMR (DMSO-d6) δ[ppm]=156.0, 147.2, 146.9, 146.3, 143.9, 135.6, 132.4, 132.0, 129.3, 128.8, 128.5, 128.3, 127.5, 126.6, 125.1, 124.2, 123.9, 120.3, 116.6, 34.6, 33.0, 21.8, 13.8

Example 41

Synthesis of 4-amino-3-[6-(2-hydroxyphenyl)pyridine-3-ylazo]naphthalene-1-sulfonic acid sodium salt

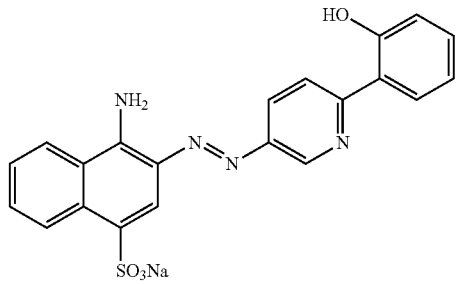

(i) 2-(5-Nitropyridine-2-yl)phenol

The title compound was synthesized in a manner analogous to Example 1 (i), except for replacing phenylboronic acid with 2-hydroxyphenylboronic acid.

(ii) 2-(5-Aminopyridine-2-yl)phenol

The title compound was synthesized in a manner analogous to Example 1 (ii), except for replacing 2-phenyl-5-nitropyridine with 2-(5-nitropyridine-2-yl)phenol obtained in (i).

(iii) 4-Amino-3-[6-(2-hydroxyphenyl)pyridine-3-ylazo]naphthalene-1-sulfonic acid sodium salt The title compound was synthesized in a manner analogous to Example 1 (iii), except for replacing 2-phenyl-5-aminopyridine with 2-(5-aminopyridine-2-yl)phenol obtained in (ii).

$^1$H-NMR (DMSO-d6) δ[ppm]=14.09 (1H, bs), 9.22 (1H, d, J=2.4 Hz), 8.75 (1H, d, J=7.8 Hz), 8.61 (1H, dd, J=9.0, 2.4 Hz), 8.47 (1H, d, J=7.8 Hz), 8.35 (1H, s), 8.32 (1H, s), 8.10 (1H, d, J=7.8 Hz), 7.84 (2H, bs), 7.59-7.63 (1H, m), 7.48-7.53 (1H, m), 7.30-7.36 (1H, m), 6.92-6.97 (2H, m)

$^{13}$C-NMR (DMSO-d6) δ[ppm]=159.2, 156.6, 147.5, 146.8, 142.9, 132.6, 132.2, 131.7, 129.3, 129.0, 128.7, 128.4, 127.4, 125.1, 124.2, 124.0, 120.6, 119.1, 118.9, 118.0, 116.2

Example 42

Synthesis of 4-amino-3-{6-[2-(6-hydroxyhexyloxy)phenyl]pyridine-3-ylazo}naphthalene-1-sulfonic acid sodium salt

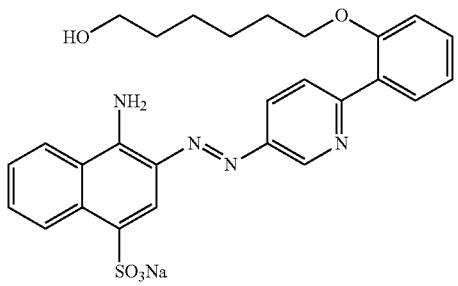

(i) 6-[2-(5-Nitropyridine-2-yl)phenoxy]hexane-1-ol

To a solution of 2-(5-nitropyridine-2-yl)phenol (1.0 g, 4.6 mmol) synthesized in Example 41 (i), 6-chlorohexanol (0.76 g, 5.6 mmol), and potassium carbonate (1.28 g, 9.3 mmol) in N,N-dimethylformamide (5 ml), potassium iodide (0.154 g, 0.93 mmol) was added and the reaction was carried out at 80° C. for 4 hours. The mixture was cooled, added with water and extracted with methylene chloride. The organic layer was dried with anhydrous sodium sulfate, concentrated to dryness under reduced pressure, and purified by column chromatography. Recrystallization gave the title compound (1.08 g, 74.5%).

(ii) 6-[2-(5-Aminopyridine-2-yl)phenoxy]hexane-1-ol

The title compound was synthesized in a manner analogous to Example 1 (ii), except for replacing 2-phenyl-5-nitropyridine with 6-[2-(5-nitropyridine-2-yl)phenoxy]hexane-1-ol obtained in (i).

(iii) 4-Amino-3-{6-[2-(6-hydroxyhexyloxy)phenyl]pyridine-3-ylazo}naphthalene-1-sulfonic acid sodium salt The title compound was synthesized in a manner analogous to Example 1 (iii), except for replacing 2-phenyl-5-aminopyridine with 6-[2-(5-aminopyridine-2-yl)phenoxy]hexane-1-ol obtained in (ii).

$^1$H-NMR (DMSO-d6) δ[ppm]=9.23 (1H, s), 8.76 (1H, d, J=8.4 Hz), 8.42-8.48 (2H, m), 8.33 (1H, s), 8.09 (1H, d, J=8.4 Hz), 7.92 (1H, d, J=7.5 Hz), 7.76 (2H, bs), 7.61-7.63 (1H, m), 7.48-7.53 (1H, m), 7.37-7.43 (1H, m), 7.05-7.17 (2H, m), 4.36 (1H, t, J=4.8 Hz), 4.07 (2H, t, J=6.0 Hz), 1.40-1.75 (10H, m)

$^{13}$C-NMR (DMSO-d7) δ[ppm]=156.5, 155.2, 147.0, 146.7, 146.2, 132.4, 132.1, 130.8, 130.5, 129.3, 128.4, 128.3, 127.7, 126.0, 125.0, 124.2, 123.9, 120.6, 116.3, 112.9, 68.1, 60.6, 32.5, 28.7, 25.5, 25.2

Example 43

Synthesis of 4-{2-[5-(1-amino-4-sulfonaphthalene-2-ylazo)pyridine-2-yl]phenoxy}butyric acid disodium salt

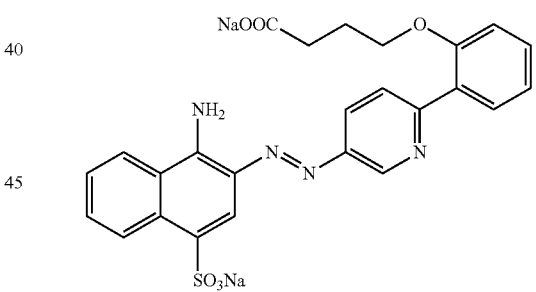

(i) 4-[2-(5-Nitropyridine-2-yl)phenoxy]butyric acid

To a solution of 2-(5-nitropyridine-2-yl)phenol (0.75 g, 3.5 mmol) synthesized in Example 41 (i), ethyl 4-bromo-n-butyrate (0.81 g, 4.2 mmol) and potassium carbonate (0.96 g, 6.9 mmol) in acetonitrile (10 ml), potassium iodide (0.115 g, 0.69 mmol) was added and the reaction was carried out at 80° C. for 2 hours. The mixture was cooled, and extracted with addition of water and methylene chloride. The organic layer was dried with anhydrous sodium sulfate, and concentrated under reduced pressure. Hydrolysis was carried out with aqueous sodium hydroxide in methanol for 1 hour, and the reaction was neutralized with addition of hydrochloric acid. The precipitated solids were filtered to give the title compound (0.92 g, 87.0%).

(ii) 4-[2-(5-Aminopyridine-2-yl)phenoxy]butyric acid

The title compound was synthesized in a manner analogous to Example 1 (ii), except for replacing 2-phenyl-5-nitropyridine with 4-[2-(5-nitropyridine-2-yl)phenoxy]butyric acid obtained in (i).

(iii) 4-{2-[5-(1-Amino-4-sulfonaphthalene-2-ylazo)pyridine-2-yl]phenoxy}butyric acid disodium salt The title compound was synthesized in a manner analogous to Example 1 (iii), except for replacing 2-phenyl-5-aminopyridine with 4-[2-(5-aminopyridine-2-yl)phenoxy]butyric acid obtained in (ii).

$^1$H-NMR (DMSO-d6) δ[ppm]=9.21 (1H, d, J=2.1 Hz), 8.76 (1H, d, J=8.4 Hz), 8.46 (1H, d, J=8.1 Hz), 8.41 (1H, dd, J=8.4, 2.1 Hz), 8.32 (1H, s), 8.13 (1H, d, J=8.4 Hz), 7.92 (1H, d, J=7.5 Hz), 7.76 (2H, bs), 7.57-7.62 (1H, m), 7.47-7.49 (1H, m), 7.36-7.41 (1H, m), 7.16 (1H, d, J=8.4 Hz), 7.03-7.08 (1H, m), 4.11 (2H, t, J=6.6 Hz), 2.06-2.11 (2H, m), 1.94 (2H, t, J=6.6 Hz)

$^{13}$C-NMR (DMSO-d6) δ[ppm]=176.8, 156.6, 155.2, 146.8, 146.6, 146.1, 132.5, 132.0, 130.7, 130.4, 129.3, 128.3, 128.3, 127.5, 125.8, 125.0, 125.0, 124.2, 123.9, 120.4, 116.5, 112.8, 68.5, 34.1, 26.1

Example 44

Synthesis of 4-amino-3-{6-[2-(3-hydroxypropoxy)phenyl]pyridine-3-ylazo}naphthalene-1-sulfonic acid sodium salt

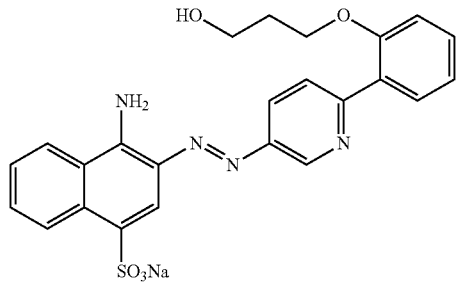

(i) 3-[2-(5-Nitropyridine-2-yl)phenoxy]propane-1-ol

To a solution of 2-(5-nitropyridine-2-yl)phenol (0.50 g, 2.3 mmol) synthesized in Example 41 (i), 3-bromopropanol (0.39 g, 2.8 mmol) and potassium carbonate (0.64 g, 4.6 mmol) in acetonitrile (8 ml), potassium iodide (0.077 g, 0.46 mmol) was added and the reaction was carried out at 80° C. for 4 hours. The mixture was cooled, added with water and extracted with methylene chloride. The organic layer was dried with anhydrous sodium sulfate, concentrated to dryness under reduced pressure, and purified by column chromatography. Recrystallization gave the title compound (0.47 g, 74.5%).

(ii) 3-[2-(5-Aminopyridine-2-yl)phenoxy]propane-1-ol

The title compound was synthesized in a manner analogous to Example 1 (ii), except for replacing 2-phenyl-5-nitropyridine with 3-[2-(5-nitropyridine-2-yl)phenoxy]propane-1-ol obtained in (i).

(iii) 4-Amino-3-{6-[2-(3-hydroxypropoxy)phenyl]pyridine-3-ylazo}naphthalene-1-sulfonic acid sodium salt The title compound was synthesized in a manner analogous to Example 1 (iii), except for replacing 2-phenyl-5-aminopyridine with 3-[2-(5-aminopyridine-2-yl)phenoxy]propane-1-ol obtained in (ii).

$^1$H-NMR (DMSO-d6) δ[ppm]=9.21 (1H, dd, J=2.4, 0.6 Hz), 8.76 (1H, dd, J=8.1, 1.2 Hz), 8.40-8.47 (2H, m), 8.32 (1H, s), 8.08 (1H, dd, J=8.4, 0.6 Hz), 7.91 (1H, dd, J=7.8, 1.8 Hz), 7.74 (2H, bs), 7.57-7.62 (1H, m), 7.47-7.52 (1H, m), 7.38-7.44 (1H, m), 7.05-7.19 (2H, m), 4.56 (1H, t, J=5.4 Hz), 4.16 (2H, t, J=6.0 Hz), 3.54-3.61 (2H, m), 1.89-1.93 (2H, m)

$^{13}$C-NMR (DMSO-d6) δ[ppm]=156.4, 155.2, 146.8, 146.6, 146.3, 146.2, 132.5, 132.0, 130.4, 129.3, 128.4, 128.2, 127.7, 124.9, 124.2, 123.9, 123.8, 120.6, 116.5, 116.4, 112.8, 65.2, 57.4, 32.1

Example 45

Synthesis of 4-amino-3-[6-(2-isobutoxyphenyl)pyridine-3-ylazo]naphthalene-1-sulfonic acid sodium salt

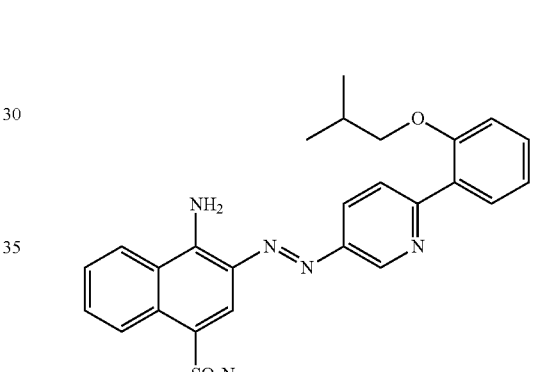

(i) 2-(2-Isobutoxyphenyl)-5-nitropyridine

To a solution of 2-(5-nitropyridine-2-yl)phenol (0.60 g, 2.8 mmol) synthesized in Example 41 (i), isobutyl bromide (0.46 g, 3.3 mmol) and potassium carbonate (0.77 g, 5.6 mmol) in acetonitrile (3 ml), potassium iodide (0.092 g, 0.56 mmol) was added and the reaction was carried out at 80° C. for 4 hours. The mixture was cooled, added with water, crystallized and filtered. The crystals were purified by column chromatography to give the title compound (0.62 g, 81.3%).

(ii) 6-(2-Isobutoxyphenyl)pyridine-3-ylamine

The title compound was synthesized in a manner analogous to Example 1 (ii), except for replacing 2-phenyl-5-nitropyridine with 2-(2-isobutoxyphenyl)-5-nitropyridine obtained in (i).

(iii) 4-Amino-3-[6-(2-isobutoxyphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2-isobutoxyphenyl)pyridine-3-ylamine obtained in (ii).

¹H-NMR (DMSO-d6) δ[ppm]=9.23 (1H, d, J=2.4 Hz), 8.75 (1H, d, J=8.7 Hz), 8.45-8.48 (2H, m), 8.33 (1H, s), 8.08 (1H, d, J=8.7 Hz), 7.90 (1H, dd, J=2.5, 1.8 Hz), 7.75 (2H, bs), 7.58-7.63 (1H, m), 7.47-7.52 (1H, m), 7.37-7.40 (1H, m), 7.05-7.16 (2H, m), 3.87 (2H, d, J=6.3 Hz), 1.99-2.09 (1H, m), 0.99 (6H, d, J=6.6 Hz)

¹³C-NMR (DMSO-d6) δ[ppm]=156.5, 155.3, 147.2, 146.7, 132.4, 132.1, 130.9, 130.5, 129.3, 128.5, 128.4, 128.3, 127.7, 125.7, 125.1, 124.2, 124.0, 120.6, 116.2, 116.1, 112.8, 74.4, 27.9, 19.4, 19.3

Example 46

Synthesis of 4-amino-3-[6-(5-chloro-2-hydroxyphenyl)pyridine-3-ylazo]naphthalene-1-sulfonic acid sodium salt

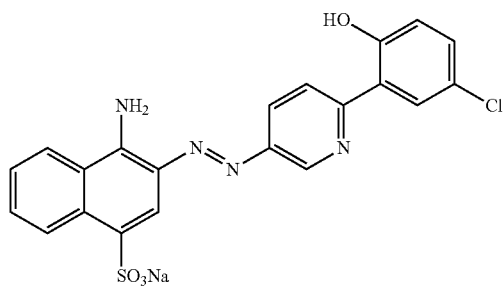

(i) 2-(3-Chlorophenyl)-5-nitropyridine

The title compound was synthesized in a manner analogous to Example 1 (i), except for replacing phenylboronic acid with 3-chlorophenylboronic acid.

(ii) 4-Chloro-2-(5-nitropyridine-2-yl)phenol

To toluene (14.0 ml) and acetic anhydride (14.0 ml), 2-(3-chlorophenyl)-5-nitropyridine (1.05 g, 4.5 mmol) obtained in (i), diacetoxyiodobenzene (1.60 g, 5.0 mmol) and palladium acetate (0.08 g, 0.36 mmol) were added, and reacted under atmosphere of air at 100° C. for 1 hour. The solvent was distilled off under reduced pressure. Purification by column chromatography resulted in an oil. The resulting oil was dissolved in methanol, added with 35% hydrochloric acid, and hydrolyzed at room temperature for 2 hours. The precipitated crystals were filtered to give the title compound (1.0 g, 89.2%).

(iii) 2-(5-Aminopyridine-2-yl)-4-chlorophenol

The title compound was synthesized in a manner analogous to Example 1 (ii), except for replacing 2-phenyl-5-nitropyridine with 4-chloro-2-(5-nitropyridine-2-yl)phenol obtained in (ii).

(iv) 4-Amino-3-[6-(5-chloro-2-hydroxyphenyl)pyridine-3-ylazo]naphthalene-1-sulfonic acid sodium salt The title compound was synthesized in a manner analogous to Example 1 (iii), except for replacing 2-phenyl-5-aminopyridine with 2-(5-aminopyridine-2-yl)-4-chlorophenol obtained in (iii).

¹H-NMR (DMSO-d6) δ[ppm]=14.05 (1H, s), 9.22 (1H, d, J=2.1 Hz), 8.75 (1H, d, J=8.7 Hz), 8.61 (1H, dd, J=8.7, 2.1 Hz), 8.47 (1H, d, J=8.1 Hz), 8.41 (1H, d, J=8.7 Hz), 8.31 (1H, s), 8.17 (1H, s), 7.87 (2H, bs), 7.58-7.63 (1H, m), 7.47-7.53 (1H, m), 7.35 (1H, dd, J=9.0, 2.4 Hz), 6.99 (1H, d, J=9.0 Hz)

¹³C-NMR (DMSO-d6) δ[ppm]=157.8, 154.9, 147.6, 147.1, 143.1, 143.0, 132.6, 132.3, 131.1, 129.4, 128.7, 128.3, 126.8, 126.7, 125.1, 124.2, 122.8, 120.6, 119.7, 116.2, 116.1

Example 47

Synthesis of 4-amino-3-[6-(4-methylbiphenyl-2-yl)pyridine-3-ylazo]naphthalene-1-sulfonic acid sodium salt

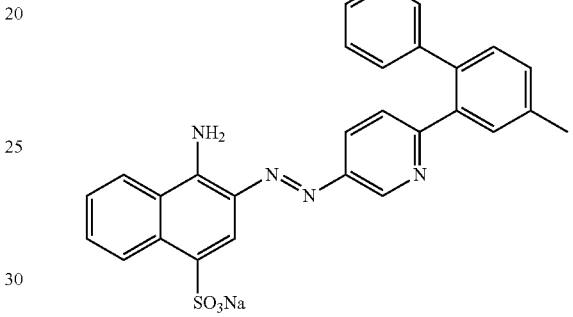

(i) Diphenyliodonium tetrafluoroborate

Phenylboronic acid (0.79 g, 6.5 mmol), methylene chloride (62 ml), and boron trifluoride ethyl ether complex (0.97 g, 6.8 mmol) were charged and cooled to 0° C. A solution of diacetoxy iodobenzene (2.0 g, 6.2 mmol) in methylene chloride (62 ml) was added dropwise. The reaction was carried out at 0° C. for 1.5 hours. A saturated aqueous solution of sodium fluoroborate (13.6 g, 124.2 mmol) was added dropwise, and the mixture was extracted with addition of water and methylene chloride. The organic layer was dried with anhydrous sodium sulfate, concentrated to dryness under reduced pressure, and purified by recrystallization to give the title compound (2.13 g, 93.5%).

(ii) 6-(4-Methylbiphenyl-2-yl)pyridine-3-ylamine

N-(6-m-Tolylpyridine-3-yl)acetamide (0.50 g, 2.2 mmol) which was obtained by conventional acetylation of 6-m-tolylpyridine-3-ylamine synthesized in Example 3 (ii), diphenyliodonium tetrafluoroborate (1.22 g, 3.3 mmol) synthesized in (i) and palladium acetate (0.025 g, 0.11 mmol) were added to acetic acid (17 ml), and reacted at 100° C. for hour. The solvent was distilled off under reduced pressure, and the extraction was carried out with addition of saturated aqueous sodium bicarbonate and methylene chloride. The organic layer was dried with anhydrous sodium sulfate, and concentrated to dryness under reduced pressure. Methanol and 98% sulfuric acid were added to the products, and the hydrolysis was carried out at 70° C. for 2 hours. Methanol was distilled off under reduced pressure to give the title compound (0.34 g, 59.4%).

(iii) 4-Amino-3-[6-(4-methylbiphenyl-2-yl)pyridine-3-ylazo]naphthalene-1-sulfonic acid sodium salt The title compound was synthesized in a manner analogous to Example 1 (iii), except for replacing 2-phenyl-5-aminopyridine with 6-(4-methylbiphenyl-2-yl)pyridine-3-ylamine obtained in (ii).

$^1$H-NMR (DMSO-d6) δ[ppm]=9.14 (1H, d, J=2.4 Hz), 8.73 (1H, d, J=8.4 Hz), 8.47 (1H, d, J=8.1 Hz), 8.29 (1H, s), 8.16 (1H, dd, J=8.4, 2.4 Hz), 7.74 (2H, bs), 7.45-7.62 (3H, m), 7.20-7.33 (6H, m), 7.12 (1H, d, J=6.3 Hz), 6.99 (1H, d, J=8.4 Hz), 2.42 (3H, s)

$^{13}$C-NMR (DMSO-d6) δ[ppm]=158.8, 147.3, 146.6, 146.5, 140.9, 138.5, 137.5, 136.9, 132.2, 132.1, 131.1, 130.5, 129.5, 129.4, 129.1, 128.6, 128.3, 126.8, 125.6, 125.5, 125.4, 125.1, 124.2, 124.1, 116.1, 20.7

Example 48

Synthesis of 4-amino-3-[6-(4'-chloro-4-methylbiphenyl-2-yl)pyridine-3-ylazo]naphthalene-1-sulfonic acid sodium salt

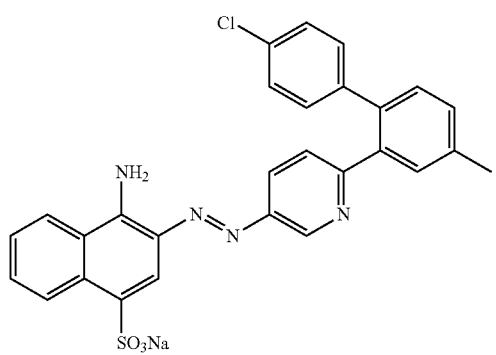

(i) Diacetoxy(2,4,6-trimethylphenyl)iodine (III)

1,3,5-Trimethyl-2-iodobenzene (20.0 g, 81.3 mmol) and acetic acid (720 ml) were charged and added portionwise with sodium perborate tetrahydrate (125 g, 813 mmol). The mixture was reacted for 3 hours, concentrated, and extracted with addition of water and methylene chloride. The organic layer was dried with anhydrous sodium sulfate, concentrated to dryness under reduced pressure, and purified by recrystallization to give the title compound (1.36 g, 37.3%).

(ii) (4-Chlorophenyl)(2,4,6-trimethylphenyl)iodonium tetrafluoroborate

4-Chlorophenylboronic acid (3.0 g, 8.2 mmol), methylene chloride (82 ml) and boron trifluoride ethyl ether complex (1.29 g, 9.1 mmol) were charged and cooled to 0° C. A solution of diacetoxy(2,4,6-trimethylphenyl)iodine (III) (3.0 g, 8.2 mmol) synthesized in (i) in methylene chloride (82 ml) was added dropwise, and the reaction was carried out at 0° C. for 1.5 hours. A saturated aqueous solution of sodium fluoroborate (18.1 g, 164.8 mmol) was added dropwise, and the mixture was extracted with addition of water and methylene chloride. The organic layer was dried with anhydrous sodium sulfate, concentrated to dryness under reduced pressure, and purified by recrystallization to give the title compound (3.36 g, 93.5%).

(iii) 6-(4'-Chloro-4-methylbiphenyl-2-yl)pyridine-3-ylamine

To acetic acid (17 ml), N-(6-m-tolylpyridine-3-yl)acetamide (0.50 g, 2.2 mmol), (4-chlorophenyl)(2,4,6-trimethylphenyl)iodonium tetrafluoroborate (1.13 g, 2.5 mmol) synthesized in (ii) and palladium acetate (0.025 g, 0.11 mmol) were added, and reacted at 100° C. for 1 hour. The solvent was distilled off under reduced pressure, and the residue was purified by column chromatography. The solvent was distilled off under reduced pressure. Methanol and 35% hydrochloric acid were added, and the hydrolysis was carried out at 65° C. for 2 hours. Methanol was distilled off under reduced pressure. Purification by column chromatography gave the title compound (0.47 g, 72.5%).

(iv) 4-Amino-3-[6-(4'-chloro-4-methylbiphenyl-2-yl)pyridine-3-ylazo]naphthalene-1-sulfonic acid sodium salt The title compound was synthesized in a manner analogous to Example 1 (iii), except for replacing 2-phenyl-5-aminopyridine with 6-(4'-chloro-4-methylbiphenyl-2-yl)pyridine-3-ylamine obtained in (iii).

$^1$H-NMR (DMSO-d6) δ[ppm]=9.13 (1H, d, J=2.4), 8.73 (1H, d, J=8.4), 8.43 (1H, d, J=8.1), 8.28 (1H, s), 8.23 (1H, dd, J=8.4, 2.4), 7.71 (NH$_2$, s), 7.61-7.55 (2H, m), 7.51-7.46 (1H, m), 7.36-7.33 (4H, m), 7.14 (2H, d, J=8.4), 7.08 (1H, d, J=8.4)

$^{13}$C-NMR (DMSO-d6) δ[ppm]=166.7, 158.5, 147.2, 146.4, 139.8, 138.5, 137.4, 136.2, 132.5, 132.1, 131.6, 131.2, 131.1, 130.4, 129.6, 129.2, 128.5, 128.3, 125.9, 125.4, 125.1, 124.2, 123.9, 116.1, 20.7

Example 49

Synthesis of 4-amino-3-[6-(4,3',5'-trimethylbiphenyl-2-yl)pyridine-3-ylazo]naphthalene-1-sulfonic acid sodium salt

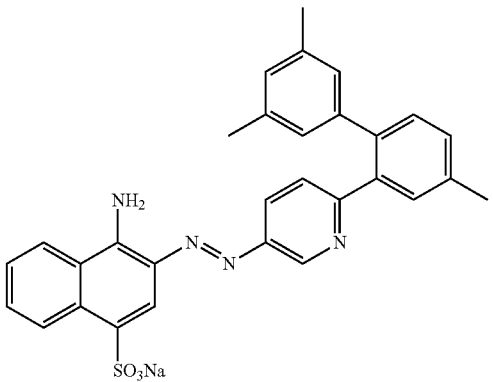

(i) (3,5-Dimethylphenyl)(2,4,6-trimethylphenyl)iodonium tetrafluoroborate

The title compound was obtained in a manner analogous to Example 48 (ii), except for replacing 4-chlorophenylboronic acid with 3,5-dimethylphenylboronic acid.

(ii) 6-(4,3',5'-Trimethylbiphenyl-2-yl)pyridine-3-ylamine

The title compound was obtained in a manner analogous to Example 48 (iii), except for replacing (4-chlorophenyl)(2,4,6-trimethylphenyl) iodonium tetrafluoroborate with (3,5-dimethylphenyl)(2,4,6-trimethylphenyl)iodonium tetrafluoroborate obtained in (i).

(iii) 4-Amino-3-[6-(4,3',5'-trimethylbiphenyl-2-yl)pyridine-3-ylazo]naphthalene-1-sulfonic acid sodium salt The title compound was synthesized in a manner analogous to Example 1 (iii), except for replacing 2-phenyl-5-aminopyridine with 6-(4,3',5'-trimethylbiphenyl-2-yl)pyridine-3-ylamine obtained in (ii).

$^1$H-NMR (DMSO-d6) δ[ppm]=9.16 (1H, d, J=2.4), 8.72 (1H, d, J=8.4), 8.44 (1H, d, J=8.4), 8.27 (1H, s), 8.18 (1H, dd, J=8.4, 2.4), 7.69 (NH$_2$, s), 7.61-7.55 (2H, m), 7.50-7.45 (1H, m), 7.30 (2H, s), 6.99 (1H, d, J=8.4), 6.86 (1H, s), 6.73 (2H, s), 2.41 (3H, s), 2.15 (6H, s)

$^{13}$C-NMR (DMSO-d6) δ[ppm]=166.8, 158.9, 147.2, 146.5, 140.8, 138.4, 137.7, 137.2, 136.7, 132.4, 132.1, 131.0, 130.4, 129.4, 129.2, 128.5, 128.3, 128.2, 127.2, 125.4, 125.3, 125.1, 124.2, 123.9, 116.0, 20.9, 20.7

Example 50

Synthesis of 4-amino-3-[6-(3'-chloro-4-methylbiphenyl-2-yl)pyridine-3-ylazo]naphthalene-1-sulfonic acid sodium salt

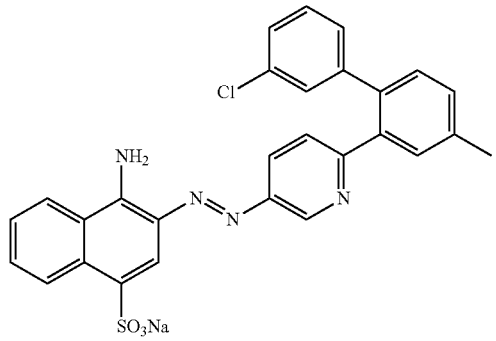

(i) (3-Chlorophenyl)(2,4,6-trimethylphenyl)iodonium tetrafluoroborate

The title compound was obtained in a manner analogous to Example 48 (ii), except for replacing 4-chlorophenylboronic acid with 3-chlorophenylboronic acid.

(ii) 6-(3'-Chloro-4-methylbiphenyl-2-yl)pyridine-3-ylamine

The title compound was obtained in a manner analogous to Example 48 (iii), except for replacing (4-chlorophenyl)(2,4,6-trimethylphenyl)iodonium tetrafluoroborate with (3-chlorophenyl)(2,4,6-trimethylphenyl)iodonium tetrafluoroborate obtained in (i).

(iii) 4-Amino-3-[6-(3'-chloro-4-methylbiphenyl-2-yl)pyridine-3-ylazo]naphthalene-1-sulfonic acid sodium salt The title compound was synthesized in a manner analogous to Example 1 (iii), except for replacing 2-phenyl-5-aminopyridine with 6-(3'-chloro-4-methylbiphenyl-2-yl)pyridine-3-ylamine obtained in (ii).

$^1$H-NMR (DMSO-d6) δ[ppm]=9.12 (1H, d, J=2.4), 8.72 (1H, d, J=8.4), 8.45 (1H, d, J=8.4), 8.27 (1H, s), 8.24 (1H, dd, J=8.7, 2.4), 7.74 (NH$_2$, s), 7.61-7.55 (2H, m), 7.50-7.45 (1H, m), 7.36 (2H, s), 7.31-7.22 (3H, m), 7.00 (1H, d, J=6.6), 2.43 (3H, s)

$^{13}$C-NMR (DMSO-d6) δ[ppm]=166.9, 158.5, 147.3, 146.6, 146.3, 143.1, 138.6, 137.6, 136.0, 132.9, 132.4, 132.1, 131.1, 130.5, 130.0, 129.6, 129.2, 128.9, 128.5, 128.2, 126.7, 126.0, 125.4, 125.1, 124.2, 124.0, 116.1, 20.7

Example 51

Synthesis of 4-amino-3-[6-(2,6-dimethylphenyl)pyridine-3-ylazo]naphthalene-1-sulfonic acid sodium salt

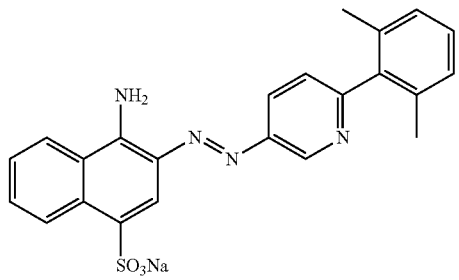

(i) 2-(2,6-Dimethylphenyl)-5-nitropyridine

2-Chloro-5-nitropyridine (1.0 g, 6.31 mmol), 2,6-dimethylphenylboronic acid (1.42 g, 9.47 mmol) and bis(di-tert-butyl(4-dimethylaminophenylphosphine)dichloropalladium (II) (0.044 g, 0.062 mmol) were added to 1,2-dimethoxyethan (32 ml), degassed and purged with nitrogen three times under reduced pressure. Under nitrogen atmosphere the mixture was stirred at room temperature for 30 minutes, 1M aqueous sodium carbonate (12 ml) was poured in, and the temperature was raised to 80° C. After the reaction at 80° C. for 3 hours, the mixture was cooled to room temperature and extracted with addition of ethyl acetate and water. The organic layer was dried with anhydrous sodium sulfate and concentrated under reduced pressure. Purification by column chromatography gave the title compound (1.41 g, 98.1%).

(ii) 6-(2,6-Dimethylphenyl)pyridine-3-ylamine

The title compound was synthesized in a manner analogous to Example 1 (ii), except for replacing 2-phenyl-5-nitropyridine with 2-(2,6-dimethylphenyl)-5-nitropyridine obtained in (i).

(iii) 4-Amino-3-[6-(2,6-dimethylphenyl)pyridine-3-ylazo]naphthalene-1-sulfonic acid sodium salt The title compound was synthesized in a manner analogous to Example 1 (iii), except for replacing 2-phenyl-5-aminopyridine with 6-(2,6-dimethylphenyl)pyridine-3-ylamine obtained in (ii).

¹H-NMR (DMSO-d6) δ[ppm]=9.24 (1H, d, J=2.1 Hz), 8.76 (1H, dd, J=8.6, 0.9 Hz), 8.44-8.48 (2H, m), 8.33 (1H, s), 7.80 (2H, bs), 7.58-7.63 (1H, m), 7.47-7.53 (1H, m), 7.45 (1H, dd, J=8.4, 0.6 Hz), 7.13-7.24 (3H, m), 2.04 (6H, s)

¹³C-NMR (DMSO-d6) δ[ppm]=159.3, 147.0, 146.7, 145.7, 140.2, 135.3, 132.4, 132.1, 129.2, 128.5, 128.3, 127.8, 127.4, 127.2, 125.0, 124.2, 123.9, 116.6, 20.0

Example 52

Synthesis of 4-amino-3-[6-(3-formyl-2-isopropoxy-5-methylphenyl)pyridine-3-ylazo]naphthalene-1-sulfonic acid sodium salt

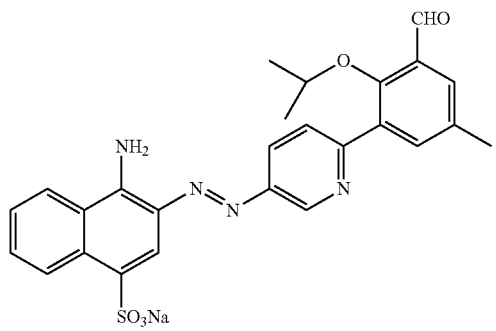

(i) 2-Isopropoxy-5-methyl-3-(5-nitropyridine-2-yl)benzaldehyde

2-Chloro-5-nitropyridine (0.28 g, 1.76 mmol), 3-formyl-2-isopropoxy-5-methylphenylboronic acid (0.78 g, 3.52 mmol) and bis(di-tert-butyl(4-dimethylaminophenylphosphine)dichloropalladium(II) (0.012 g, 0.02 mmol) were added to 1,2-dimethoxyethan (9 ml), degassed and purged with nitrogen three times under reduced pressure. Under nitrogen atmosphere the mixture was stirred at room temperature for 30 minutes, 1M aqueous sodium carbonate (9 ml) was poured in, and the temperature was raised to 80° C. After the reaction at 80° C. for 23 hours, the mixture was cooled to room temperature and crystallized with addition of water. The crystallized crystals were filtered to give the title compound (0.49 g, 92.5%).

(ii) 3-(5-Aminopyridine-2-yl)-2-isopropoxy-5-methylbenzaldehyde

The title compound was synthesized in a manner analogous to Example 1 (ii), except for replacing 2-phenyl-5-nitropyridine with 2-isopropoxy-5-methyl-3-(5-nitropyridine-2-yl)benzaldehyde obtained in (i).

(iii) 4-Amino-3-[6-(3-formyl-2-isopropoxy-5-methylphenyl)pyridine-3-ylazo]naphthalene-1-sulfonic acid sodium salt The title compound was synthesized in a manner analogous to Example 1 (iii), except for replacing 2-phenyl-5-aminopyridine with 3-(5-aminopyridine-2-yl)-2-isopropoxy-5-methylbenzaldehyde obtained in (ii).

¹H-NMR (DMSO-d6) δ[ppm]=10.39 (1H, s), 9.27 (1H, d, J=2.4 Hz), 8.75 (1H, d, J=8.4 Hz), 8.52 (1H, dd, J=8.4, 2.4 Hz), 8.46 (1H, d, J=8.4 Hz), 8.31 (1H, s), 8.01 (1H, d, J=8.4 Hz), 7.94 (1H, d, J=2.1 Hz), 7.81 (2H, bs), 7.64 (1H, d, J=2.4 Hz), 7.59 (1H, d, J=8.4 Hz), 7.48-7.53 (1H, m), 3.80-3.88 (1H, m), 2.35 (3H, s), 1.01-1.13 (6H, m)

¹³C-NMR (DMSO-d6) δ[ppm]=190.3, 156.1, 154.8, 147.2, 146.7, 138.0, 134.4, 133.7, 132.6, 132.2, 130.4, 129.3, 128.6, 128.4, 128.3, 126.4, 125.1, 124.8, 124.2, 123.9, 116.4, 78.3, 21.4, 20.2

Example 53

Synthesis of 4-amino-3-[6-(3-formyl-2-butoxy-5-methylphenyl)pyridine-3-ylazo]naphthalene-1-sulfonic acid sodium salt

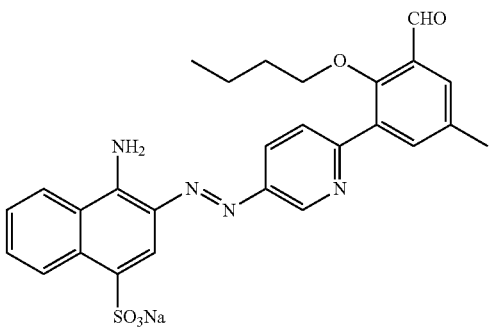

(i) 2-Butoxy-5-methyl-3-(5-nitropyridine-2-yl)benzaldehyde

The title compound was synthesized in a manner analogous to Example 52(i), except for replacing 2-chloro-5-nitropyridin with 2-chloro-5-nitropyridine, and replacing 3-formyl-2-isopropoxy-5-methylphenylboronic acid with 3-formyl-2-butoxy-5-methylphenylboronic acid.

(ii) 3-(5-Aminopyridine-2-yl)-2-butoxy-5-methylbenzaldehyde

The title compound was synthesized in a manner analogous to Example 1 (ii), except for replacing 2-phenyl-5-nitropyridine with 2-butoxy-5-methyl-3-(5-nitropyridine-2-yl)benzaldehyde obtained in (i).

(iii) 4-Amino-3-[6-(3-formyl-2-butoxy-5-methylphenyl)pyridine-3-ylazo]naphthalene-1-sulfonic acid sodium salt The title compound was synthesized in a manner analogous to Example 1 (iii), except for replacing 2-phenyl-5-aminopyridine with 3-(5-aminopyridine-2-yl)-2-butoxy-5-methylbenzaldehyde obtained in (ii).

¹H-NMR (DMSO-d6) δ[ppm]=10.4 (1H, s), 9.27 (1H, d, J=2.4 Hz), 8.75 (1H, d, J=8.1 Hz), 8.51 (1H, dd, J=8.6, 1.8 Hz), 8.46 (1H, d, J=8.1 Hz), 8.31 (1H, s,), 7.95-8.03 (2H, m), 7.81 (2H, bs), 7.58-7.64 (2H, m), 7.47-7.52 (1H, m), 3.71 (2H, t, J=6.5 Hz), 2.41 (3H, s), 1.53-1.89 (2H, m), 1.24-1.36 (2H, m), 0.78 (3H, t, J=7.2 Hz)

¹³C-NMR (DMSO-d6) δ[ppm]=189.8, 157.9, 154.2, 147.3, 147.1, 146.5, 137.9, 133.9, 133.8, 132.7, 132.2, 129.4, 129.3, 128.6, 128.5, 128.4, 126.6, 125.0, 124.6, 124.2, 123.9, 116.4, 76.3, 31.3, 20.2, 18.5, 13.6

VCP-Inhibitory Activity

Biological Example 1

Mouse VCP cDNA was added with a DNA sequence corresponding to histidine tag at the amino-terminal, subcloned into a baculovirus vector pVL1392 (BD Bioscience), and expressed in Sf-9 insect cells. The protein was purified with a nickel column (GE Healthcare). The concentration of the protein was adjusted to 0.25-0.5 μg/ml and the protein was stored in a solution containing 50 mM TrisCl pH 8.0, 5 mM EDTA, 10% glycerol, and 15 mM DTT.

The ATPase activity was determined as follows. 500 ng of the purified VCP was mixed with 100 μM [γ-$^{32}$P]ATP (18.5 GBq/mmol) and the test substance in 20 μL of ATPase buffer (20 mM HEPES (pH7.4), 50 mM KCl, 5 mM $MgCl_2$, 15 mM DTT), and incubated at 37° C. for 10 minutes.

The enzyme reaction was stopped with addition of 200 μL of an ice-cold solution containing 7% TCA and 1 mM $K_2HPO_4$. 50μ of a solution containing 3.75% ammonium molybdate and 0.02M tungstate silicic/3 $NH_2SO_4$ was added, followed by 300 μL of n-butylacetic acid, and then the liberated phosphate was extracted into the organic layer. The reaction tube was centrifuged for 5 minutes at 20,000 g to separate the aqueous layer and the organic layer, 200 μL of the organic layer was taken, and the beta ray radiated from the liberated phosphate was quantified with liquid scintillation counter.

By measuring the ATPase activity in the presence of the test substance at various concentrations, ATPase inhibitory activity of the test substance was measured. $IC_{50}$ of the each test substance was calculated by applying the measured values to the equation below using GraphPad Prism (GraphPad Software).

$$Y = \text{Bottom} + (\text{Top} - \text{Bottom})/(1 + 10^{((\log IC_{50} - X))})$$

X: Logarithm of the concentration of the test substance
Y: ATPase activity in the presence of test substance
Bottom: Value when the activity was inhibited to the maximum
Top: ATPase activity in the absence of the test substance $IC_{50}$ values (nM) of the compounds of Examples are shown in the table below.

TABLE 2

| Ex. | IC50 |
| --- | --- |
| 1 | 229 |
| 2 | 430 |
| 3 | 188 |
| 4 | 149 |
| 5 | 116 |
| 6 | 178 |
| 7 | 189 |
| 8 | 136 |
| 9 | 178 |
| 10 | 170 |
| 11 | 445 |
| 12 | 197 |
| 13 | 324 |
| 14 | 540 |
| 15 | 300 |
| 16 | 304 |
| 17 | 145 |
| 18 | 416 |
| 19 | 287 |
| 20 | 428 |
| 21 | 301 |
| 22 | 274 |
| 23 | 632 |
| 24 | 726 |

TABLE 2-continued

| Ex. | IC50 |
| --- | --- |
| 25 | 328 |
| 26 | 769 |
| 27 | 584 |
| 28 | 524 |
| 29 | 2,750 |
| 30 | 589 |
| 31 | 127 |
| 32 | 330 |
| 33 | 139 |
| 34 | 246 |
| 35 | 1,390 |
| 36 | 320 |
| 37 | 380 |
| 38 | 250 |
| 39 | 843 |
| 40 | 856 |
| 41 | 807 |
| 42 | 324 |
| 43 | 378 |
| 44 | 232 |
| 45 | 130 |
| 46 | 712 |
| 47 | 257 |
| 48 | 796 |
| 49 | 3,998 |
| 50 | 924 |
| 51 | 112 |
| 52 | 212 |
| 53 | 161 |

Pharmacological Test (Glaucoma)

Figure 2:
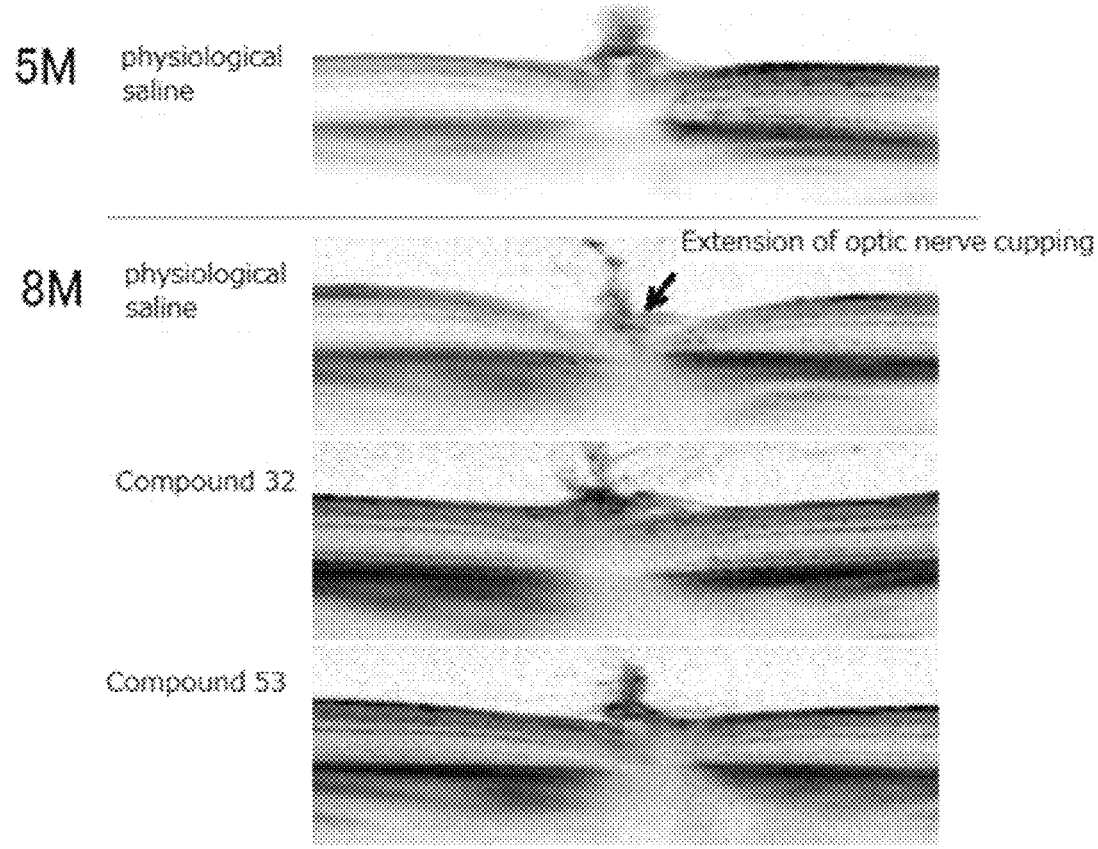
FIG. 2: From the top, the OCT images of the optic nerve heads of the 5-month-old (5M) DBA/2J mice administered with the physiological saline and the 8-month-old (8M) DBA/2J mice administered with the physiological saline, Compound 32 and Compound 53.
Figure 3:
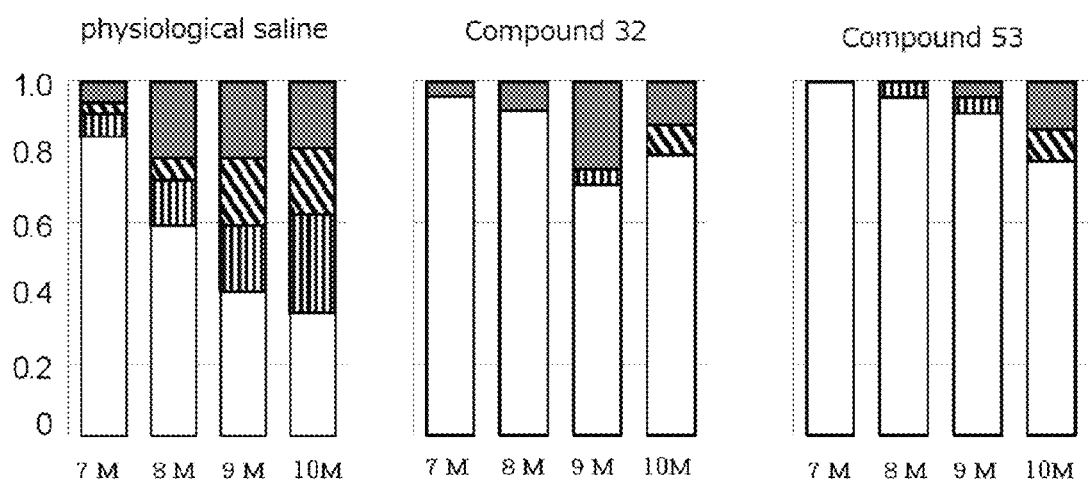
FIG. 3: The evaluation of the optic nerve cupping in DBA/2J mice (7M, 8M, 9M and 10M) administered with the physiological saline, Compound 32 and Compound 53. Longitudinal axis: ratio. Filled: not evaluable, diagonal lines: cupping extends across Bruch membrane, vertical lines: cupping extends to more than ½ of the thickness of the retina, blanc: cupping extends to ½ or less of the thickness of the retina.
Figure 4:
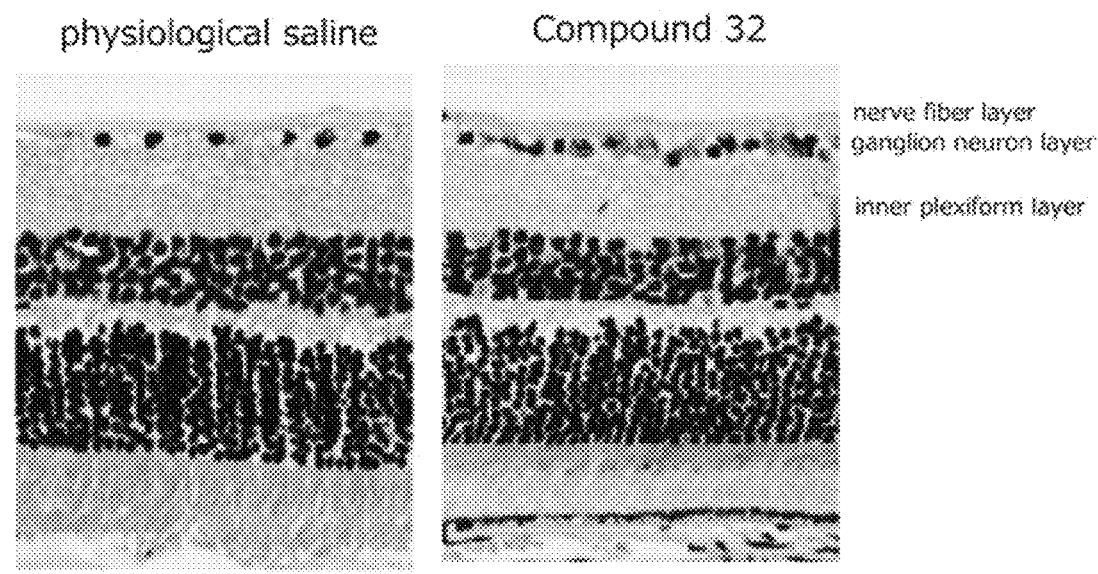
FIG. 4: The micrographs of the retinae from the 10-month-old DBA/2J mice administered with the physiological saline (left) and Compound 32 (right).
Figure 5:
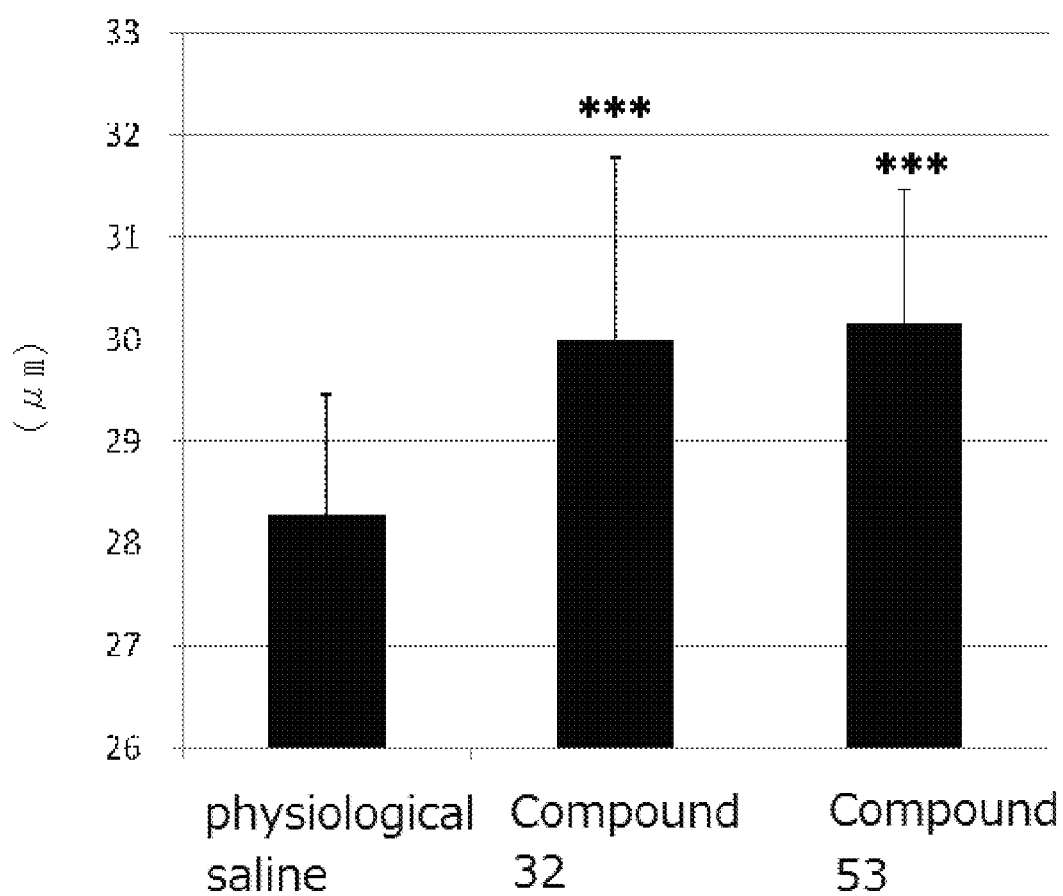
FIG. 5: The thickness of the nerve fiber layer of the 7-month-old DBA/2J mice administered with the physiological saline, Compound 32 and Compound 53. *** means significant difference (P=0.001 for the physiological saline vs Compound 32, P<0.001 for the physiological saline vs Compound 53, Dunnet's test).
Figure 6:
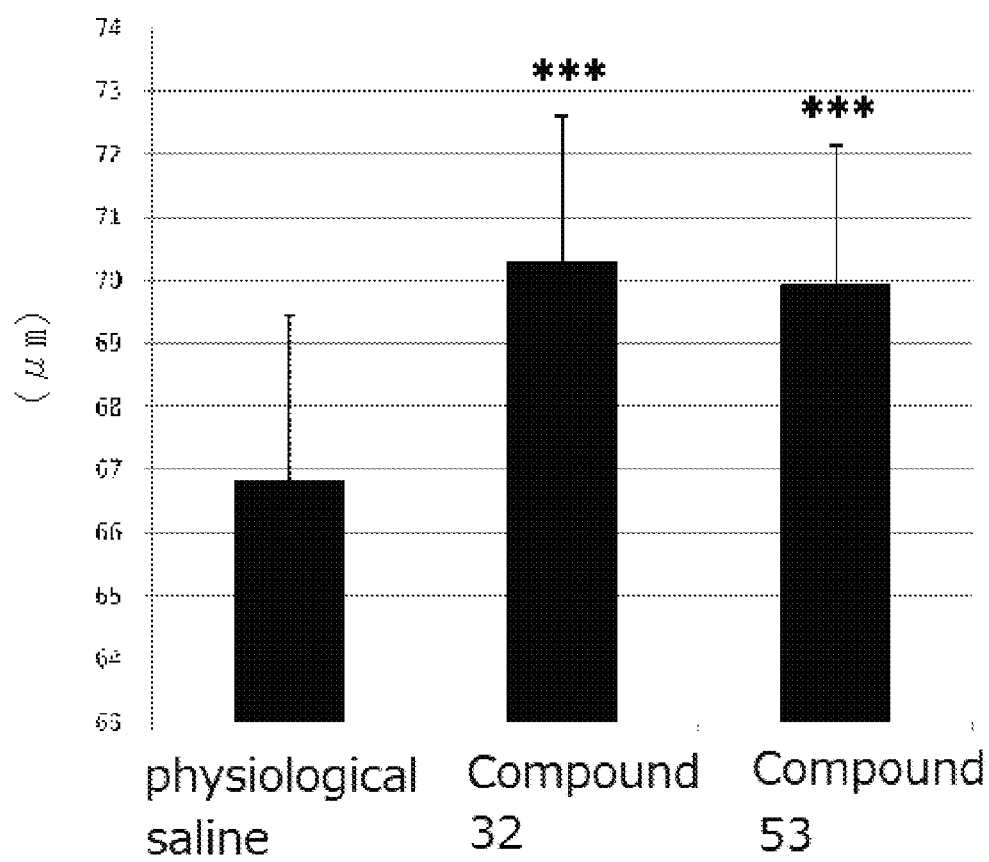
FIG. 6: The thickness of the inner retinal layer from the 8-month-old DBA/2J mice administered with the physiological saline, Compound 32 and Compound 53. *** means significant difference (P<0.001 for the physiological saline vs Compound 32, P<0.001 for the physiological saline vs Compound 53, Dunnet's test).
Figure 7:
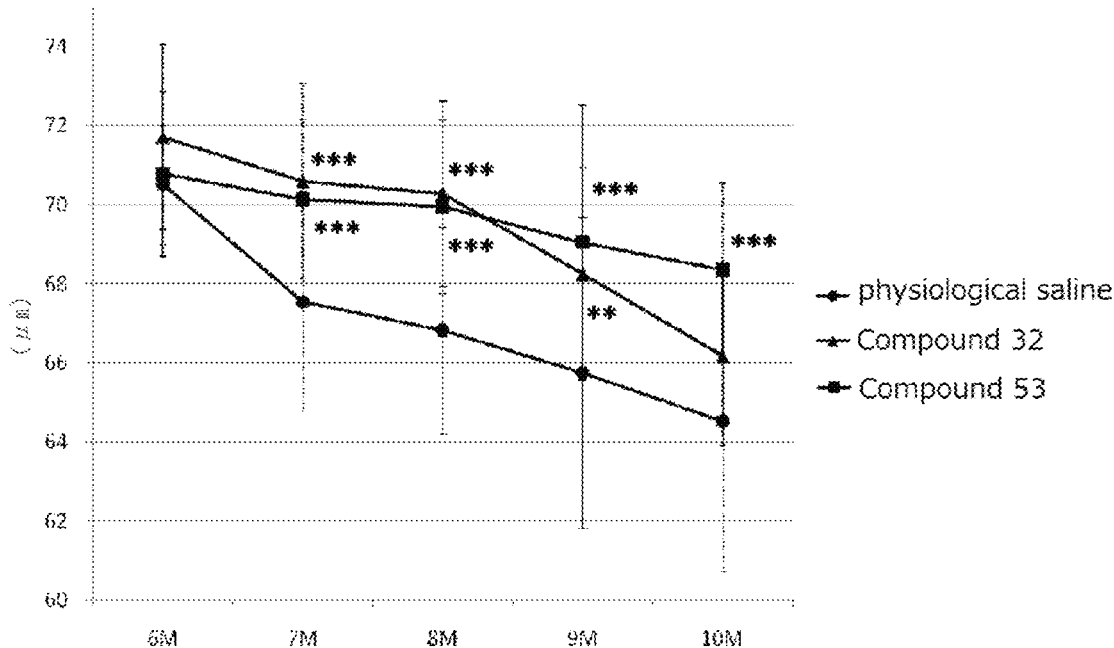
FIG. 7: The time course of the thickness of the inner retinal layer in the DBA/2J mice administered with the physiological saline, Compound 32 and Compound 53.

As a model of secondary angle-closure glaucoma, the DBA/2J mice (Anderson, M. G. et al; BMC Genetics (2001)) were employed. The mice were administered orally with 50 mg/kg/day of the compound of Synthetic Example 32 or 53 (Compound 32 or 53, respectively) daily after two months of age. The tomographs of retinae (n=22 to 32 eyes) were obtained in the 6, 7, 8, 9 and 10-month-old mice with the optical coherence tomography (OCT) (Multiline OCT, Heidelberg Engineering) (FIGS. 1 and 2: The OCT images of the retinae of the 8-month-old mice, FIG. 3: The evaluation of the optic nerve cupping in the 7 to 10-month-old mice). The mice in the control group were administered orally with the physiological saline. The eyeballs were enucleated at 10 months of age, and retinae were observed after hematoxylin-eosin (HE) staining (FIG. 4: The micrographs of retinae of the 8-month-old mice after HE staining). The thickness of the inner retinal layers and the nerve fiber layers was determined from the OCT images (FIG. 5: The thickness of the nerve fiber layers of the 7-month-old mice; FIG. 6: The thickness of the inner retinal layers of the 8-month-old mice; FIG. 7: The time course of the thickness of the inner retinal layers). The thickness of the inner retinal layer is a sum of the thickness of the nerve fiber and ganglion neuron layer and the inner plexiform layer.

According to the OCT images of the retinae of the 8-month-old mice (FIG. 1), the nerve fiber and ganglion neuron layers were well preserved in the mice administered with the compounds in comparison with the 5-month-old mice administered with the physiological saline which were known to have little progression of the disease, but in the mice from the control group administered with the physiological saline the nerve fiber and ganglion neuron layers were hardly observed. According to the OCT images of the optic nerve heads (FIG. 2) and the evaluation thereof (FIG. 3), the apparent optic nerve cupping (across Bruch membrane) was observed in the 7, 8, 9 and 10-month-old mice in the control group administered with physiological saline, whereas no apparent recess was observed in the mice administered with the compounds at the age until 7, 8 and 9 months (n=22 to 32 eyes). The thickness of the nerve fiber layer and the inner retinal layer determined from the OCT images was significantly thicker in the mice administered with the compounds (FIGS. 5 to 7).

In the sections of retinae of the 10-month-old mice (FIG. 4), shedding of the ganglion neurons and the thinning of the nerve fiber layer were observed in the control group administered with the physiological saline, whereas the ganglion neurons were well preserved and the nerve fiber layer was maintained relatively thick in the treated group.

Besides, the intraocular pressure was measured with Tono-Lab (M. E. Technica) tonometer under general anesthesia monthly from 2 months of age. The mean intraocular pressure at 4, 5, 6, 7 and 8 months of age was 13.6, 14.0, 11.3, 16.3 and 12.8 mmHg in the control group administered with the physiological saline, 13.0, 15.6, 12.0, 12.3 and 14.4 mmHg in the group administered with Compound 32, 14.6, 16.0, 12.8, 13.0 and 14.4 mmHg in the group administered with Compound 53. No significant difference in the intraocular pressure is observed among the groups (Dunnett's rank test). Thus, the effect of the agents does not depend on reduction of the intraocular pressure.

Figure 8:
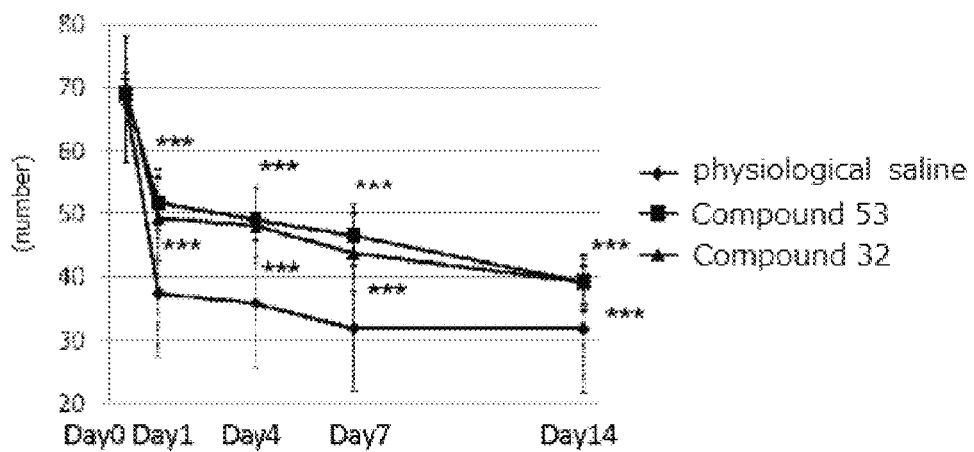
FIG. 8: The time course of the number of the ganglion neurons in the Thy1-CFP mice which were given the intravitreal injection of NMDA (2 nmol) and administered with the physiological saline, Compound 32 and Compound 53. The physiological saline or the compounds were administered orally.
Figure 9:
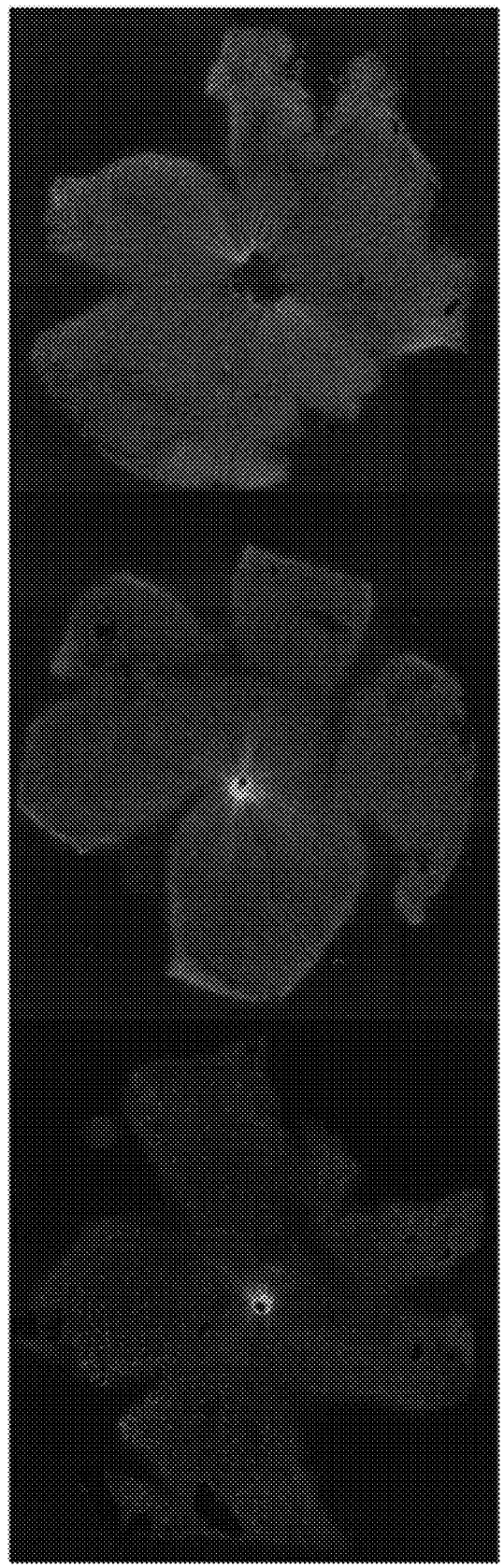
FIG. 9: The results of the flat-mounted retinae from the Thy1-CFP mice which were given the intravitreal injection of NMDA (2 nmol) and administered with the physiological saline, Compound 32 and Compound 53, at one day after the injection.
Figure 10:
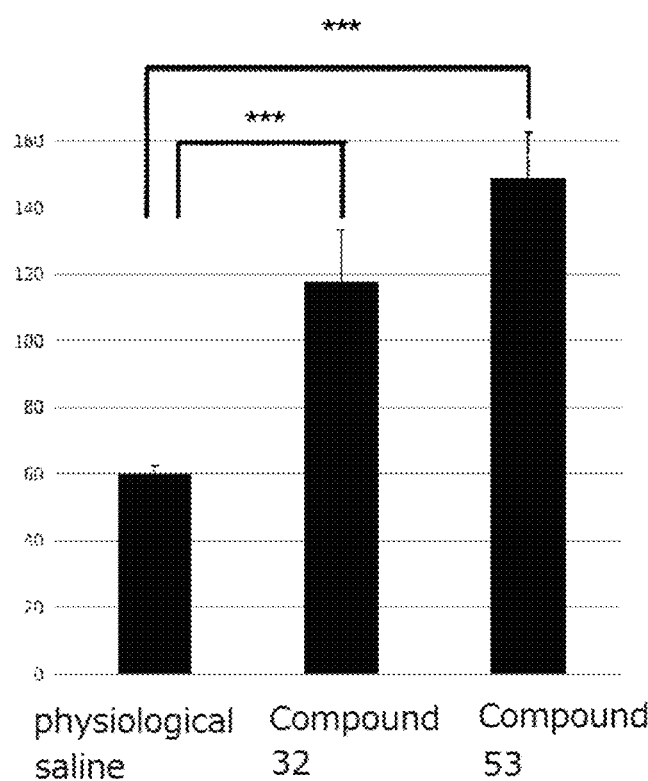
FIG. 10: The number of the ganglion neurons (the flat-mounted retinae) in Thy1-CFP mice which were given the intravitreal injection of NMDA (2 nmol) and administered with the physiological saline, Compound 32 and Compound 53, at one day after the injection. *** means significant difference (P=0.002 for the physiological saline vs Compound 32, P=0.003 for the physiological saline vs Compound 53, Dunnet's test).

As a mouse model of glaucoma, the mice of B6.Cg-Tg (Thy 1-CFP) 23Jrs/J (purchased from Jackson Laboratory (Bar Harbor, Me.)) which express CFP-fluorescent protein in the ganglion neurons were administered with NMDA (2 nmol) by the intravitreal injection. The mice were administered orally with 50 mg/kg/day of the compounds daily from one week before the NMDA injection. The administration of the compounds was continued after the injection. The number of the ganglion neurons was counted just before the NMDA injection (day 0), and at day 1, 4, 7 and 14 after the injection (n=15 eyes (the physiological saline), 26 eyes (Compound 32), 17 eyes (Compound 53)) (FIG. 8). In the group of the mice administered with the compounds the number of the ganglion neurons was maintained better than the control group, indicating that the damage of the ganglion neurons was significantly suppressed and/or delayed (Dunnett's rank test). Similarly, the eyeballs were enucleated from the mice at one day after NMDA injection and the flat-mounted retinae were observed (FIG. 9) to count the number of the ganglion neurons (FIG. 10, n=5 eyes (the physiological saline), 4 eyes (Compound 32) and 5 eyes (Compound 53)). The number of the ganglion neurons in the mice administered with Compound 32 or Compound 53 was significantly more than that in the mice administered with the physiological saline (P=0.002 for the physiological saline vs Compound 32, P=0.003 for the physiological saline vs Compound 53, Dunnett's rank test).

Figure 11:
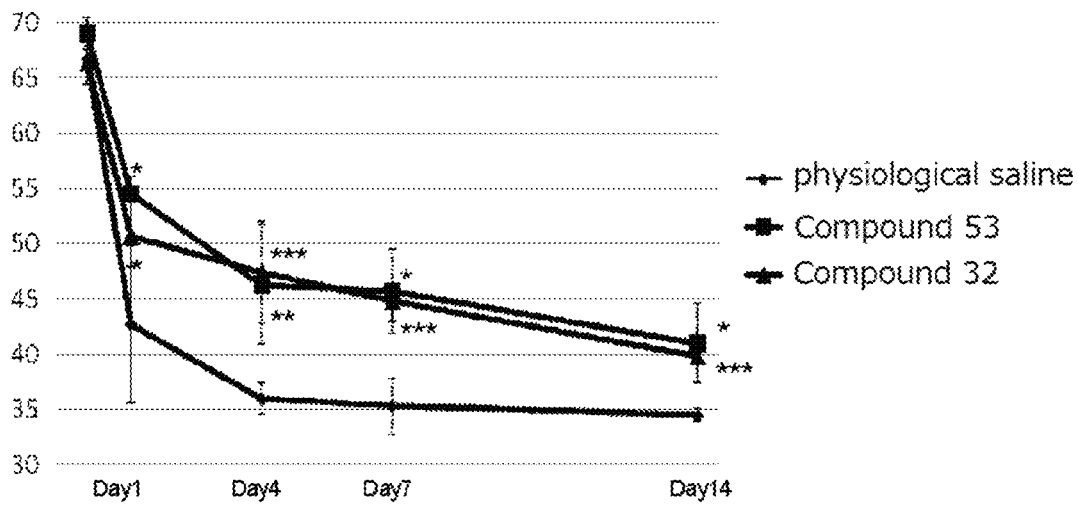
FIG. 11: The time course of the number of the ganglion neurons in the mice which were given the intravitreal injection of NMDA and administered with the physiological saline, Compound 32 and Compound 53. The physiological saline or the compounds were administered subconjunctivally and intravitreally.

The number of the ganglion neurons was counted just before the NMDA injection (day 0), and at day 1, 4, 7 and 14 after the injection in a manner analogous to the Thy 1-CFP mice model described above, except for replacing the oral administration with the subconjunctival administration 5 days before the NMDA injection, just before the injection (day 0) and at day 1, 2, 4 and 7 after the injection, and the intravitreal administration at the same time with the injection (day 0) (n=5 eyes (the physiological saline), 7 eyes (Compound 32), 5 eyes (Compound 53)) (FIG. 11). Analogously to the oral administration, in the group of the mice administered with the compounds subconjunctivally and intravitreally the number of the ganglion neurons was maintained better than the control group, indicating that the damage of the ganglion neurons was significantly suppressed and/or delayed.

Figure 12:
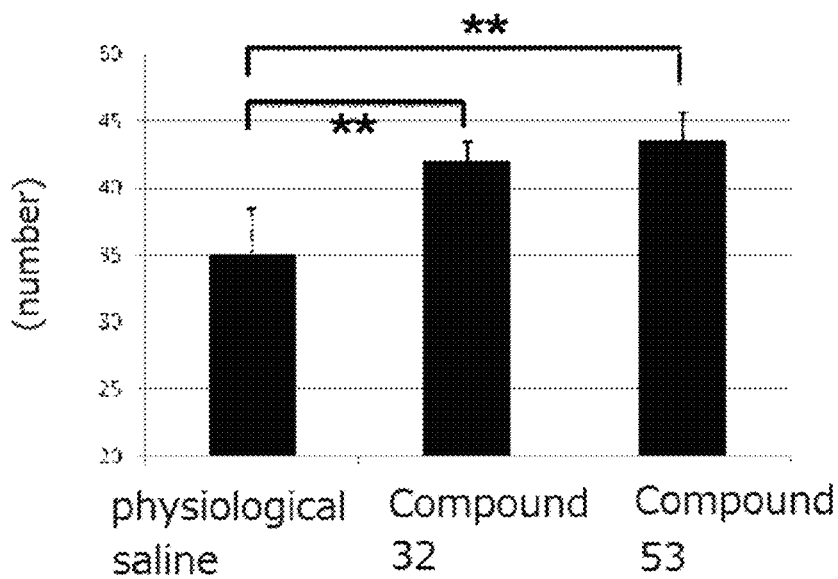
FIG. 12: The number of the ganglion neurons in the 21-day-old GLAST−/− mice administered with the physiological saline, Compound 32 and Compound 53. ** means significant difference (P=0.003 for the physiological saline vs each compound, t-test).

The GLAST-deficient (−/−) mice, a mouse model of normal tension glaucoma (The Journal of Clinical Investigation, Volume 17, Number 7, July 2007), were mated with the mice of B6.Cg-Tg (Thy 1-CFP) 23Jrs/J. The resulting GLAST-deficient (−/−)/Thy 1-CFP mice were administered intraperitoneally with 50 mg/kg/day of the compounds daily after 7 days of age. The CFP images were obtained at 21 days of age and the number of the ganglion neurons was determined. For the control group the physiological saline was used. The results are shown in FIG. 12. The number of the ganglion neurons in the mice administered with Compound 32 or Compound 53 was significantly more than that in the mice administered with the physiological saline (P=0.003, t-test).

Figure 13:
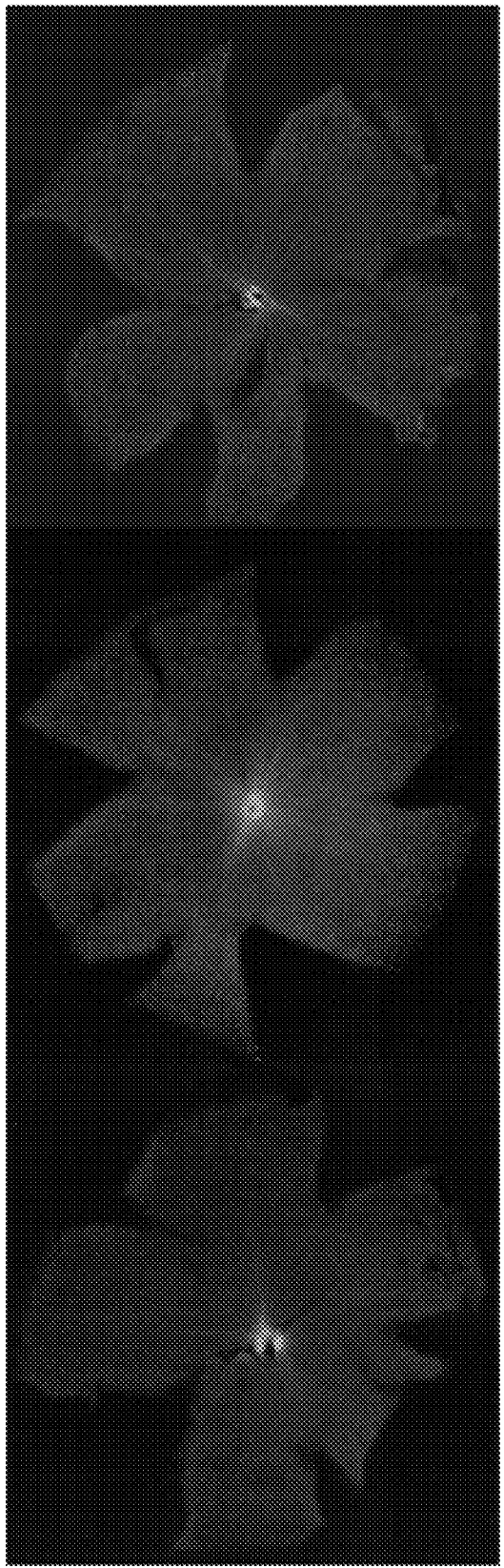
FIG. 13: The results of the flat-mounted retinae from the 12-month-old GLAST+/− mice administered with the physiological saline, Compound 32 and Compound 53.
Figure 14:
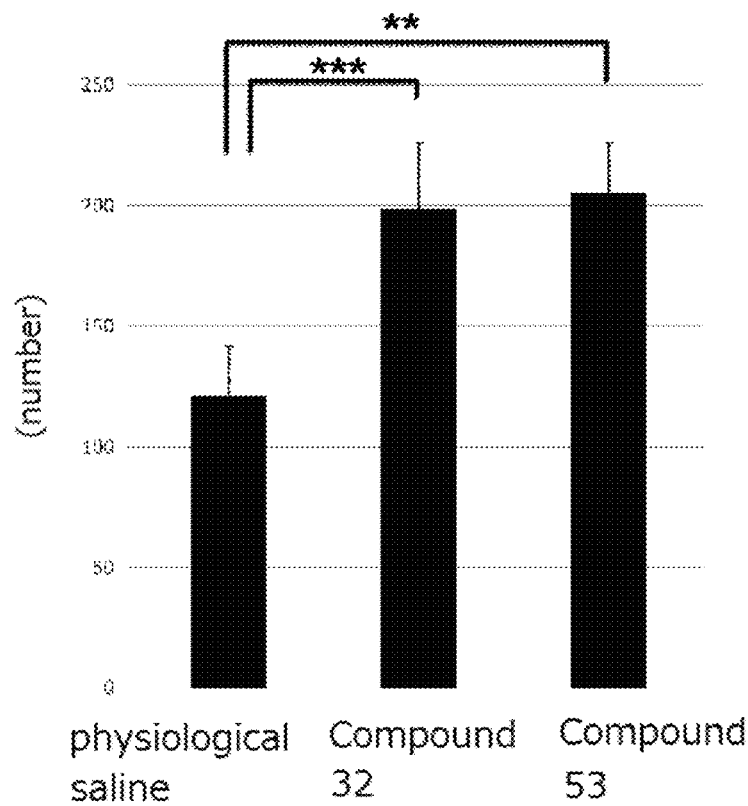
FIG. 14: The number of the ganglion neurons (the flat-mounted retinae) in the 12-month-old GLAST+/− mice administered with the physiological saline, Compound 32 and Compound 53. ** means significant difference (P=0.002 for the physiological saline vs Compound 32, P=0.005 for the physiological saline vs Compound 53, Dunnet's test).

The GLAST-deficient (+/−) mice, a mouse model of normal tension glaucoma with slow progression (The Journal of Clinical Investigation, Volume 17, Number 7, July 2007), were mated with the mice of B6.Cg-Tg (Thy 1-CFP) 23Jrs/J. The resulting GLAST-deficient (+/−)/Thy 1-CFP mice were administered with 50 mg/kg/day of the compounds daily from 7 to 49 days of age intraperitoneally, subsequently daily until 4 months of age via a stomach tube, and then until 12 months of age 3 times per week orally and daily in drinking-water. The eyeballs were enucleated from the 12-month-old mice and the flat-mounted retinae were observed (FIG. 13) to count the number of the ganglion neurons (FIG. 14). For the control group the physiological saline was used. The number of the ganglion neurons in the mice administered with Compound 32 or Compound 53 was significantly more than that in the mice administered with the physiological saline (P=0.002 for Compound 32, P=0.003 for Compound 53, Dunnett's rank test)

Pharmacological Test (Retinitis Pigmentosa)

Figure 15:
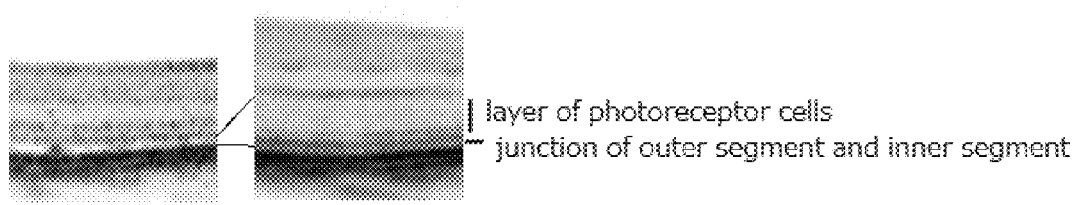
FIG. 15: The OCT images of the 25-day-old rd10 mice administered with the physiological saline and Compound 32.
Figure 16:
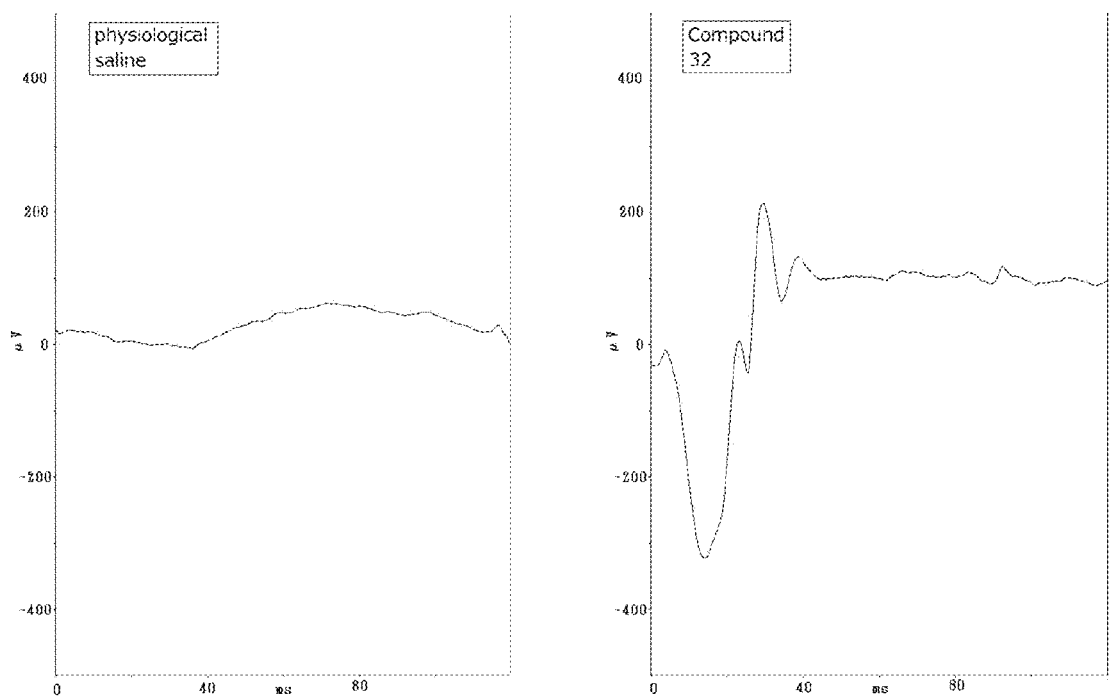
FIG. 16: The electroretinogram of the 25-day-old rd10 mice administered with the physiological saline and Compound 32.
Figure 17:
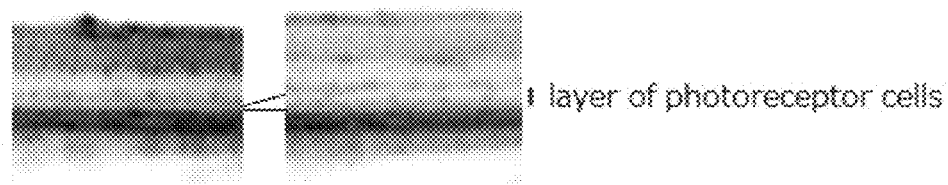
FIG. 17: The OCT images of the 29-day-old rd10 mice administered with the physiological saline and Compound 32.
Figure 18:
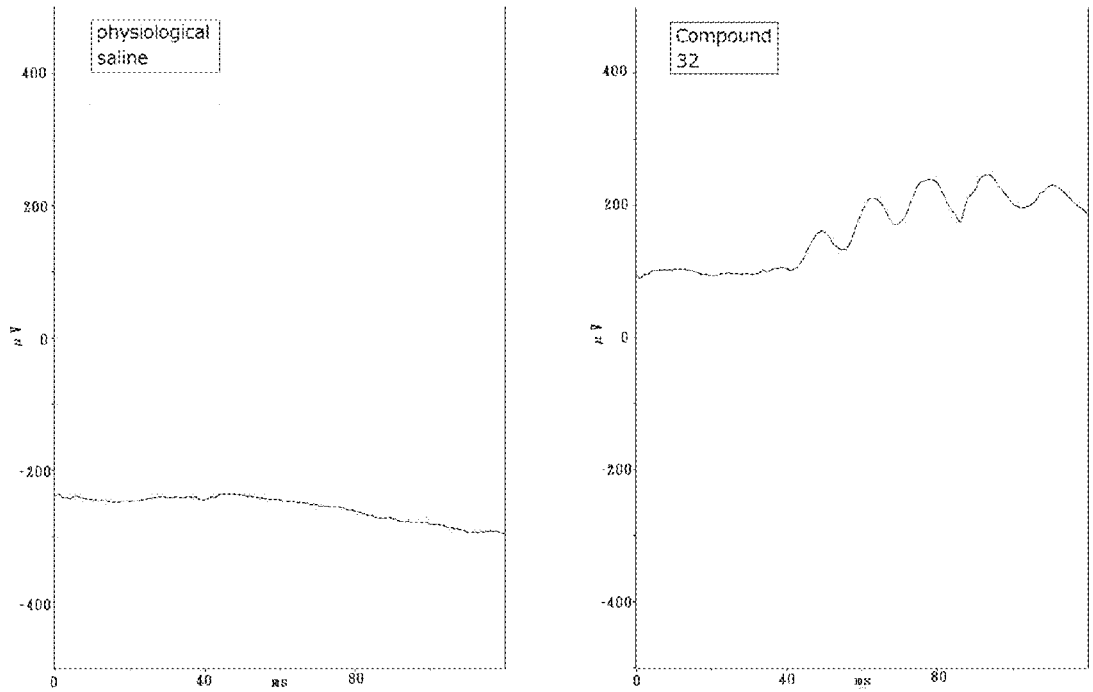
FIG. 18: The electroretinogram of the 29-day-old rd10 mice administered with the physiological saline and Compound 32.
Figure 19:
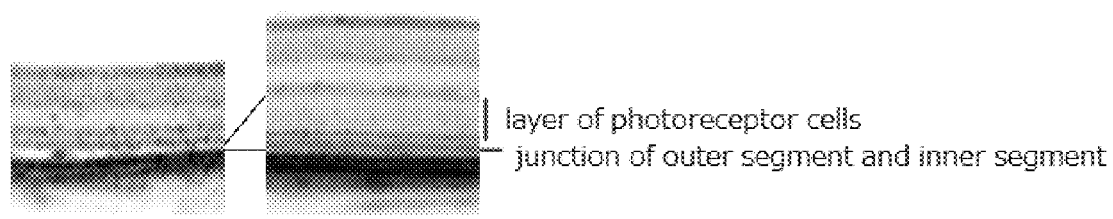
FIG. 19: The OCT images of the 25-day-old rd10 mice administered with the physiological saline and Compound 53.
Figure 20:
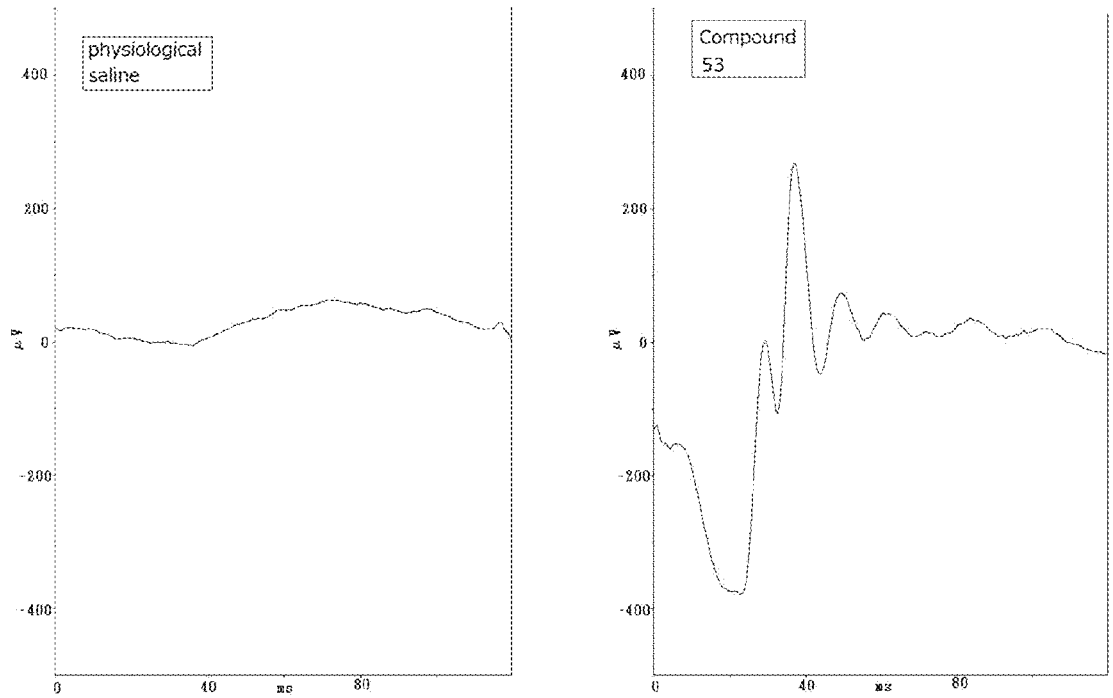
FIG. 20: The electroretinogram of the 25-day-old rd10 mice administered with the physiological saline and Compound 53.
Figure 21:
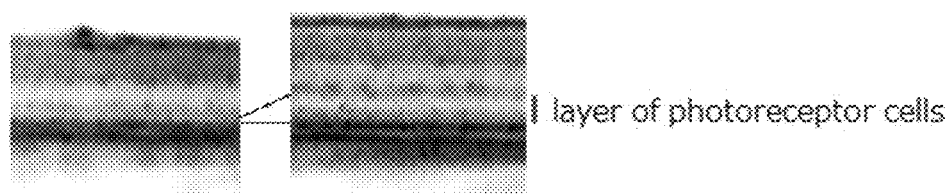
FIG. 21: The OCT images of the 29-day-old rd10 mice administered with the physiological saline and Compound 53.
Figure 22:
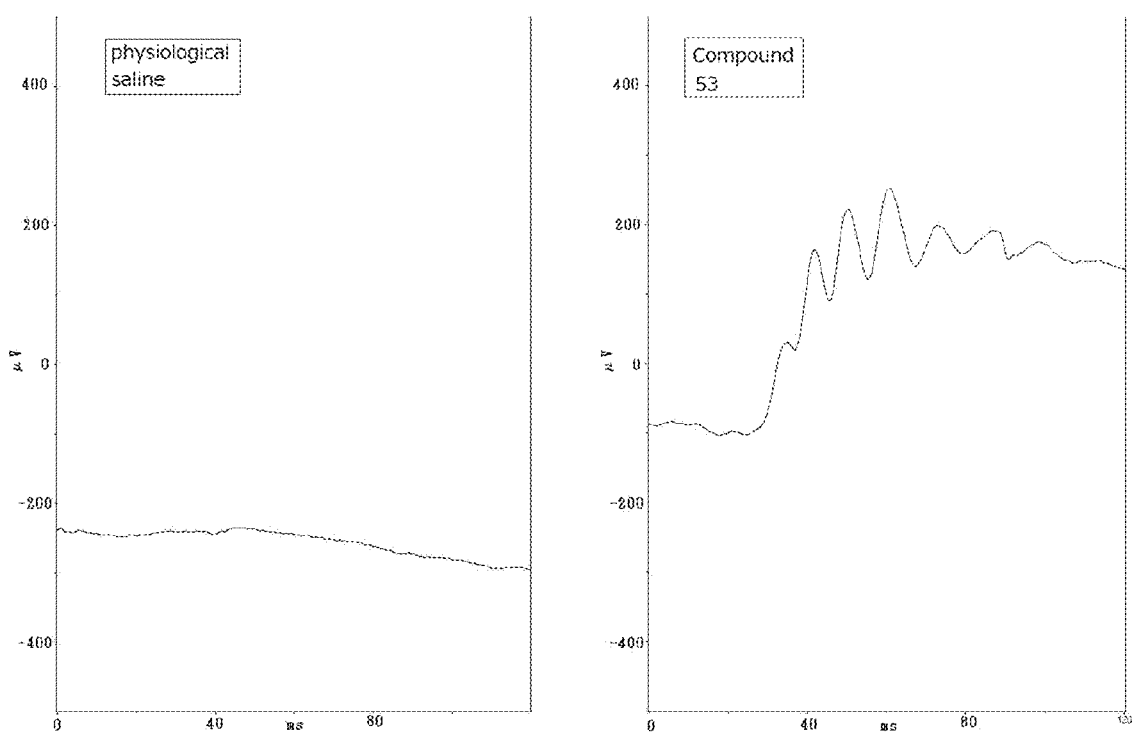
FIG. 22: The electroretinogram of the 29-day-old rd10 mice administered with the physiological saline and Compound 53.
Figure 23:
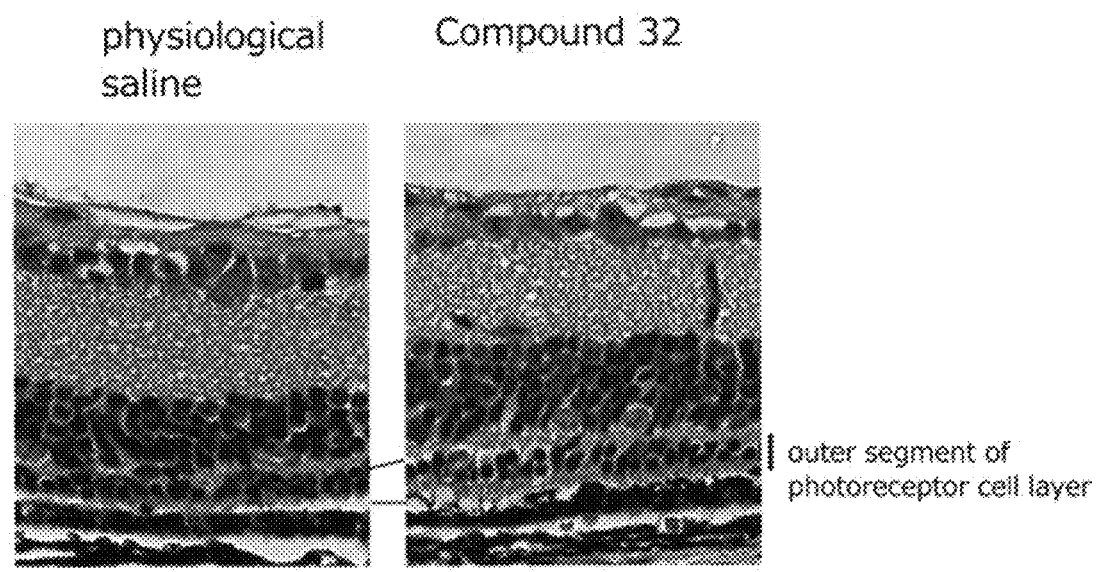
FIG. 23: The HE-stained micrographs of the retinae of the 33-day-old rd10 mice administered with the physiological saline and Compound 32.
Figure 24:
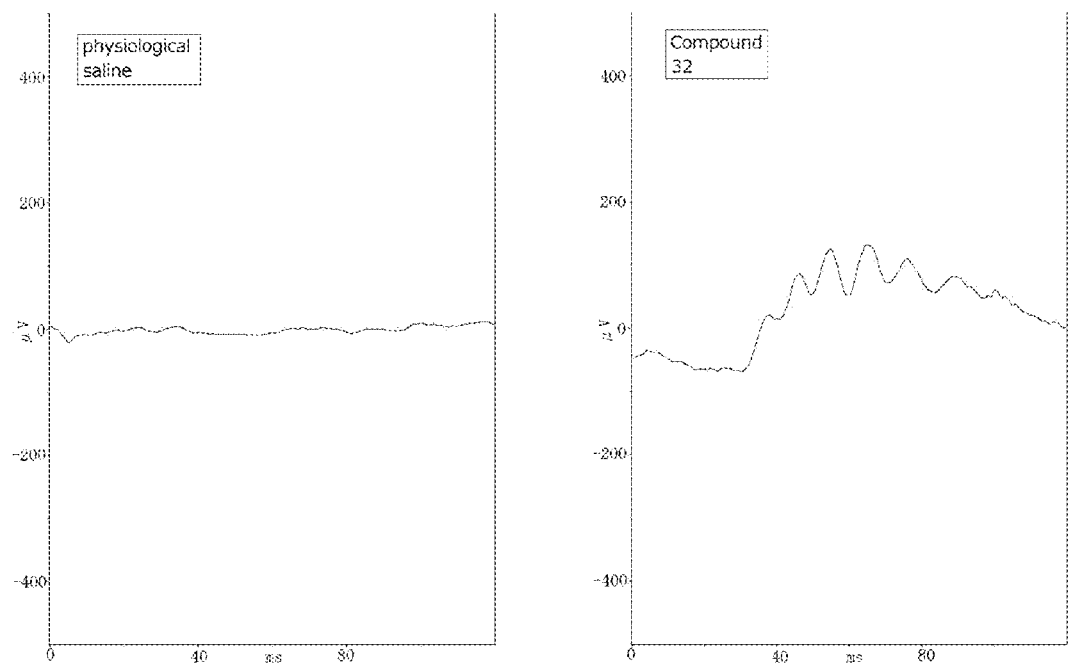
FIG. 24: The electroretinogram of the 33-day-old rd10 mice administered with the physiological saline and Compound 32.
Figure 25:
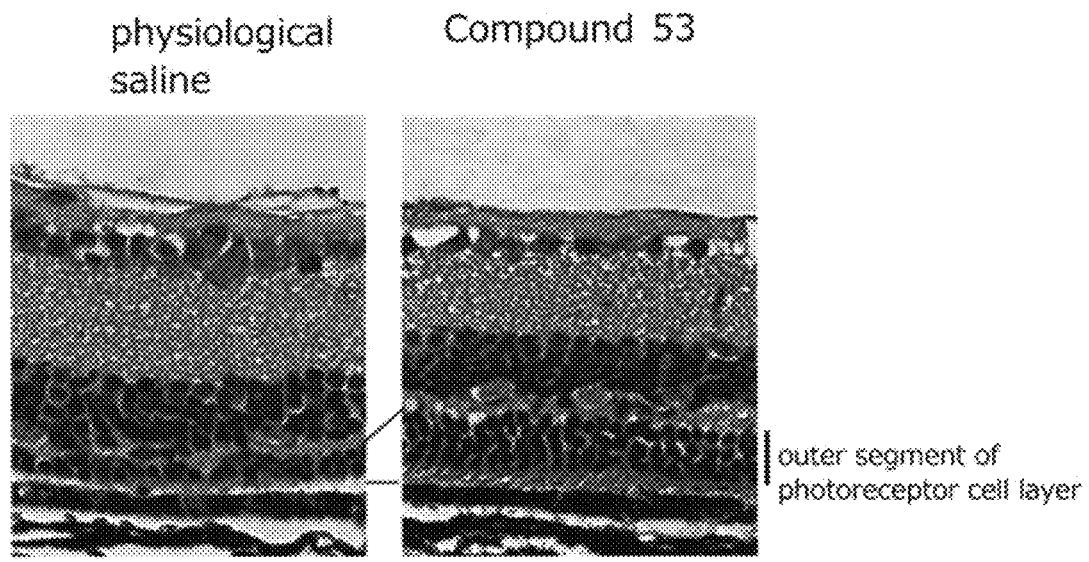
FIG. 25: The HE-stained micrographs of the retinae of the 33-day-old rd10 mice administered with the physiological saline and Compound 53.
Figure 26:
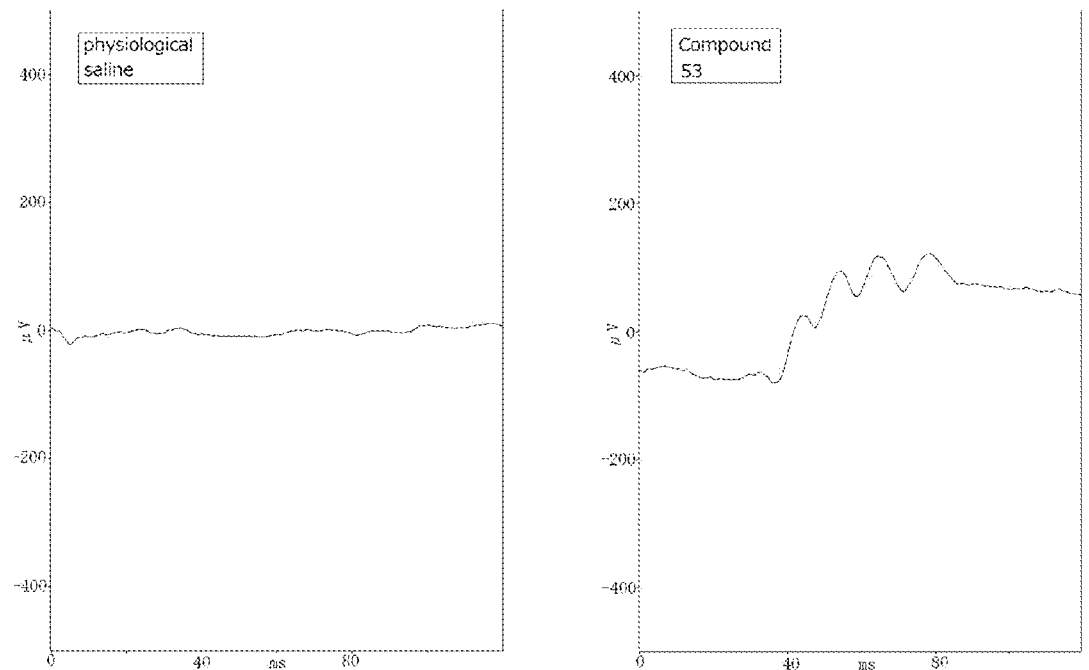
FIG. 26: The electroretinogram of the 33-day-old rd10 mice administered with the physiological saline and Compound 53.
Figure 27:
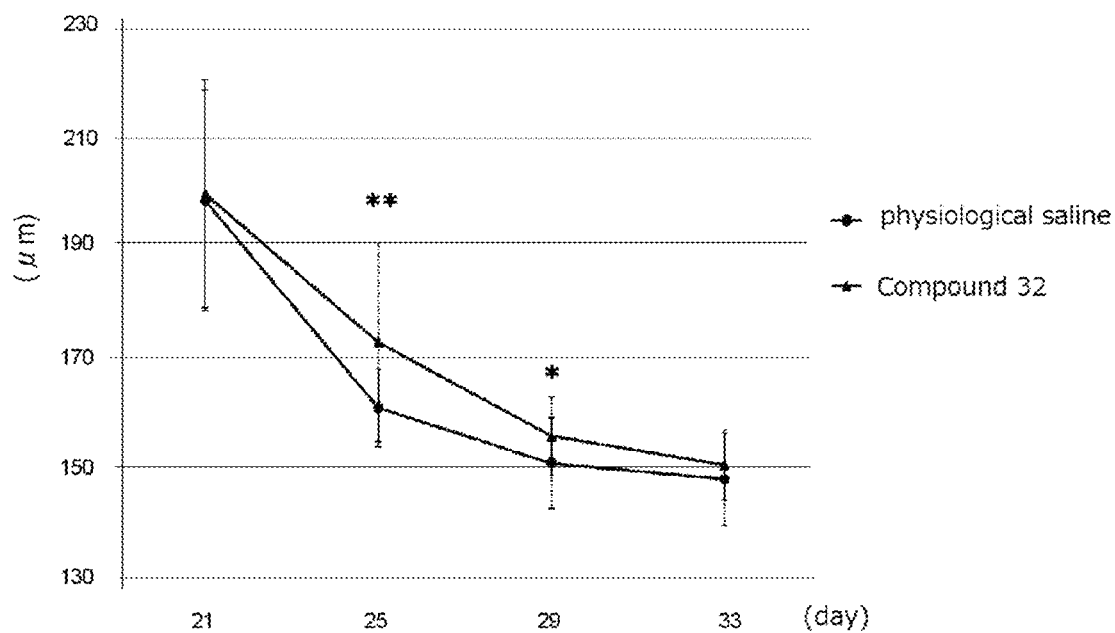
FIG. 27: The time course of the thickness of the entire retina of the rd10 mice administered with the physiological saline and Compound 32. * means significant difference (P=0.011, t-test). ** means significant difference (P=0.0011).
Figure 28:
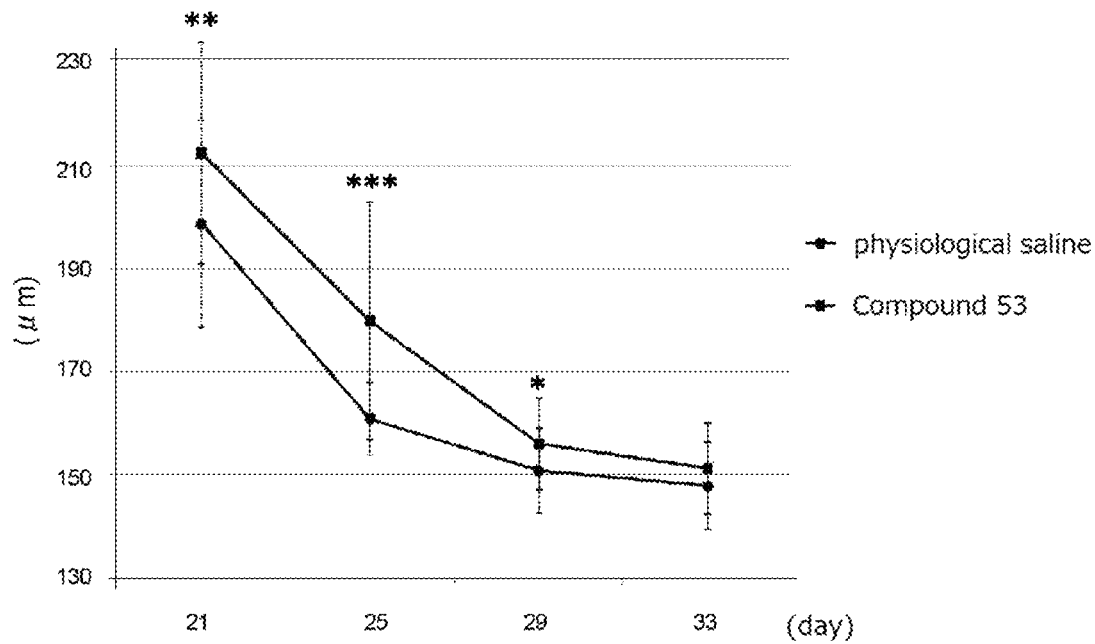
FIG. 28: The time course of the thickness of the entire retina of the rd10 mice administered with the physiological saline and Compound 53. * means significant difference (P=0.012, t-test).  means significant difference (P=0.0050). * means significant difference (P<0.001).
Figure 29:
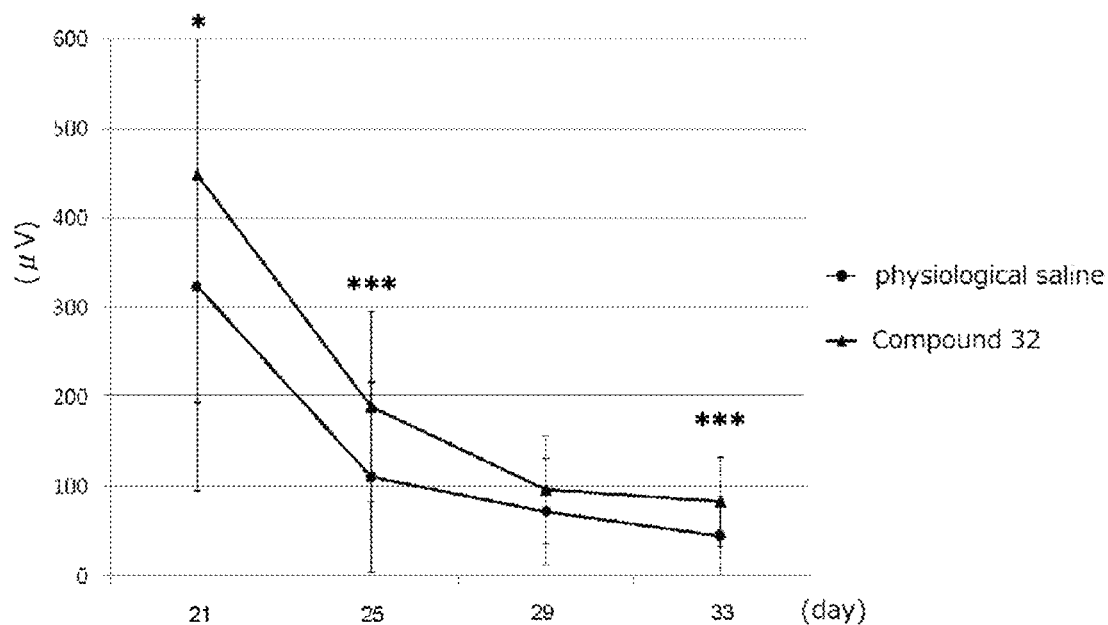
FIG. 29: The time course of the b-wave amplitudes in the electroretinogram (ERG) of the rd10 mice administered with the physiological saline and Compound 32. * means significant difference (P=0.030, t-test). *** means significant difference (P=0.0043, P25; P=0.0028, P33).
Figure 30:
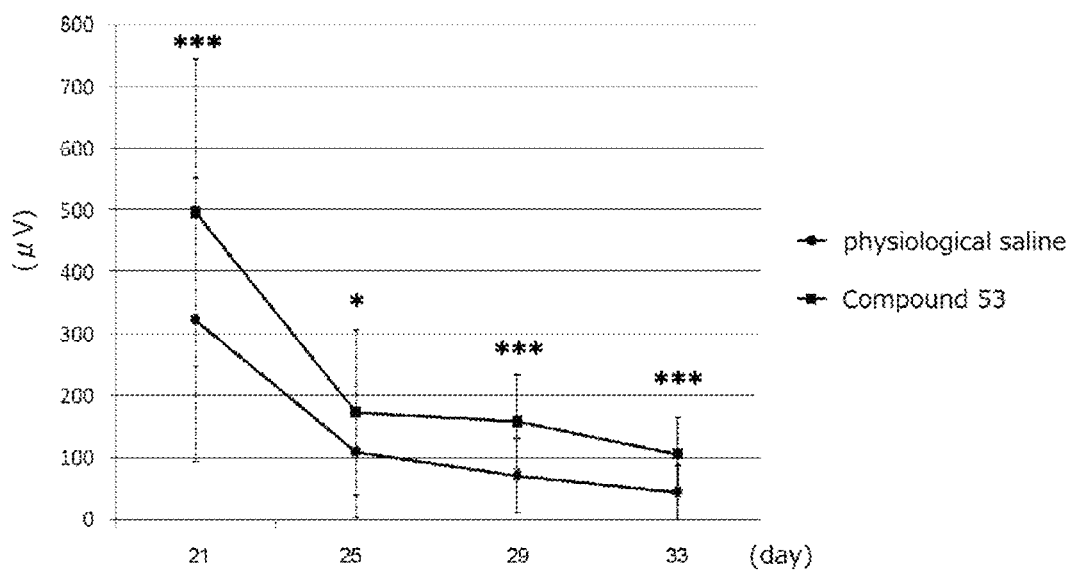
FIG. 30: The time course of the b-wave amplitudes in the electroretinogram (ERG) of the rd10 mice administered with the physiological saline and Compound 53. * means significant difference (P=0.024, t-test). **** means significant difference (P=0.0024, P21; P<0.0001, P29, P33).

As a model of retinitis pigmentosa, the rd10 mice (B6.CXB1-Pde6b$^{rd10}$/J (purchased from Jackson Laboratory (Bar Harbor, Me.), Chang B. et al; Vision Res (2007)) were employed. In the mouse model, the rod photoreceptors are completely disappeared within 2 months after birth. The mice were administered intraperitoneally with 50 mg/kg/day of the compound of Synthetic Example 32 or 53 (Compound 32 or 53, respectively) daily from 7 days of age. The tomographs of the retinae were obtained in the 21, 25, 29 and 33-day-old mice with the optical coherence tomography (OCT) (FIGS. 15 and 17: The OCT images of the mice administered with Compound 32 at 25 and 29 days of age; FIGS. 19 and 21: The OCT images of the mice administered with Compound 53 at 25 and 29 days of age). The 21-, 25-, 29- and 33-day-old mice were subjected to dark adaptation and given 3.0 cd/s/m² of photic stimulations via a LED-type corneal-contact electrode (Mayo) by LS-W (Mayo). The electroretinogram (ERG) was recorded and analyzed with PowerLab 2/25 (AD Instruments, New South Wales, Australia) to measure the b-wave amplitudes (N=27-37 eyes) (FIGS. 16, 18, 24: The ERG of the 25-, 29- and 33-day-old mice administered with Compound 32; FIGS. 20, 22, 26: The ERG of the 25-, 29- and 33-day-old mice administered with Compound 53). The mice in the control group were administered orally with the physiological saline. The eyeballs were enucleated at 33 days of age, and the retinae were observed after HE staining (FIG. 23: The micrographs of the retinae of the 33-day old mice administered with Compound 32 after HE staining; FIG. 25: The micrographs of the retinae of the 33-day old mice administered with Compound 53 after HE staining). The thickness of the entire retina was obtained from the OCT images (FIG. 27: The time course of the thickness of the entire retina of the mice administered with Compound 32 (* means significant difference (P=0.011, t-test).  means significant difference (P=0.0011).); FIG. 28**: The time course of the thickness of the entire retina of the mice administered with Compound 53 (*means significant difference (P=0.012, t-test).  means significant difference (P=0.0050). * means significant difference (P<0.001).).
The time course of the b-wave amplitudes in the electroretinogram (ERG) is shown in FIG. 29 (the mice administered with Compound 32) and 30 (the mice administered with Compound 53).

At 25 days of age, in the OCT (optical coherence tomography) image of the control mice administered with the physiological saline, the layer of the photoreceptor cells were thinned and the junction of the outer segment and the inner segment which is important for the visual function is not seen. Being consistent with the histology, in the electroretinogram the reaction was slight in the control group. At 29 days of age the degeneration and thinning of the photoreceptor cells further developed. In the retinal section of the 33-day-old mice, there was almost one layer of the photoreceptor cells. On the contrary, in the group of mice administered with Compound 32 or 53, the layer of photoreceptor cells were maintained at 25 and 29 days of age in the OCT (optical coherence tomography) images, and the reaction to the photic stimulation was observed in the electroretinogram. In addition, in the retinal section of the 33-day-old mice, there were 4 to 5 layers of the photoreceptor cells in the group of the mice administered with Compound 32 or 53. The structure of the outer segment was also remained.

INDUSTRIAL APPLICABILITY

Based on the results of the pharmacological tests, it is appreciated that the compounds of the present invention, especially the compounds of Synthetic Examples 32 and 53 are useful for the treatment of glaucoma and retinitis pigmentosa. These compounds cannot restore the progressed glaucoma and retinitis pigmentosa to the original normal conditions, but contribute to improve the QOL of the patients by delaying or arresting the progression of the diseases.

The invention claimed is:

1. A method of treating a glaucoma or retinitis pigmentosa comprising administering to a subject in need thereof a therapeutically effective amount of a compound of formula (I)

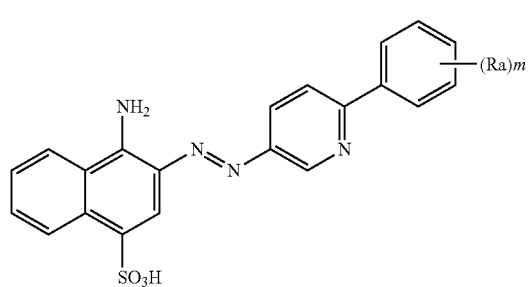

(I)

wherein Ra is selected from the group consisting of halo, hydroxy, alkyl, halo-substituted alkyl, aryl, halo- or alkyl-substituted aryl, alkoxy, hydroxy- or carboxy-substituted alkoxy, aryloxy, halo- or alkyl-substituted aryloxy, CHO, C(O)-alkyl, C(O)-aryl, C(O)-alkyl-carboxyl, C(O)-alkylene-carboxy ester and cyano, and
m is an integer selected from 0 to 4,
or formate ester, acetate ester, propionate ester, butyrate ester, acrylate ester, ethylsuccinate ester, or a pharmaceutically acceptable salt thereof.

2. The method according to claim 1, wherein the compound of formula (I) is a compound of formula

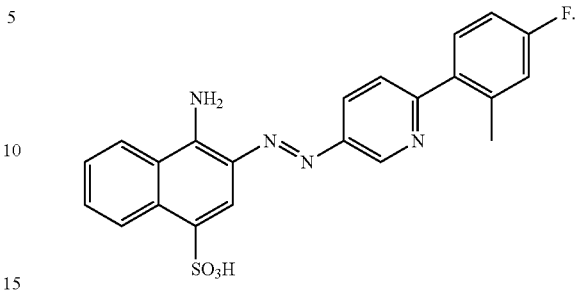

3. The method according to claim 1, wherein the compound of formula (I) is a compound of formula

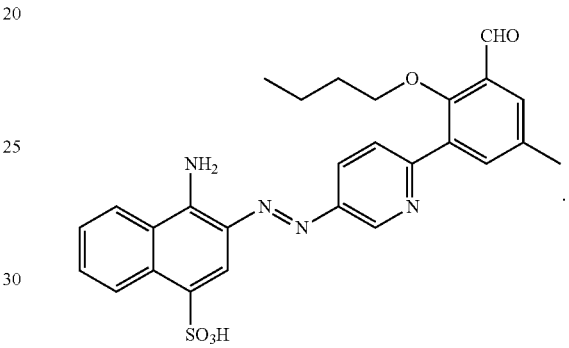

4. The method according to claim 1, wherein the method treats the glaucoma.

5. The method according to claim 1, wherein the method treats the retinitis pigmentosa.

6. The method according to claim 1, comprising administering to the subject in need thereof a therapeutically effective amount of a compound selected from the group consisting of 4-amino-3-(6-phenylpyridine-3-ylazo)naphthalene-1-sulfonic acid sodium salt, 4-amino-3-(6-p-tolylpyridine-3-ylazo)naphthalene-1-sulfonic acid sodium salt, 4-amino-3-(6-m-tolylpyridine-3-ylazo)naphthalene-1-sulfonic acid sodium salt, 4-amino-3-(6-o-tolylpyridine-3-ylazo)naphthalene-1-sulfonic acid sodium salt, 4-amino-3-(6-biphenyl-2-ylpyridine-3-ylazo)naphthalene-1-sulfonic acid sodium salt, 3-[6-(2-acetylphenyl)pyridine-3-ylazo]-4-aminonaphthalene-1-sulfonic acid sodium salt, 3-[6-(3-acetylphenyl)pyridine-3-ylazo]-4-aminonaphthalene-1-sulfonic acid sodium salt, 3-[6-(4-acetylphenyl)pyridine-3-ylazo]-4-aminonaphthalenesulfonic acid sodium salt, 4-amino-3-[6-(2,4-dichlorophenyl)pyridine-3-ylazo]naphthalene-1-sulfonic acid sodium salt, 4-amino-3-[6-(2-trifluoromethylphenyl)pyridine-3-ylazo]naphthalene-1-sulfonic acid sodium salt, 4-amino-3-[6-(4-trifluoromethylphenyl)pyridine-3-ylazo]naphthalene-1-sulfonic acid sodium salt, 4-amino-3-[6-(2-chlorophenyl)pyridine-3-ylazo]naphthalene-1-sulfonic acid sodium salt, 4-amino-3-[6-(3-chlorophenyl)pyridine-3-ylazo]naphthalene-1-sulfonic acid sodium salt, 4-amino-3-[6-(4-chlorophenyl)pyridine-3-ylazo]naphthalene-1-sulfonic acid sodium salt, 4-amino-3-[6-(2-methoxyphenyl)pyridine-3-ylazo]naphthalene-1-sulfonic acid sodium salt, 4-amino-3-[6-(4-methoxyphenyl)pyridine-3-ylazo]naphthalene-1-sulfonic acid sodium salt, 4-amino-3-[6-(2-isopropoxyphenyl)pyridine-3-ylazo]naphthalene-1-sulfonic acid sodium salt, 4-amino-3-[6-(4-isopropoxyphenyl)pyridine-3-ylazo]naphthalene-1-sulfonic acid sodium salt, 4-amino-3-[6-(2-phenoxyphenyl)pyridine-3-ylazo]naphthalene-1-sulfonic acid sodium salt, 4-amino-3-[6-(3-methoxyphenyl)pyridine-3-ylazo]naphthalene-1-sulfonic acid sodium salt, 4-amino-3-[6-(2,3-dimethylphenyl)pyridine-3-ylazo]naphthalene-1-sulfonic acid sodium salt, 4-amino-3-[6-(2,5-dimethylphenyl)pyridine-3-ylazo]naphthalene-1-sulfonic acid sodium salt, 4-amino-3-[6-(3,5-dimethylphenyl)pyridine-3-ylazo]naphthalene-1-sulfonic acid sodium salt, 4-amino-3-[6-(3-trifluoromethylphenyl)pyridine-3-ylazo]naphthalene-1-sulfonic acid sodium salt, methyl 4-{4-[5-(1-amino-4-sulfonaphthalene-2-ylazo)pyridine-2-yl]phenyl}-4-oxobutyrate sodium salt, 4-amino-3-(6-biphenyl-3-ylpyridine-3-ylazo)naphthalene-1-sulfonic acid sodium salt, 4-amino-3-[6-(3-cyanophenyl)pyridine-3-ylazo]naphthalene-1-sulfonic acid sodium salt, 4-amino-3-[6-(4-cyanophenyl)pyridine-3-ylazo]naphthalene-1-sulfonic acid sodium salt, 4-amino-3-[6-(3,5-bistrifluoromethylphenyl)pyridine-3-ylazo]naphthalenesulfonic acid sodium salt, 4-amino-3-[6-(4-benzoylphenyl)pyridine-3-ylazo]naphthalene-1-sulfonic acid sodium salt, 4-amino-3-[6-(2-propoxyphenyl)pyridine-3-ylazo]naphthalene-1-sulfonic acid sodium salt, 4-amino-3-[6-(4-fluoro-2-methylphenyl)pyridine-3-ylazo]naphthalene-1-sulfonic acid sodium salt, 4-amino-3-[6-(5-fluoro-2-propoxyphenyl)pyridine-3-ylazo]naphthalene-1-sulfonic acid sodium salt, 4-amino-3-[6-(2-fluoro-6-propoxyphenyl)pyridine-3-ylazo]naphthalene-1-sulfonic acid sodium salt, 4-amino-3-[6-(4-fluoro-2-propoxyphenyl)pyridine-3-ylazo]naphthalene-1-sulfonic acid sodium salt, 4-amino-3-[6-(5-fluoro-2-methylphenyl)pyridine-3-ylazo]naphthalene-1-sulfonic acid sodium salt, 4-amino-3-[6-(2-fluoro-5-methylphenyl)pyridine-3-ylazo]naphthalene-1-sulfonic acid sodium salt, 4-amino-3-[6-(2-butoxyphenyl)pyridine-3-ylazo]naphthalene-1-sulfonic acid sodium salt, 4-amino-3-[6-(2-hexyloxyphenyl)pyridine-3-ylazo]naphthalene-1-sulfonic acid sodium salt, 4-amino-3-[6-(4-butylphenyl)pyridine-3-ylazo]naphthalene-1-sulfonic acid sodium salt, 4-amino-3-[6- (2-hydroxyphenyl)pyridine-3-ylazo]naphthalene-1-sulfonic acid sodium salt, 4-amino-3-{6-[2-(6-hydroxyhexyloxyl)phenyl]pyridine-3-ylazo}naphthalene-1-sulfonic acid sodium salt, 4-{2-[5-(1-amino-4-sulfonaphthalene-2-ylazo)pyridine-2-yl]phenoxy}butyric acid disodium salt, 4-amino-3-{6-[2-(3-hydroxypropoxyl)phenyl]pyridine-3-ylazo}naphthalene-1-sulfonic acid sodium salt, 4-amino-3-[6-(2-isobutoxyphenyl)pyridine-3-ylazo]naphthalene-1-sulfonic acid sodium salt, 4-amino-3-[6-(5-chloro-2-hydroxyphenyl)pyridine-3-ylazo]naphthalene-1-sulfonic acid sodium salt, 4-amino-3-[6-(4-methylbiphenyl-2-yl)pyridine-3-ylazo]naphthalene-1-sulfonic acid sodium salt, 4-amino-3-[6-(4'-chloro-4-methylbiphenyl-2-yl)pyridine-3-ylazo]naphthalene-1-sulfonic acid sodium salt, 4-amino-3-[6-(4,3',5'-trimethylbiphenyl-2-yl)pyridine-3-ylazo]naphthalene-1-sulfonic acid sodium salt, 4-amino-3-[6-(3'-chloro-4-methylbiphenyl-2-yl)pyridine-3-ylazo]naphthalene-1-sulfonic acid sodium salt, 4-amino-3-[6-(2,6-dimethylphenyl)pyridine-3-ylazo]naphthalene-1-sulfonic acid sodium salt, 4-amino-3-[6-(3-formyl-2-isopropoxy-5-methylphenyl)pyridine-3-ylazo]naphthalene-1-sulfonic acid sodium salt, and 4-amino-3-[6-(3-formyl-2-butoxy-5-methylphenyl)pyridine-3-ylazo]naphthalene-1-sulfonic acid sodium salt.

7. The method according to claim 1, wherein the therapeutically effective amount is from about 0.001 to about 1000 mg/kg body weight daily.

8. The method according to claim 1, wherein the subject is human.

9. The method according to claim 1, wherein the compound is administered in the form of a composition further comprising a pharmaceutically acceptable solvent.

10. The method of claim 9, wherein the pharmaceutically acceptable solvent is water.

11. The method of claim 9, wherein the composition is in a solid form.

12. The method of claim 9, wherein the composition is in a liquid form.

* * * * *